United States Patent
Sigurdsson

(10) Patent No.: US 11,787,854 B2
(45) Date of Patent: Oct. 17, 2023

(54) IMMUNOLOGICAL TARGETING OF PATHOLOGICAL TAU PROTEINS

(71) Applicant: New York University, New York, NY (US)

(72) Inventor: Einar M. Sigurdsson, Scarsdale, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 17/090,359

(22) Filed: Nov. 5, 2020

(65) Prior Publication Data

US 2021/0061894 A1    Mar. 4, 2021

Related U.S. Application Data

(60) Continuation of application No. 15/400,533, filed on Jan. 6, 2017, now abandoned, which is a continuation of application No. 14/261,506, filed on Apr. 25, 2014, now abandoned, which is a division of application No. 12/813,297, filed on Jun. 10, 2010, now Pat. No. 8,748,386.

(60) Provisional application No. 61/185,895, filed on Jun. 10, 2009.

(51) Int. Cl.
| | |
|---|---|
| *C07K 16/18* | (2006.01) |
| *A61K 39/00* | (2006.01) |
| *G01N 33/68* | (2006.01) |
| *A61K 39/395* | (2006.01) |

(52) U.S. Cl.
CPC .......... *C07K 16/18* (2013.01); *A61K 39/0005* (2013.01); *A61K 39/0007* (2013.01); *A61K 39/3955* (2013.01); *G01N 33/6896* (2013.01); *A61K 2039/505* (2013.01); *A61K 2039/507* (2013.01); *C07K 2317/20* (2013.01); *C07K 2317/76* (2013.01); *G01N 2800/2821* (2013.01)

(58) Field of Classification Search
None
See application file for complete search history.

(56) References Cited

U.S. PATENT DOCUMENTS

| | | | |
|---|---|---|---|
| 5,492,812 | A  | 2/1996 | Vooheis |
| 6,232,437 | B1 | 5/2001 | Vandermeeren |
| 6,238,892 | B1 | 5/2001 | Mercken et al. |
| 6,713,450 | B2 | 3/2004 | Frangione et al. |
| 6,821,504 | B2 | 11/2004 | Wisniewski et al. |
| 7,408,027 | B1 | 8/2008 | Mandelkow et al. |
| 7,427,655 | B2 | 9/2008 | Frangione et al. |
| 7,446,180 | B2 | 11/2008 | Novak |
| 7,479,482 | B2 | 1/2009 | Frangione et al. |
| 7,632,816 | B2 | 12/2009 | Wisniewski et al. |
| 7,700,107 | B2 | 4/2010 | Frangione et al. |
| 8,012,936 | B2 | 9/2011 | Sigurdsson et al. |
| 2002/0197258 | A1 | 12/2002 | Ghanbari et al. |
| 2007/0059807 | A1 | 3/2007 | Wisniewski et al. |
| 2008/0050383 | A1 | 2/2008 | Sigurdsson et al. |
| 2008/0220449 | A1 | 9/2008 | Vasan et al. |
| 2009/0098155 | A1 | 4/2009 | Garsky et al. |
| 2011/0318358 | A1 | 12/2011 | Sigurdsson et al. |

FOREIGN PATENT DOCUMENTS

| | | |
|---|---|---|
| JP | 2916297 | 9/1992 |
| WO | WO 1993/011231 | 6/1993 |
| WO | WO 1998/022120 | 5/1998 |
| WO | WO 2002/064084 | 8/2002 |
| WO | WO 2003/045128 | 6/2003 |
| WO | WO 2010/106127 | 9/2010 |
| WO | WO 2010/115843 | 10/2010 |
| WO | WO 2011/013034 | 2/2011 |

OTHER PUBLICATIONS

Google.com "Peptide" accessed on Aug. 19, 2022 (Year: 2022).*
Biopeptek "Antibody modifications" accessed from biopeptek.com on Aug. 19, 2022 (Year: 2004).*
Weidner, Adam "Final Office Action" dated May 12, 2020 in U.S. Appl. No. 15/400,533 (Year: 2020).*
Weidner, Adam "Non-Final Office Action" dated Aug. 7, 2019 in U.S. Appl. No. 15/400,533 (Year: 2019).*
Anderson, D.C. et al. (1990) "Use of Flanking Sequences to Study Secondary Structure-Activity Correlations of a Mycobacterium leprae T Cell Epitope," Eur. J. Immunol. 20:2691-2697.
Anfinsen, C.B. (1973) "Principles That Govern The Folding Of Protein Chains," Science 181(4096):223-230.
Asuni et al. (2006) "Tau-based Immunotherapy for Dementia," The 10th International Conference on Alzheimer's Disease, Alzheimer's and Dementia, Madrid, Spain, Alzheimer's & Dementia 2(3) Suppl. 1, Feb. 5, 2004, S40-S41 (Abstract) (Available online Jun. 5, 2006).
Asuni et al. (2007) "Immunotherapy Targeting Pathological Tau Conformers in a Tangle Mouse Model Reduces Brain Pathology with Associated Functional Improvements," J. Neurosci. 27(34):9115-9129.
Auerbach, J. (2013) Response to the Official Action dated Aug. 15, 2013) filed in U.S. Appl. No. 12/813,297.
Basurto-Islas et al. (2008) "Accumulation of Aspartic Acid (421 )-and Glutamic Acid(391)-Cleaved Tau in Neurofibrillary Tangles Correlates with Progression in Alzheimer Disease," J. Neuropathol. Exp. Neurol. 67(5):470-483.

(Continued)

*Primary Examiner* — Adam Weidner
(74) *Attorney, Agent, or Firm* — Troutman Pepper Hamilton Sanders LLP (Rochester)

(57) ABSTRACT

The present invention relates to methods and compositions for treating, preventing, and diagnosing Alzheimer's Disease or other tauopathies in a subject by administering an immunogenic tau peptide or an antibody recognizing the immunogenic tau epitope under conditions effective to treat, prevent, or diagnose Alzheimer's Disease or other tauopathies. Also disclosed are methods of promoting clearance of aggregates from the brain of the subject and of slowing progression of tau-pathology related behavioral phenotype in a subject.

13 Claims, 18 Drawing Sheets
Specification includes a Sequence Listing.

(56) References Cited

OTHER PUBLICATIONS

Bergmann C.C. et al. (1994) "Differential Effects of Flanking Residues on Presentation of Epitopes from Chimeric Peptides," J. Virol. 68(8):5306-5310.

Bergmann C.C. et al. (1996) "Flanking Residues Alter Antigenicity And Immunogenicity Of Multi-Unit CTL Epitopes," J. Immunol. 157:3242-3249.

Bibl, M. et al. (2012) "Neurochemical Biomarkers In Alzheimer's Disease And Related Disorders," Ther, Adv. Neurolog. Disorders 5(6):335-348.

Billingsley, M,L. et al. (1997) "Regulated Phosphorylation And Dephosphorylation Of Tau Protein: Effects on Microtuble Interaction, Intracellular Trafficking And Neurodegeneration," Biochem. J. 323:577-591.

Boutajangout, A. et al. (2011) "Passive Immunization Targeting Pathological Phospho-Tau Protein In A Mouse Model Reduces Functional Decline And Clears Tau Aggregates From The Brain," J. Neurochem. 118(4):658-667.

Boutajangout, A. et al. (2011) "Passive Tau Immunotherapy Diminishes Functional Decline And Clears Tau Aggregates In A Mouse Model Of Tauopathy," Alzheimer's & Dementia: The Journal Of The Alzheimer's Association 6(4):S5 (1 page).

Boutajangout, A. et al. (Jul. 10, 2010) "*Passive Tau Immunotherapy Diminishes Functional Decline And Clears Tau Aggregates In A Mouse Model Of Tauopathy*," Alzheimer's & Dementia: The Jornal Of The Alzheimer's Association 6(4):S578; Abstact P3-427 (1 page).

Briggs, S. et al. (1993) "Fine Specificity of Antibody Recognition of Carcinoma-Associated Epithelial Mucins: Antibody Binding to Synthetic Peptide Epitopes," Eur. J. Cancer 29A(2):230-237.

Calignon et al. (2010) "Caspase Activation Precedes and Leads to Tangles," Nature 464:1201-1205.

Clarivate Analytics, Database WPI 1-14, Week 199245, Thomson Scientific, London, GB; An 1992-369428 XP002778304 & JP H04 270300 A (Mitsubishi Kasei); (1992) (2 pages).

Craig, L. et al. (1998) "The Role of Structure in Antibody Cross-reactivity Between Peptides and Folded Proteins," J. Mol. Biol. 281:183-201.

Dyson, H.J. (1988) "Folding of Immunogenic Peptide Fragments of Proteins in Water Solution; I. Sequence Requirements for the Formation of a Reverse Turn," J. Mol. Biol. 201:161-200.

EPO—Provided Machine Translation of JP2916297B B2 19990705 (1992) (prepared (2017) (7 pages).

Extended Search Report EP 17197129.4 (dated Mar. 12, 2018) pp. 1-17.

Eurasian Patent Search Report Appln No. 201171397 (2012) (4 pages).

Fagan, A.M. et al. (2012) "Upcoming Candidate Cerebrospinal Fluid Biomarkers Of Alzheimer's Disease," Biomarkers Med. 6(4):455-476.

Fath, T. et al. (2002) "Tau-Mediated Cytotoxicity in a Pseudohyperphosphorylation Model of Alzheimer's Disease," J. Neurosci. 22(22):9733-9741.

Fieser, T.M. et al. (1987) "Influence Of Protein Flexibility And Peptide Conformation On Reactivity Of Monoclonal Anti-Peptide Antibodies With A Protein α-Helix," Proc. Natl. Acad. Sci. (U.S.A.) 84:8568-8572.

Furie, B. et al. (1974) "Antibodies To The Unfolded Form Of A Helix-Rich Region In Staphylococcal Nuclease," Biochemistry 13(8):1561-1566.

Gen Bank Accession No. EAW93567 (Dec. 18, 2006).

Ghillani, P. et al. (1988) "Monoclonal Antipeptide Antibodies As Tools To Dissect Closely Related Gene Products. A Model Using Peptides Encoded By The Calcitonin Gene," J. Immunol. 141:3156-3163.

Gokhale, A.S. et al. (2014) "Peptides And Peptidomimetics As Immunomodulators," Immunotherapy 6(6):755-774.

Hasegawa, M. et al. (1993) "*Characterization Of Two Distinct Monoclonal Antibodies To Paired Helical Filaments: Further Evidence For Fetal-Type Phosphorylation Of The Tau In Paired Helical Filaments*," J. Neurochem. 60(6):2068-2077.

Heemskerk, M. H. M. et al. (1995) "Differential Activation Of Mouse Hepatitis Virus-Specific CD4+ Cytotoxic T Cells Is Defined By Peptide Length," Immunology 85:517-522.

Hoffmann, R. et al. (1997) "Unique Alzheimer's Disease Paired Helical Filament Specific Epitopes Involve Double Phosphorylation At Specific Sites," Biochemistry. 36(26):8114-8124.

Hunt, J.C. et al. (1990) "Mouse Monoclonal Antibody 5-21-3 Recognizes A Contiguous, Conformation-Dependent Epitope And Maps To A Hydrophilic Region In HIV-1 gp41," AIDS Res. Hum. Retrovir. 6(5):587-598.

International Preliminary Report on Patentability dated Dec. 12, 2011.

International Search Report dated Mar. 29, 2011.

Jackson, D.C. et al. (2000) "Preparation And Properties Of Totally Synthetic Immunogens," Vaccine 18:355-361.

Johnson et al. (2004) "Tau Phosphorylation in Neuronal Cell Function and Dysfunction," J. Cell Science 117 (24):5721-5729.

Knopman, D.S. et al. (2001) "Practice Parameter: Diagnosis Of Dementia (An Evidence-Based Review) Report Of The Quality Standards Subcommittee Of The American Academy Of Neurology," Neurology 56:1143-1153.

Krishnamurthy, P. et al. (2009) "Immunotherapy Targeting Alzheimer's Phospho-Tau Epitope Within The Microtubule Binding Region Of Tau Clears Pathological Tau And Prevents Functional Decline In A Mouse Model Of Tauopathy," Alzheimer's & Dementia: The Journal Of The Alzheimer's Association 5(4):P112 (1 page).

Novak et al. (1993) "Molecular Characterization of the Minimal Protease Resistant Tau Unit of the Alzheimer's Disease Paired Helical Filament," EMBO J. 12(1):365-370.

Novak, M. (1994) "Truncated Tau Protein as a New Marker for Alzheimer's Disease," Acta Virologica 38(3):173-189.

Novak, M. (2009) "Tau Vaccine: Active Immunization with Misfolded Tau Protein Attenuates Tau Pathology in the Transgenic Rat Model of Tauopathy," Alzheimer's and Dementia 5(4)Supp:1-2 (2009) (Abstract only).

Nyberg, L. (2014) "Alzheimer's Research: 3 Reasons for Hope," http://journalstar.com/niche/neighborhood-extra/senior-scene/alzheimer-s-research-reasons-for-hope/article_alfcc704-c3ab-5a70-aa8d-ea7bcaa481c6.html [redacted to remove advertisements]; 2 pages.

Otvos, L. (1994) "*Monoclonal Antibody PHF-1 Recognizes Tau Protein Phosphorylated At Serine Residues 396 And 404*," J. Neurosci. Res. 39(6):669-673.

Park et al. (2005) "The Generation of 17 kDa Neurotoxic Fragment: An Alternative Mechanism by Which Tau Mediates Beta-Amyloid-Induced Neurodegeneration," J. Neurosci. 25{22}:5365-5375.

Pérez, M et al. (2001) "In Vitro Assembly of Tau Protein: Mapping the Regions Involved in Filament Formation," Biochem. 40(20):5983-5991.

Raman, C.S. et al. (2000) "Antibody-Detected Folding: Kinetics Of Surface Epitope Formation Are Distinct From Other Folding Phases," Polymer Sci. 9:129-137.

Rosenmann et al. (2006) "Tauopathy-like Abnormalities and Neurologic Deficits in Mice Immunized with Neuronal Tau Protein," Arch. Neurol. 63:1459-1467.

Sachs, D.H. et al. (1972) "An Immunologic Approach To The Conformational Equilibria Of Polypeptides," Proc. Natl. Acad. Sci. (U.S.A.) 69:3790-3794.

Sachs, D.H. et al. (1972) "Antibodies to a Distinct Antigenic Determinant of *Staphyloccocus* Nuclease," J. Immunol. 109(6):1300-1310.

Schenk et al. (1999) "Immunization with Amyloid-Beta Attenuates Alzheimer-Disease-Like Pathology in the PDAPP Mouse," Nature 400:173-177.

Shahpasand, K. et al. (2012) "Regulation of Mitochondrial Transport and Inter-Microtubule Spacing by Tau Phosphorylation at the Sites Hyperphosphorylated in Alzheimer's Disease," J. Neurosci. 32(7):2430-2441.

Sigurdsson, E.M. (2000) "*In Vivo Reversal of Amyloid-β Lesions in Rat Brain*" J. Neuropathol. Exper. Neurol. 59(1):11-178.

(56) References Cited

OTHER PUBLICATIONS

Sigurdsson, E.M. (2008) "Immunotherapy Targeting Pathological Tau Protein in Alzheimer's Disease and Related Tauopathies," J. Alzheimer's Dis. 15(2):157-168.

Sigurdsson, E.M. (2009) "Tau-Focused Immunotherapy for Alzheimer's Disease and Related Tauopathies," Curr. Alzheimer Res. 6(5):446-450 (2009).

Sigurdsson, E.M. et al. (2008) "Tau Immunotherapy Prevents Cognitive Decline And Clears Pathological Tau In A Tangle Mouse Model," Alzheimer's & Dementia: The Journal Of The Alzheimer's Association 4(4):T191-T192 (2 pages).

Steers, N.J. et al. (2014) "Designing The Epitope Flanking Regions For Optimal Generation Of CTL Epitopes," Vaccine 32:3509-3516.

Supplemental Search Report EP 10786852.3 (dated Sep. 10, 2013) pp. 1-16.

Taniguchi et al. (2005) "Effects of Different Anti-Tau Antibodies on Tau Fibrillogenesis: RTA-1 and RTA-2 Counteract Tau Aggregation," Febs Lett. 579(6):1399-1404.

Troquier et al. (2009) "Immunotherapy Targeting Tau," The Biology and Pathology of Tau and its Role in Tauopathies, Biochemical Society, Cambridge, UK, Jan. 7-8, 2010 (abstract available online Dec. 2009).

Vignali, D.A.A. et al. (1994) "Amino Acid Residues that Flank Core Peptide Epitopes and the Extracellular Domains of CD4 Modulate Differential Signaling through the T Cell Receptor," J. Exp. Med. 179:1945-1956.

Written Opinion of the International Searching Authority dated Mar. 29, 2011.

Zichel, R. et al. (2012) "Aptamers as a Sensitive Tool to Detect Subtle Modifications in Therapeutic Proteins," Plos One 7(2):e31948; pp. 1-11.

Zilka et al. (2008) "Chaperone-Like Antibodies Targeting Misfolded Tau Protein: New Vistas in the Immunotherapy of Neurodegenerative Foldopathies," J. Alzheimer's Disease 15:169-179.

"Poloxamer," Wikipedia (2023) 5 pages.

Official Action, CA 3,120,504 (2023) 6 pages.

2011 Biopeptek WebPages Recorded by The Wayback Machine, https://web.archive.org/web/20230000000000*/http://biopeptek.com; 3 pages.

* cited by examiner

A.

B.

US 11,787,854 B2

IMMUNOLOGICAL TARGETING OF PATHOLOGICAL TAU PROTEINS

CROSS-REFERENCE TO RELATED APPLICATIONS

This application is a continuation of U.S. Non-Provisional patent application Ser. No. 15/400,533 (filed Jan. 6, 2017; pending), which is a continuation of U.S. patent application Ser. No. 14/261,506 (filed Apr. 25, 2014; abandoned), which is a divisional application of U.S. Non-Provisional patent application Ser. No. 12/813,297 (filed Jun. 10, 2010; patented as U.S. Pat. No. 8,748,386 on Jun. 10, 2014), and which claims priority to U.S. Provisional Patent Application Ser. No. 61/185,895 (filed Jun. 10, 2009; expired). This application claims priority to each of such applications, each of which applications is hereby incorporated by reference in its entirety.

STATEMENT REGARDING FEDERALLY SPONSORED RESEARCH OR DEVELOPMENT

The subject matter of this application was made with support from the United States Government under the National Institutes of Health, Grant No. AG032611. The U.S. Government has certain rights in the invention.

REFERENCE TO SEQUENCE LISTING

This application includes one or more Sequence Listings pursuant to 37 C.F.R. 1.821 et seq., which are disclosed in computer-readable media (file name: 1400-0002C4_Sequence_Listing.txt, created on Nov. 4, 2020, and having a size of 53,568 bytes), which file is herein incorporated by reference in its entirety.

FIELD OF THE INVENTION

The present invention is directed to immunological methods and compositions for preventing, treating, and diagnosing Alzheimer's disease and related tauopathies, and inhibiting the accumulation of tau neurofibrillary tangles and/or their pathological tau precursors in a subject.

BACKGROUND OF THE INVENTION

An emerging treatment for Alzheimer's disease (AD) is immunotherapy to clear amyloid-β (Aβ). Another important target in AD and frontotemporal dementia is the neurofibrillary tangles and/or their pathological tau protein conformers, whose presence correlates well with the degree of dementia (Terry R., "Neuropathological Changes in Alzheimer Disease," *Prog Brain Res.* 101:383-390 (1994); Goedert M., "Tau Protein and Neurodegeneration," *Semin Cell Dev Biol.* 15:45-49 (2004)). The objective of immunotherapy for tau pathology is that anti-tau antibodies can clear tau aggregates that may affect neuronal viability. Other components of the immune system may play a role as well in the clearance. Tau is a soluble protein that promotes tubulin assembly, microtubule stability, and cytoskeletal integrity. Although tau pathology is likely to occur following Aβ aggregation based on Down syndrome studies, analyses of AD brains and mouse models indicate that these pathologies are likely to be synergistic (Sigurdsson et al., "Local and Distant 30 Histopathological Effects of Unilateral Amyloid-beta 25-35 Injections into the Amygdala of Young F344 Rats," *Neurobiol Aging* 17:893-901 (1996); Sigurdsson et al., "Bilateral Injections of Amyloid-β 25-35 into the Amygdala of Young Fischer Rats: Behavioral, Neurochemical, and Time Dependent Histopathological Effects," *Neurobiol Aging* 18:591-608 (1997); Lewis et al., "Enhanced Neurofibrillary Degeneration in Transgenic Mice Expressing Mutant Tau and APP," *Science* 293(5534):1487-91 (2001); Gotz et al., "Formation of Neurofibrillary Tangles in P301L Tau Transgenic Mice Induced by A-beta 42 Fibrils," *Science* 293:1491-1495 (2001); Delacourte et al., "Nonoverlapping but Synergetic Tau and APP Pathologies in Sporadic Alzheimer's Disease," *Neurology.* 59:398-407 (2002); Oddo et al., "Abeta Immunotherapy Leads to Clearance of Early, But Not Late, Hyperphosphorylated Tau Aggregates via the Proteasome," *Neuron* 43:321-332 (2004); Ribe et al., "Accelerated Amyloid Deposition, Neurofiblillary Degeneration and Neuronal Loss in Double Mutant APP/Tau Transgenic Mice," *Neurobiol Dis.* (2005)). Hence, targeting both pathologies may substantially increase treatment efficacy. To date, no tau mutations have been observed in AD, however, in frontotemporal dementia, mutations in the tau protein on chromosome 17 (FTDP-17) are a causative factor in the disease, which fu11her supports tau-based therapeutic approaches (Poorkaj et al., "Tau is a Candidate Gene for Chromosome 17 Frontotemporal Dementia," *Ann Neural.* 43:815-825 (1998); Spillantini et al., "Frontotemporal Dementia and Parkinsonism Linked to Chromosome 17: A New Group of Tauopathies," *Brain Pathol.* 8:387-402 (1998)). Transgenic mice expressing these mutations have modeled many aspects of the disease and are valuable tools to study the pathogenesis of tau-pathology related neurodegeneration and to assess potential therapies. One of these models, the P301 L mouse model (Lewis et al., "Neurofibrillary Tangles, Amyotrophy and Progressive Motor Disturbance in Mice Expressing Mutant (P301L) Tau Protein," *Nat Gener.* 25:402-405 (2000)), recapitulates many of the features of frontotemporal dementia although the CNS distribution of the tau aggregates results primarily in sensorimotor abnormalities which complicates cognitive assessment. Homozygous lines of this mouse model have an early onset of CNS pathology and associated functional impairments which make them ideal for the initial assessment of the feasibility of immunotherapy, targeting pathological tau conformers.

Other tau-related therapeutic approaches include: (1) drugs that inhibit the kinases or activate the phosphatases that affect the state of tau phosphorylation (Iqbal et al., "Inhibition of Neurofibrillary Degeneration: A Promising Approach to Alzheimer's Disease and Other Tauopathies," *Curr Drug Targets* 5:495-502 (2004); Noble et al., Inhibition of Glycogen Synthase Kinase-3 by Lithium Correlates with Reduced Tauopathy and Degeneration In Vivo," *Proc Natl Acad Sci USA* 102:6990-6995 (2005)); (2) microtubule stabilizing drugs (Michaelis et al., {beta}-Amyloid-Induced Neurodegeneration and Protection by Structurally Diverse Microtubule-Stabilizing Agents," *J Pharmacol Exp Ther.* 312:659-668 (2005); Zhang et al., "Microtubule-Binding Drugs Offset Tau Sequestration by Stabilizing Microtubules and Reversing Fast Axonal Transport Deficits in a Tauopathy Model," *Proc Natl Acad Sci USA* 102:227-231 (2005)); (3) compounds that interfere with tau aggregation (Pickhardt et al., "Anthraquinones Inhibit Tau Aggregation and Dissolve Alzheimer's Paired Helical Filaments In Vitro and in Cells," *J Biol Chem.* 280:3628-3635 (2005)); and (4) drugs that promote heat shock protein mediated clearance of tau (Dickey et al., "Development of a High Throughput Drug Screening Assay for the Detection of Changes in Tau Levels—Proof of Concept with HSP90 Inhibitors," *Curr*

*Alzheimer Res.* 2:231-238 (2005)). While all these approaches are certainly worth pursuing, target specificity and toxicity are of a concern, which emphasizes the importance of concurrently developing other types of tau-targeting treatments, such as immunotherapy.

The present invention is directed to overcoming these and other deficiencies in the art.

SUMMARY OF THE INVENTION

A first aspect of the present invention is directed to a method of preventing or treating Alzheimer's disease or other tauopathy in a subject. This method involves administering, to the subject, any one or more immunogenic tau peptides having an amino acid sequence selected from the group consisting of SEQ ID NOs: 2-75, or one or more antibodies recognizing an immunogenic tau epitope comprising an amino acid sequence selected from the group consisting of SEQ ID NOs: 2-75 and 101-103 under conditions effective to treat or prevent Alzheimer's disease or other tauopathy in the subject.

Another aspect of the present invention is directed to a method of promoting clearance of tau aggregates from the brain of a subject. This method involves administering, to the subject, any one or more immunogenic tau peptides having an amino acid sequence selected from the group consisting of SEQ ID NOs: 2-75, or one or more antibodies recognizing an immunogenic tau epitope comprising an amino acid sequence selected from the group consisting of SEQ ID NOs: 2-75 and 101-103 under conditions effective to promote clearance of the tau aggregates from the brain of the subject.

A third aspect of the present invention is directed to a method of slowing progression of a tau-pathology related behavioral phenotype in a subject. This method involves administering, to the subject, any one or more immunogenic tau peptides having an amino acid sequence selected from the group consisting of SEQ ID NOs: 2-75, or one or more antibodies recognizing an immunogenic tau epitope comprising an amino acid sequence selected from the group consisting of SEQ ID NOs: 2-75 and 101-103 under conditions effective to slow the progression of the tau-pathology related behavioral phenotype in the subject.

A fourth aspect of the present invention is directed to an isolated tau peptide comprising an amino acid sequence selected from the group consisting of SEQ ID NOs: 2-75 and 101-103. The immunogenic tau peptide is effective in preventing and treating Alzheimer's disease or other tauopathy in a subject, promoting the clearance of aggregates from the brain of a subject, and slowing the progression of a tau-pathology related behavioral phenotype in a subject.

Neurofibrillary tangles and their pathological tau protein conformers are important targets for preventing and treating Alzheimer's disease and other tau-related neurodegenerative diseases. However, a strategy for targeting and clearing neurofibrillary tangles and/or pathological tau conformers that has high target specificity and minimal to no toxicity is lacking. The immunogenic tau peptides and antibodies described herein were designed to overcome this deficiency. Because the immunogenic tau peptides of the present invention mimic narrow phospho-epitopes of the pathological tau, and the tau antibodies recognize these same narrow phospho-epitopes, enhanced specificity and safety are achieved. This scenario also applies to the antibodies described herein that are generated against the free N- or C-terminus of pathological tau fragments. Accordingly, using the immunotherapeutic approaches described herein, a robust immune response against the pathological tau protein can be generated with minimal risk of producing an adverse immune response towards the normal tau protein.

BRIEF DESCRIPTION OF THE DRAWINGS

FIG. 1A shows a robust IgG and IgM immune response in JNPL3 P301L mice immunized with Tau210-216[P-$Thr_{212}$-$Ser_{214}$] (SEQ ID NO: 2) linked to tetanus toxin helper T-cell epitope (TT947-967) via GPSL linker. FIG. 1B shows that a strong antibody response is generated against the tetanus toxin epitope as assessed by IgG and IgM binding to an unrelated tau epitope Tau260-264[P-$Ser_{262}$] linked via GPSL to TT947-967. ELISA plates were coated with 0.5 µg peptide per well and plasma was diluted 1:200.

FIG. 2A shows the IgG antibody response in mice following immunization with the Tau260-264[P-$Ser_{262}$] peptide. As above, the mice received the first two immunizations two weeks apart and then monthly thereafter from 2-3 months of age until 8-9 months of age. FIG. 2B shows that a good portion of the antibody response is generated against the tetanus toxin epitope as assessed by IgG binding to an unrelated tau epitope Tau210-216[P-$Thr_{212}$-$Ser_{214}$] linked via GPSL to TT947-967. FIG. 2C shows that a good portion of the antibody response is generated against the tau epitope as assessed by IgG binding to a larger tau epitope Tau240-270 [P-$Ser_{262}$] that contains the Tau260-264[P-$Ser_{262}$] region. ELISA plates were coated with 0.5 µg peptide per well and plasma was diluted 1:200. T0—Tfinal: Bleed prior to vaccination (T0), one week after third —(T1), sixth —(T2), seventh (T3) immunization, and at tissue harvesting (Tf).

As shown in FIG. 13A, a very strong titer was generated against the tau portion of the immunogen Tau-386-408[P-Ser$_{396,404}$] (red) as detected by serial dilutions of plasma. The plasma antibodies preferably recognized the phospho-Ser404 epitope (blue) and the non-phospho epitope (white). The phospho-Ser396 epitope (green) was recognized to a lesser degree. Numerous strongly positive clones were detected (>50). Of those, 8 phospho-specific clones were selected for a first subcloning (FIG. 13B). All appeared stable and three were selected for second subcloning (all IgG1). Of the clones that did not specifically recognize a phosphorylated-epitope, six were selected for first subcloning. All appeared stable and three were selected for second subcloning (IgG1, IgG2a and IgM).

As shown in FIG. 16A, a strong titer was generated against the immunogen Tau260-271[P-Ser$_{262}$] (purple), but plasma antibodies recognized the non-phospho peptide Tau260-271 as well (No-P; white). Eight stable phospho-specific clones were selected for further analysis (FIG. 16B).

FIG. 18D is a magnified image of the boxed region in FIG. 18A depicting neurons with aggregated tau. FIG. 18E is a higher magnified image of tangle-like pathology detected with 5F7D10 in a different JNPL3 P301L mouse.

DETAILED DESCRIPTION OF THE INVENTION

Figure 1A:
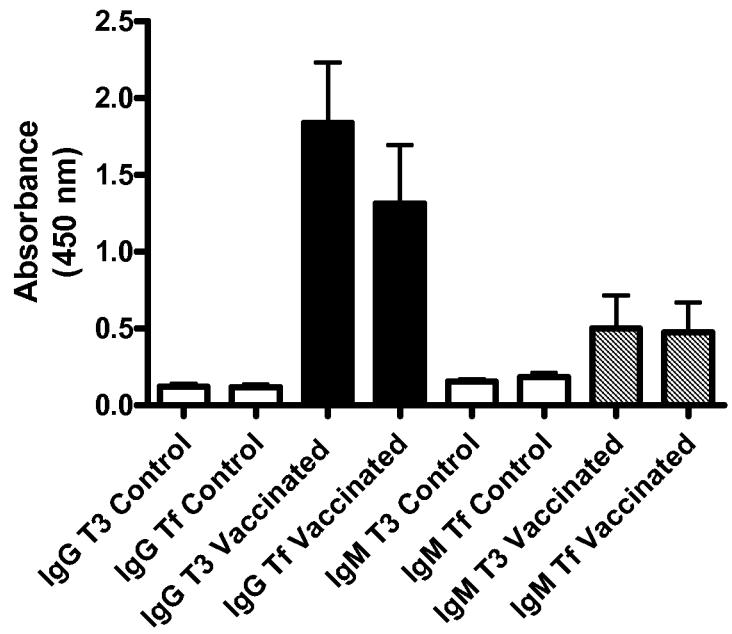
FIGS. 1A-1B depict the immune response in the JNPL3 P301L tangle mouse model to tau immunogenic peptides of the present invention. Mice of 2-3 months of age received the first two immunizations two weeks apart and then monthly thereafter. To assess antibody response, the mice were bled prior to the first immunization, periodically thereafter one week after vaccine administration, and when the mice were killed for tissue harvesting at 8-9 months of age. The IgG and IgM antibody response shown in FIGS. 1A and 1B was measured one week after the $6^{th}$ immunization (T3) and again at 8-9 months of age, which was at the time of sacrifice (Tf=Tfinal).

A first aspect of the present invention is directed to a method of preventing or treating Alzheimer's disease or other tauopathy in a subject. This method involves administering, to the subject, any one or more immunogenic tau peptides having an amino acid sequence selected from the group consisting of SEQ ID NOs: 2-75, or one or more antibodies recognizing an immunogenic tau epitope comprising an amino acid sequence selected from the group consisting of SEQ ID NO: 2-75 and 101-103 under conditions effective to treat or prevent Alzheimer's disease or other tauopathy in the subject.

As used herein a "tauopathy" encompasses any neurodegenerative disease that involves the pathological aggregation of the microtubule protein tau within the brain. Accordingly, in addition to both familial and sporadic Alzheimer's disease, other tauopathies that can be treated using the methods of the present invention include, without limitation, frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, and chronic traumatic encephalopathy.

Another aspect of the present invention is directed to a method of promoting clearance of tau aggregates from the brain of a subject. This method involves administering, to the subject, any one or more immunogenic tau peptides having an amino acid sequence selected from the group consisting of SEQ ID NOs: 2-75, or one or more antibodies recognizing an immunogenic tau epitope comprising an amino acid sequence selected from the group consisting of SEQ ID NOs: 2-75 and 101-103 under conditions effective to promote clearance of tau aggregates from the brain of the subject.

The clearance of tau aggregates includes clearance of neurofibrillary tangles and/or the pathological tau precursors to neurofibrillary tangles. Neurofibrillary tangles are often associated with neurodegenerative diseases including, for example, sporadic and familial Alzheimer's disease, amyotrophic lateral sclerosis, argyrophilic grain dementia, dementia pugilistica, chronic traumatic encephalopathy, diffuse neurofibrillary tangles with calcification, Down syndrome, Gerstmann-Straussler-Scheinker disease, Hallervorden-Spatz disease, hereditary frontotemporal dementia, parkinsonism linked to chromosome 17 (FTDP-17), inclusion body myositis, Creutsfeld-Jakob disease, multiple system atrophy, Niemann-Pick disease type C, Pick's disease, prion protein cerebral amyloid angiopathy, sporadic corticobasal degeneration, progressive supranuclear palsy, subacute sclerosing panencephalitis, myotonic dystrophy, motor neuron disease with neurofibrillary tangles, tangle only dementia, and progressive subcortical gliosis.

Another aspect of the present invention is directed to a method of slowing the progression of a tau-pathology related behavioral phenotype in a subject. This method involves administering, to the subject, any one or more immunogenic tau peptides comprising an amino acid sequence selected from the group consisting of SEQ ID NOs: 2-75, or one or more antibodies recognizing an immunogenic tau epitope comprising an amino acid sequence selected from the group consisting of SEQ ID NOs: 2-75 and 101-103, under conditions effective to slow the tau-pathology related behavioral phenotype in the subject.

As used herein, a tau-pathology related behavioral phenotype includes, without limitation, cognitive impairments, early personality change and disinhibition, apathy, abulia, mutism, apraxia, perseveration, stereotyped movements/behaviors, hyperorality, disorganization, inability to plan or organize sequential tasks, selfishness/callousness, antisocial traits, a lack of empathy, halting, agrammatic speech with frequent paraphasic errors but relatively preserved comprehension, impaired comprehension and word-finding deficits, slowly progressive gait instability, retropulsions, freezing, frequent falls, non-levodopa responsive axial rigidity, supranuclear gaze palsy, square wave jerks, slow vertical saccades, pseudobulbar palsy, limb apraxia, dystonia, cortical sensory loss, and tremor.

In accordance with the methods of the present invention, in one embodiment, an immunogenic tau peptide or a combination of immunogenic tau peptides are administered to a subject in need. Suitable immunogenic tau peptide fragments of the tau protein contain one or more antigenic epitopes that mimic the pathological form of the tau protein. Exemplary immunogenic tau epitopes are phosphorylated at one or more amino acids that are phosphorylated in the pathological form of tau, but not phosphorylated in the normal or non-pathological form of tau.

In a preferred embodiment of the present invention, administration of an immunogenic tau peptide induces an active immune response in the subject to the immunogenic tau peptide and to the pathological form of tau, thereby facilitating the clearance of related tau aggregates, slowing the progression of tau-pathology related behavior and treating the underlying tauopathy. In accordance with this aspect of the present invention, an immune response involves the development of a beneficial humoral (antibody mediated) and/or a cellular (mediated by antigen-specific T cells or their secretion products) response directed against the immunogenic tau peptide.

The presence of a humoral immunological response can be determined and monitored by testing a biological sample (e.g., blood, plasma, serum, urine, saliva feces, CSF or lymph fluid) from the subject for the presence of antibodies directed to the immunogenic tau peptide. Methods for detecting antibodies in a biological sample are well known in the art, e.g., ELISA, Dot blots, SDS-PAGE gels or ELISPOT. The presence of a cell-mediated immunological response can be determined by proliferation assays (CD4+ T cells) or CTL (cytotoxic T lymphocyte) assays which are readily known in the art.

Isolated immunogenic tau peptides of the present invention include any one of the amino acid sequences of SEQ ID NOs: 2-30 shown in Table 1 below. Amino acid residues of each sequence which are phosphorylated are shown in bold and marked with asterisks. The names of the peptides in Table 1 correspond to the amino acid position of these peptides within the longest isoform of the human tau protein having the amino acid sequence of SEQ ID NO:1 as shown below.

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
                115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser Ala Lys
225                 230                 235                 240
```

-continued

```
Ser Arg Leu Gln Thr Ala Pro Val Pro Met Pro Asp Leu Lys Asn Val
            245             250                 255

Lys Ser Lys Ile Gly Ser Thr Glu Asn Leu Lys His Gln Pro Gly Gly
            260             265                 270

Gly Lys Val Gln Ile Ile Asn Lys Lys Leu Asp Leu Ser Asn Val Gln
            275             280                 285

Ser Lys Cys Gly Ser Lys Asp Asn Ile Lys His Val Pro Gly Gly Gly
            290             295                 300

Ser Val Gln Ile Val Tyr Lys Pro Val Asp Leu Ser Lys Val Thr Ser
305             310             315                 320

Lys Cys Gly Ser Leu Gly Asn Ile His His Lys Pro Gly Gly Gly Gln
                325             330                 335

Val Glu Val Lys Ser Glu Lys Leu Asp Phe Lys Asp Arg Val Gln Ser
            340             345                 350

Lys Ile Gly Ser Leu Asp Asn Ile Thr His Val Pro Gly Gly Gly Asn
            355             360                 365

Lys Lys Ile Glu Thr His Lys Leu Thr Phe Arg Glu Asn Ala Lys Ala
            370             375                 380

Lys Thr Asp His Gly Ala Glu Ile Val Tyr Lys Ser Pro Val Val Ser
385             390             395                 400

Gly Asp Thr Ser Pro Arg His Leu Ser Asn Val Ser Ser Thr Gly Ser
            405             410                 415

Ile Asp Met Val Asp Ser Pro Gln Leu Ala Thr Leu Ala Asp Glu Val
            420             425                 430

Ser Ala Ser Leu Ala Lys Gln Gly Leu
            435             440
```

TABLE 1

Immunogenic Tau Peptides

| SEQ ID NO: | NAME | SEQUENCE |
|---|---|---|
| SEQ ID NO: 2 | Tau210-216 [P-Thr$_{212}$-Ser$_{214}$] | SRT*PS*LP |
| SEQ ID NO: 3 | Tau260-264 [P-Ser$_{262}$] | IGS*TE |
| SEQ ID NO: 4 | Tau229-237 [P-Thr$_{231}$-Ser$_{235}$] | VRT*PPKS*PS |
| SEQ ID NO: 5 | Tau394-406 [P-Ser$_{396,404}$] | YKS*PVVSGDTS*PR |
| SEQ ID NO: 6 | Tau192-221 [P-Thr$_{212}$Ser$_{214}$] | GDRSGYSSPGSPGTPGSRSRT*PS*LPTPPTR |
| SEQ ID NO: 7 | Tau192-221 [P-Ser$_{199,202,214}$, Thr$_{205,212}$] | GDRSGYSS*PGS*PGT*PGSRSRT*PS*LPTPPTR |
| SEQ ID NO: 8 | Tau192-221 [P-Ser$_{199,214}$ Thr$_{212,217}$] | GDRSGYSS*PGSPGTPGSRSRT*PS*LPT*PPTR |
| SEQ ID NO: 9 | Tau192-221 [P-Ser$_{202}$Thr$_{205}$] | GDRSGYSSPGS*PGT*PGSRSRTPSLPTPPTR |
| SEQ ID NO: 10 | Tau200-229 [P-Thr$_{212}$-Ser$_{214}$] | PGSPGTPGSRSRT*PS*LPTPPTREPKKVAVV |
| SEQ ID NO: 11 | Tau322-358 [P-Ser$_{324,356}$] | CGS*LGNIHHKPGGGQVIWKSEKLDFKDRVQSKIGS*LD |
| SEQ ID NO: 12 | Tau260-271 [P-Ser$_{262}$] | IGS*TENLKIIQPG |
| SEQ ID NO: 13 | Tau386-408 [P-Ser$_{396}$, Ser$_{404}$] | TDHGAEIVYKS*PVVSGDTS*PRHL |
| SEQ ID NO: 14 | Tau48-71 [P-Thr$_{50,69}$] | LQT*PTEDGSEEPGSETSDAKST*PT |

TABLE 1-continued

Immunogenic Tau Peptides

| SEQ ID NO: | NAME | | SEQUENCE |
|---|---|---|---|
| SEQ ID NO: 15 | Tau111-115 [P-Ser$_{113}$] | | TPS*LE |
| SEQ ID NO: 16 | Tau151-155 [P-Thr$_{153}$] | | IAT*PR |
| SEQ ID NO: 17 | Tau173-177 [P-Thr$_{175}$] | | AKT*PP |
| SEQ ID NO: 18 | Tau203-219 [P-Thr$_{205,212,217}$-Ser$_{208,210,214}$] | | PGT*PGS*RS*RT*PS*LPT*PP |
| SEQ ID NO: 19 | Tau233-237 [P-Thr$_{235}$] | | PKS*PS |
| SEQ ID NO: 20 | Tatt256-264 [P-Ser$_{258,262}$] | | VKS*KIGS*TE |
| SEQ ID NO: 21 | Tau287-291 [P-Ser$_{289}$] | | VQS*KC |
| SEQ ID NO: 22 | Tau354-358 [P-Ser$_{356}$] | | IGS*LD |
| SEQ ID NO: 23 | Tau398-416 [P-S$_{400,409,412,413}$-Thr$_{403,414}$] | | VVS*GDT*SPRFILS*NVS*S*T*GS |
| SEQ ID NO: 24 | Tau420-437 [P-Ser$_{422,433,435}$-Thr$_{427}$] | | VDS*PQLAT*LADEVS*AS*LA |
| SEQ 10 NO: 25 | Tau200-204 [P-Ser$_{202}$] | | PGS*P |
| SEQ ID NO: 26 | Tau203-207 [P-Thr$_{205}$] | | PGT*PG |
| SEQ ID NO: 27 | Tau197-207 [P-Ser$_{199,202}$-Thr$_{205}$] | | YSS*PGS*PGT*PG |
| SEQ ID NO: 28 | Tau206-216 [P-Thr$_{212}$-Ser$_{214}$] | | PGSRSRT*PS*LP |
| SEQ ID NO: 29 | Tau229-239 [P-Thr$_{231}$-Ser$_{235}$] | | VRT*PPKS*PSSA |
| SEQ ID NO: 30 | Tau179-188 [P-Thr$_{181}$-Ser$_{184,185}$] | | PKT*PPS*S*GEP |

Variants and analogs of the above immunogenic peptides that induce and/or crossreact with antibodies to the preferred epitopes of tau protein can also be used. Analogs, including allelic, species, and induced variants, typically differ from naturally occurring peptides at one, two, or a few positions, often by virtue of conservative substitutions. Analogs typically exhibit at least 80 or 90% sequence identity with natural peptides. Some analogs also include unnatural amino acids or modifications of N- or C-terminal amino acids at one, two, or a few positions.

In one embodiment of the present invention, variant immunogenic tau peptides are pseudo-phosphorylated peptides. The pseudo-phosphorylated peptides are generated by substituting one or more of the phosphorylated serine, threonine, and tyrosine residues of the tau peptides with acidic amino acid residues such as glutamic acid and aspartic acid (Huang et al., "Constitutive Activation of Mek1 by Mutation of Serine Phosphorylation Sites," Proc. Natl. Acad. Sci. USA 91(19):8960-3 (1994), which is hereby incorporated by reference in its entirety). Exemplary isolated immunogenic pseudo-phosphorylated tau peptides of the present invention are shown in Table 2 below. The position of the amino acid residue substitutions is indicated in each sequence of Table 2 with an "X", where X is an glutamic acid or aspartic acid residue substitution.

TABLE 2

Immunogenic Pseudo-Phosphorylated Tau Peptides

| SEQ ID NO: | NAME | SEQUENCE |
|---|---|---|
| SEQ ID NO: 31 | Tau210-216 [T212X, S214X] | SRXPXLP |
| SEQ ID NO: 32 | Tau260-264 [S262X] | IGXTE |
| SEQ ID NO: 33 | Tau229-237 [T231X, S235X] | VRXPPKXPS |
| SEQ ID NO: 34 | Tau394-406 [S396X, S404X] | YKXPVVSGDTXPR |
| SEQ ID NO: 35 | Tau192-221 [T212X, S214X] | GDRSGYSSPGSPGTPGSRSRXPXLPTPPTR |

TABLE 2-continued

Immunogenic Pseudo-Phosphorylated Tau Peptides

| SEQ ID NO: | NAME | SEQUENCE |
| --- | --- | --- |
| SEQ ID NO: 36 | Tau192-221 [S199X, S202X, S214X, T205X, T212X] | GDRSGYSXPGXPGXPGSRSRXPXLPTPPTR |
| SEQ ID NO: 37 | Tau192-221 [S199X, S214X, T212X, T217X] | GDRSGYSXPGSPGTPGSRSRXPXLPXPPTR |
| SEQ ID NO: 38 | Tau192-221 [S202X, T205X] | GDRSGYSSPGXPGXPGSRSRTPSLPTPPTR |
| SEQ ID NO: 39 | Tau200-229 [T212X,S214X] | PGSPGTPGSRSRXPXLPTPPTREPKKVAVV |
| SEQ ID NO: 40 | Tau322-358 [S324X, S356X] | CGXLGNIHHKPGGGQVEVKSEKLDFKDRVQ SKIGXLD |
| SEQ ID NO: 41 | Tau260-271 [S262X] | IGXTENLKHQPG |
| SEQ ID NO: 42 | Tau386-408 [S396X, S404X] | TDHGAEIVYKXPVVSGDTXPRHL |
| SEQ ID NO: 43 | Tau48-71 [T50X, T69X] | LQXPTEDGSEEPGSETSDAKSXPT |
| SEQ ID NO: 44 | Tau111-115 [S113X] | TPXLE |
| SEQ ID NO: 45 | Tau151-155 [T153X] | IAXPR |
| SEQ ID NO: 46 | Tau173-177 [T175X] | AKXPP |
| SEQ ID NO: 47 | Tau203-219 [T205X, T212X, T217X, S208X, S210X, S214X] | PGXPGXRXRXPXLPXPP |
| SEQ ID NO: 48 | Tau233-237 [T235X] | PKXPS |
| SEQ ID NO: 49 | Tau256-264 [S258X, S262X] | VKXKIGXTE |
| SEQ ID NO: 50 | Tau287-291 [S289X] | VQXKC |
| SEQ ID NO: 51 | Tau354-358 [S356X] | IGXLD |
| SEQ ID NO: 52 | Tau398-416 [S400X, S409X, S412X, S413X, T403X, T414X] | VVXGDXSPRHLXNVXXXGS |
| SEQ ID NO: 53 | Tau420-437 [S422X, S433X, S435X, T427X] | VDXPQLAXLADEVXAXLA |
| SEQ ID NO: 54 | Tau200-203 [S202X] | PGXP |
| SEQ ID NO: 55 | Tau203-207 [T205X] | PGXPG |
| SEQ ID NO: 56 | Tau133-162 [T149X, T153X] | DGTGSDDKKAKGADGKXKIAXTPRGAAPPGQ |
| SEQ ID NO: 57 | Tau379-408 [S396X, S404X] | RENAKAKTDHGAEIVYKXPVVSGDTXPRHL |
| SEQ ID NO: 58 | Tau192-221 [S199X, S202X, S214X, T205X, T212X] | GDRSGYSXPGXPGXPGSRSRXPXLPTPPTR |
| SEQ ID NO: 59 | Tau221-250 [T231X, S235X] | REPKKVAVVRXPPKXPSSAKSRLQTAPVPM |
| SEQ ID NO: 60 | Tau184-213 [S184X, S191X, Y197X, S198X, S199X, S202X, T205X, S208X, S210X, T212X] | XSGEPPKXGDRSQXXXPGXPGXPGXRXRX |
| SEQ ID NO: 61 | Tau1-30 [Y18X, Y29X] | MAEPRQEFEVMEDHAGTXGLGDRKDQGGXT |
| SEQ ID NO: 62 | Tau30-60 [T39X, S46X, T50X, T52X, S56X] | TMHQDQEGDXDAGLKEXPLQXPXEDGXEEPG |
| SEQ ID NO: 63 | Tau60-90 [S68X, T69X, T71X] | GSETSDAKXXPXAEDVTAPLVDEGAPGKQAA |

TABLE 2-continued

Immunogenic Pseudo-Phosphorylated Tau Peptides

| SEQ ID NO: | NAME | SEQUENCE |
|---|---|---|
| SEQ ID NO: 64 | Tau90-120 [T95X, T101X, T102X, T113X] | AAQPHXEIPEGXXAEEAGIGDTPXLEDEAAG |
| SEQ ID NO: 65 | Tau120-150 [T123X, S131X, T149X] | GHVXQARMVSKXKDGTGSDDKKAKGADGKXK |
| SEQ ID NO: 66 | Tau150-180 [T175X] | KIATPRGAAPPGQKGQANATRIPAKXPPAPK |
| SEQ ID NO: 67 | Tau180-210 [T181X, S184X, S185X, Y197X, S198X, S199X, S202X, T205X, S208X] | KXPPXXGEPPKSGDRSGXXXPGXPGXPGXRS |
| SEQ ID NO: 68 | Tau210-240 [T212X, S214X, T217X, T231X, S235X, S237X, S238X] | SRXPXLPXPPTREPKKVAVVRXPPKXPXXAK |
| SEQ ID NO: 69 | Tau240-270 [S262X] | KSRLQTAPVPMPDLKNVKSKIGXTENLKHQP |
| SEQ ID NO: 70 | Tau270-300 [S293X] | PGGGKVQIINKKLDLSNVQSKCGXKDNIKHV |
| SEQ ID NO: 71 | Tau300-330 [Y310, S324X] | VPGGGSVQIVXKPVDLSKVISKCGXLGNIFIH |
| SEQ ID NO: 72 | Tau330-360 [S356X] | HKPGGGQVEVKSEKLDFKDRVQSKIGXLDNI |
| SEQ ID NO: 73 | Tau360-390 [T361X, T373X, T386X] | IXHVPGGGNKKIEXHKLTFRENAKAKXDHGA |
| SEQ ID NO: 74 | Tau390-420 [Y394X, S396X, S400X, T403X, S404X, S409X, S412X, S413X] | AEIVXKXPVVXGDXXPRHLXNVXXIGSIDMV |
| SEQ ID NO: 75 | Tau411-441 [S412X, S413X, S422X] | VXXTGSIDMVDXPQLATLADEVSASLAKQGL |

Each tau peptide of the present invention, i.e., SEQ ID NOs: 2-75 and 87-88 (Table 3 below) is preferably acetylated on the N-terminus and amidated on the C-terminus to more closely resemble the same internal amino acids of the full length tau protein. The tau peptides of the present invention can also contain one or more D-amino acid residues to enhance the stability of the peptide. These D-amino acids can be in the same order as the L-form of the peptide or assembled in a reverse order from the L-form sequence to maintain the overall topology of the native sequence (Ben-Yedidia et al., "A Retro-Inverso Peptide Analogue of Influenza Virus Hemagglutinin B-cell Epitope 91-108 Induces a Strong Mucosal and Systemic Immune Response and Confers Protection in Mice after Intranasal Immunization," *Mol Immunol.* 39:323 (2002); Guichard, et al., "Antigenic Mimicry of Natural L-peptides with Retro-Inverso-Peptidomimetics," *PNAS* 91:9765-9769 (1994); Benkirane, et al., "Antigenicity and Immunogenicity of Modified Synthetic Peptides Containing D-Amino Acid Residues," *J. Bio. Chem.* 268(35):26279-26285 (1993), which are hereby incorporated by reference in their entirety).

Each of the above peptide sequences may be linked to an immunogenic carrier molecule to enhance its immunogenicity. Suitable immunogenic carrier molecules include, but are not limited to, helper T-cell epitopes, such as tetanus toxoid (e.g., the P2 and P30 epitopes), Hepatitis B surface antigen, cholera toxin B, toxoid, diphtheria toxoid, measles virus F protein, *Chlamydia trachomatis* major outer membrane protein, *Plasmodium falciparum* circumsporozite T, *P. falciparum* CS antigen, *Schistosoma mansoni* triose phosphate isomerase, *Bordetella pertussis*, *Clostridium tetani*, *Pertusaria trachythallina*, *Escherichia coli* TraT, and Influenza virus hemagluttinin (HA) (see U.S. Pat. No. 6,906,169 to Wang; U.S. Patent Application Publication No. 20030068325 to Wang, and WO/2002/096350 to Wang, which are hereby incorporated by reference in their entirety). In a preferred embodiment of the present invention, the T-helper cell epitope is the tetanus toxin 947-967 (P30) epitope having an amino acid sequence of FNNFTVSFWLRVPKVSASHLE (SEQ ID NO: 76). In another embodiment, the T-helper cell epitope is the tetanus toxin 830-843 (P2) epitope having an amino acid sequence of QYIKANSKFIGIT (SEQ ID NO: 77).

The immunogenic tau peptides of the present invention can be linked to the immunogenic carrier molecule using a short amino acid linker sequence. In a preferred embodiment of the present invention, a GPSL (SEQ ID NO: 78) linker sequence is used to link the immunogenic tau peptide to the immunogenic carrier molecule. Other suitable linker sequences include glycine-rich (e.g. $G_{3-5}$) or serine-rich (e.g., GSG, GSGS (SEQ ID NO: 79), GSGSG (SEQ ID NO: 80), $GS_NG$) linker sequences or flexible immunoglobulin linkers as disclosed in. U.S. Pat. No. 5,516,637 to Huang et al, which is hereby incorporated by reference in its entirety.

Alternatively, the immunogenic tau peptides of the present invention can be linked to the immunogenic carrier molecule using chemical crosslinking. Techniques for linking a peptide immunogen to an immunogenic carrier molecule include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine residues on one protein, and an amide linkage through the epsilon-amino on a lysine, or other free amino group in other amino acids. A variety of such disulfide/amide-forming agents are described by Jansen et al., "Immunotoxins: Hybrid Molecules Combining High Specificity and Potent Cytotoxicity," Immun Rev 62:185-216 (1982), which is incorporated by reference in its entirety. Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt.

Immunogenic tau peptides of the present invention can be synthesized by solid phase peptide synthesis or recombinant expression systems. Automatic peptide synthesizers are commercially available from numerous suppliers, such as Applied Biosystems (Foster City, Calif.). Recombinant expression systems can include bacteria, such as *E. coli*, yeast, insect cells, or mammalian cells. Procedures for recombinant expression are described by Sambrook et al., *Molecular Cloning: A Laboratory Manual* (C.S.H.P. Press, NY 2d ed., 1989), which is hereby incorporated by reference in its entirety.

The immunogenic tau peptides of the present invention can be administered alone or in combination with other immunogenic tau peptides of the present invention to a subject in need. In one embodiment, an immunogenic tau peptide of the present invention is administered in combination with one or more immunogenic tau peptides shown in Table 3 below as disclosed in U.S. Patent Application Publication No. 20080050383 to Sigurdsson, which is hereby incorporated by reference in its entirety. The names of the peptides in Table 3 correspond to the amino acid position of these peptides within the longest isoform of the tau protein having the amino acid sequence of SEQ ID NO:1. Amino acid residues of each sequence which are phosphorylated are shown in bold and marked with asterisks.

TABLE 3

Immunogenic Tau Peptide Sequences for Combined Administration

| SEQ ID NO: | NAME | SEQUENCE |
|---|---|---|
| SEQ ID NO: 81 | Tau133-162 | DGTGSDDKKAKGADGKTKIATPRGAAPPGQ |
| SEQ ID NO: 82 | Tau379-408 [P-Ser$_{396,404}$] | RENAKAKTDHGAEIVYKS*PVVSGDTS*PRHL |
| SEQ ID NO: 83 | Tau192-221 [P-Ser$_{199,202,214}$.-Thr$_{205,212}$] | GDRSGYSS*PGS*PGT*PGSRSRT*PS*LPTPPTR |
| SEQ ID NO: 84 | Tau221-250 [P-Thr$_{231}$.-Ser$_{235}$] | REPKKVAVVRT*PPKS*PSSAKSRLQTAPVPM |
| SEQ ID NO: 85 | Tau184-213 | SSGEPPKSGDRSQYSSPGSPGTPGSRSRT |
| SEQ ID NO: 86 | Tau1-30 [P-Tyr$_{18,29}$] | MAEPRQEFEVMEDHAGTY*GLGDRKDQGGY*T |
| SEQ ID NO: 87 | Tau30-60 | TMHQDQEGDTDAGLKESPLQTPTEDOSEEPG |
| SEQ ID NO: 88 | Tau60-90 | GSETSDAKSTPTAEDVTAPLVDEGAPGKQAA |
| SEQ ID NO: 89 | Tau90-120 | AAQPHTEIPFGTTAEEAGIGDTPSLEDEAAG |
| SEQ ID NO: 90 | Tau120-150 | GHVTQARMVSKSKDGTGSDDKKAKGADGKTK |
| SEQ ID NO: 91 | Tau150-180 [P-Thr$_{175}$] | KIATPRGAAPPGQKGQANATRIPAKT*PPAPK |
| SEQ ID NO: 92 | Tau180-210 [P-Thr$_{181,205}$,-Ser$_{184,185,198,199,202,208}$,-Tyr$_{197}$] | KT*PPS*S*GEPPKSGDRSGV*S*S*PGS*PGT*PGS*RS |
| SEQ ID NO: 93 | Tau210-240 [P-Thr$_{212,217,231}$,-Ser$_{214,235,237,238}$] | SRT*PS*LPT*PPTREPKKVAVVRT*PPKS*PS*S*AK |
| SEQ ID NO: 94 | Tau240-270 [P-Ser$_{262}$] | KSRLQTAPVPMPDLKNVKSKIGS*TENLKHQP |
| SEQ ID NO: 95 | Tau270-300 [P-Ser$_{293}$] | PGGGKVQIINKKEDLSNVQSKCGS*KDNIKHV |
| SEQ ID NO: 96 | Tau300-330 [P-Tyr$_{310}$, Ser$_{324}$] | VPGGGSVQIVY*KPVDLSKVTSKCGS*LGNIHH |
| SEQ ID NO: 97 | Tau330-360 [P-Ser$_{356}$] | HKPGGGQVEVKSEKLDEKDRVQSKICS*LDNI |
| SEQ ID NO: 98 | Tau360-390 | ITHVPGGGNKKIETHKLTFRENAKAKTDHGA |
| SEQ ID NO: 99 | Tau390-420 [P-Tyr$_{394}$, Ser$_{396,400,404,409,412,413}$, Thr$_{403}$] | AEIVY*KS*PVVS*GDT*S*PRHLS*NVS*S*TGSIDMV |
| SEQ ID NO: 100 | Tau411-441 [P-Ser$_{412,413,422}$] | VS*S*TGSIDMVDS*PQLATLADEVSASLAKQGL |

The immunogenic tau peptides of the present invention can be administered in combination with a suitable adjuvant to achieve the desired immune response in the subject. Suitable adjuvants can be administered before, after, or concurrent with administration of the immunogenic tau peptide of the present invention. Preferred adjuvants augment the intrinsic response to an immunogen without causing conformational changes in the immunogen that affect the qualitative form of the response.

A preferred class of adjuvants is the aluminum salts (alum), such as aluminum hydroxide, aluminum phosphate, and aluminum sulfate. Such adjuvants can be used with or without other specific immunostimulating agents, such as 3 De-O-acylated monophosphoryl lipid A (MPL) or 3-DMP, polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) theramide™), or other bacterial cell wall components. Oil-in-water emulsions include MF59 (see WO 90/14837 to Van Nest et al., which is hereby incorporated by reference in its entirety), containing 5% Squalene, 0.5% Tween 80, and 0.5% Span 85 (optionally containing various amounts of MTP-PE) formulated into submicron particles using a microfluidizer; SAF, containing 10% Squalene, 0.4% Tween 80, 5% pluronic-blocked polymer L121, and thr-MDP, either microfluidized into a submicron emulsion or vortexed to generate a larger particle size emulsion; and the Ribi™ adjuvant system (RAS) (Ribi ImmunoChem, Hamilton, Mont.) containing 2% squalene, 0.2% Tween 80, and one or more bacterial cell wall components selected from the group consisting of monophosphoryllipid A (MPL), trehalose dimycolate (TDM), and cell wall skeleton (CWS), preferably MPL+CWS (Detox™). Other adjuvants include Complete Freund's Adjuvant (CFA), Incomplete Freund's Adjuvant (IFA), and cytokines, such as interleukins (IL-1, IL-2, and IL-12), macrophage colony stimulating factor (M-CSF), and tumor necrosis factor (TNF).

The choice of an adjuvant depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, alum, MPL or Incomplete Freund's adjuvant (Chang et al., *Advanced Drug Delivery Reviews* 32:173-186 (1998), which is hereby incorporated by reference in its entirety) alone or optionally all combinations thereof are suitable for human administration.

Another aspect of the present invention relates to a pharmaceutical composition containing one or more of the immunogenic tau peptides described supra and a pharmaceutical carrier (describe infra). The pharmaceutical composition may contain a mixture of the same immunogenic tau peptide. Alternatively, the pharmaceutical composition contains a mixture of one or more different immunogenic tau peptides of the present invention. In a preferred embodiment, pharmaceutical compositions of the present invention contain one or more suitable adjuvants as described supra.

In another embodiment of the present invention, an antibody recognizing one or more of the immunogenic tau epitopes of the present invention is administered to a subject in need. Suitable antibodies of the present invention encompass any immunoglobulin molecule that specifically binds to an immunogenic tau epitope comprising any one of amino acid sequences of SEQ ID NOs: 2-75 and 101-103. In a preferred embodiment, an antibody of the present invention recognizes and binds to an epitope specific for the pathological form of tau and has little to no crossreactivity with the normal tau protein or a non-tau protein.

As described herein, monoclonal antibodies recognizing the immunogenic tau epitopes comprising SEQ ID NO:13 (Tau 386-408 [P-Ser$_{396,404}$]) and SEQ ID NO:12 (Tau 260-271[P-Ser$_{262}$]) have been generated. These antibodies are phospho-specific and, therefore, specific for the pathological tau forms having little to no crossreactivity to the normal tau protein.

In addition to the antibodies recognizing phosphorylated pathological epitopes of the tau protein, the present invention is also directed to antibodies that preferentially recognize pathological tau fragments involved in promoting neuronal toxicity and/or seeding tau aggregation. For example, caspase cleavage of tau, preferentially at aspartate residue 421 (D421) of the tau protein, creates a truncated molecule that colocalizes with tangles and correlates with the progression in Alzheimer's disease and in animal models of tauopathy (see Calignon et al., "Caspase Activation Precedes and Leads to Tangles," *Nature* 464:1201-1205 (2010), which is hereby incorporated by reference in its entirety). An antibody directed to the free D421 end of the cleaved tau protein would be specific for, and facilitate the removal of, pathological tau but not normal tau. Accordingly, the present invention is directed to an antibody, preferably a monoclonal antibody, directed to D421 on the free C-terminus of a cleaved pathological tau protein, that is not present in the normal tau protein. In one embodiment of the present invention, the antibody is generated using the methods described herein with an immunogenic tau peptide comprising an amino acid sequence of HLSNVSSTGSIDMVD (SEQ ID NO:101).

Truncation of tau at glutamic acid residue 391 (E391) is also associated with neurofibrillary tangle formation in the brains of Alzheimer's disease patients (Basurto-Islas et al., "Accumulation of Aspartic Acid$^{421}$—and Glutamic Acid$^{391}$—Cleaved Tau in Neurofibrillary Tangles Correlates with Progression in Alzheimer Disease," *J Neuropathol Exp Neurol* 67:470-483 (2008), which is hereby incorporated by reference in its entirety). Accordingly, the present invention is also directed to an antibody, preferably a monoclonal antibody, directed to E391 on the free C-terminus of a cleaved pathological tau protein, that is not present in the normal tau protein. In one embodiment of the present invention, the antibody is generated using the methods described herein with an immunogenic tau peptide comprising an amino acid sequence of RENAKAKTDHGAE (SEQ ID NO:102)

Calpain-1 also mediates the cleavage of tau, generating a toxic 17kDa tau fragment that promotes Aβ-induced neurotoxicity (Park et al., "The Generation of a 17kDa Neurotoxic Fragment: An Alternative Mechanism by which Tau Mediates β-Amyloid-Induced Neurodegeneration," *J Neurosci* 25(22):5365-75 (2005), which is hereby incorporated by reference in its entirety). Accordingly, an embodiment of the present invention is also directed to an antibody, preferably a monoclonal antibody, specifically recognizing the free N- and/or free C-terminus of this toxic tau fragment, but not the normal tau protein, comprising amino acid residues 45-230 of tau (SEQ ID NO:1) shown as SEQ ID NO:103 below.

```
Glu Ser Pro Leu Gln Thr Pro Thr Glu Asp Gly Ser Glu Glu Pro Gly
1               5               10              15

Ser Glu Thr Ser Asp Ala Lys Ser Thr Pro Thr Ala Glu Asp Val Thr
            20              25              30

Ala Pro Leu Val Asp Glu Gly Ala Pro Gly Lys Gln Ala Ala Ala Gln
            35              40              45

Pro His Thr Glu Ile Pro Glu Gly Thr Thr Ala Glu Glu Ala Gly Ile
        50              55              60

Gly Asp Thr Pro Ser Leu Glu Asp Glu Ala Ala Gly His Val Thr Gln
65                  70              75                      80

Ala Arg Met Val Ser Lys Ser Lys Asp Gly Thr Gly Ser Asp Asp Lys
                85              90                      95

Lys Ala Lys Gly Ala Asp Gly Lys Thr Lys Ile Ala Thr Pro Arg Gly
            100             105             110

Ala Ala Pro Pro Gly Gln Lys Gly Gln Ala Asn Ala Thr Arg Ile Pro
        115             120             125

Ala Lys Thr Pro Pro Ala Pro Lys Thr Pro Pro Ser Ser Gly Glu Pro
    130             135             140

Pro Lys Ser Gly Asp Arg Ser Gly Tyr Ser Ser Pro Gly Ser Pro Gly
145             150             155             160

Thr Pro Gly Ser Arg Ser Arg Thr Pro Ser Leu Pro Thr Pro Pro Thr
                165             170             175

Arg Glu Pro Lys Lys Val Ala Val Val Arg
            180             185
```

As used herein, the term "antibody" includes intact immunoglobulins derived from natural sources or from recombinant sources, as well as immunoreactive portions (i.e., antigen binding portions) of intact immunoglobulins. The antibodies of the present invention may exist in a variety of forms including, for example, polyclonal antibodies, monoclonal antibodies, intracellular antibodies ("intrabodies"), antibody fragments (e.g., Fv, Fab and F(ab)2), as well as single chain antibodies (scFv), chimeric antibodies and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli.*" *Proc Natl Acad Sci USA* 85:5879-5883 (1988); Bird et al, "Single-Chain Antigen-Binding Proteins," *Science* 242:423-426 (1988)).

Methods for monoclonal antibody production may be carried out using the techniques described herein or others well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with the antigen of interest (i.e., an immunogenic tau peptide) either in vivo or in vitro. Exemplary tau peptides are described supra. For generating monoclonal antibodies using the tau peptides of SEQ ID NOs: 2-75 or tau peptides of SEQ ID NOs: 101-103, a cysteine residue may be added to the N- or C-terminus of each sequence to facilitate linkage of a carrier protein that will enhance antibody production upon immunization. Suitable carrier proteins include, without limitation keyhole limpet hemocyanine, blue carrier immunogenic protein (derived from *Concholepas concholepas*), bovine serum albumin (BSA), ovalbumin, and cationized BSA.

The antibody-secreting lymphocytes are fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur. J Immunol* 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

Alternatively, monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries (McCafferty et al., "Phage Antibodies: Filamentous Phage Displaying Antibody Variable Domains," *Nature* 348: 552-554 (1990); Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J. Mol. Biol.* 222:581-597 (1991), which are hereby incorporated by reference in their entirety).

The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

The monoclonal antibody of the present invention can be a humanized antibody. Humanized antibodies are antibodies that contain minimal sequences from non-human (e.g. murine) antibodies within the variable regions. Such antibodies are used therapeutically to reduce antigenicity and human anti-mouse antibody responses when administered to a human subject.

An antibody can be humanized by substituting the complementarity determining region (CDR) of a human antibody with that of a non-human antibody (e.g. mouse, rat, rabbit, hamster, etc.) having the desired specificity, affinity, and capability (Jones et al., "Replacing the Complementarity-Determining Regions in a Human Antibody With Those From a Mouse," *Nature* 321:522-525 (1986); Riechmann et al., "Reshaping Human Antibodies for Therapy," *Nature* 332:323-327 (1988); Verhoeyen et al., "Reshaping Human Antibodies: Grafting an Antilysozyme Activity," *Science* 239:1534-1536 (1988), which are hereby incorporated by reference in their entirety). The humanized antibody can be further modified by the substitution of additional residues either in the Fv framework region and/or within the replaced non-human residues to refine and optimize antibody specificity, affinity, and/or capability.

Human antibodies can be produced using various techniques known in the art. Immortalized human B lymphocytes immunized in vitro or isolated from an immunized individual that produce an antibody directed against a target antigen can be generated (See e.g. Reisfeld et al., MONOCLONAL ANTIBODIES AND CANCER THERAPY 77 (Alan R. Liss ed., 1985) and U.S. Pat. No. 5,750,373 to Garrard, which are hereby incorporated by reference in their entirety). Alternatively, the human antibody can be selected from a phage library, where that phage library expresses human antibodies (Vaughan et al., "Human Antibodies with Sub-Nanomolar Affinities Isolated from a Large Non-immunized Phage Display Library," *Nature Biotechnology*, 14:309-314 (1996); Sheets et al., "Efficient Construction of a Large Nonimmune Phage Antibody Library: The Production of High-Affinity Human Single-Chain Antibodies to Protein Antigens," *Proc. Natl. Acad. Sci. U.S.A.* 95:6157-6162 (1998); Hoogenboom et al., "By-passing Immunization. Human Antibodies From Synthetic Repertoires of Germline VH Gene Segments Rearranged In Vitro," *J Mol Biol* 227:381-8 (1992); Marks et al., "By-passing Immunization. Human Antibodies from V-gene Libraries Displayed on Phage," *J Mol Biol* 222:581-97 (1991), which are hereby incorporated by reference in their entirety). Human antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807 to Surani et al.; U.S. Pat. No. 5,545,806 to Lonberg et al.; U.S. Pat. No. 5,569,825 to Lonberg et al.; U.S. Pat. No. 5,625,126 to Lonberg et al.; U.S. Pat. No. 5,633,425 to Lonberg et al.; and U.S. Pat. No. 5,661,016 to Lonberg et al., which are hereby incorporated by reference in their entirety Procedures for raising polyclonal antibodies are also well known in the art. Typically, such antibodies can be raised by administering the peptide containing the epitope of interest (i.e. any tau peptide selected from the group consisting of SEQ ID NOs: 2-75 or SEQ ID NOs: 101-103) subcutaneously to New Zealand white rabbits which have been bled to obtain pre-immune serum. The antigens can be injected in combination with an adjuvant. The rabbits are bled approximately every two weeks after the first injection and periodically boosted with the same antigen three times every six weeks. Polyclonal antibodies are recovered from the serum by affinity chromatography using the corresponding antigen to capture the antibody. This and other procedures for raising polyclonal antibodies are disclosed in Ed Harlow and David Lane, USING ANTIBODIES: A LABORATORY MANUAL (Cold Spring Harbor Laboratory Press, 1988), which is hereby incorporated by reference in its entirety.

In addition to whole antibodies, the present invention encompasses binding portions of such antibodies. Such binding portions include the monovalent Fab fragments, Fv fragments (e.g., single-chain antibody, scFv), and single variable $V_H$ and $V_L$ domains, and the bivalent F(ab')$_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES:PRINCIPLES AND PRACTICE 98-118 (Academic Press, 1983) and Ed Harlow and David Lane, ANTIBODIES: A LABORATORY MANUAL (Cold Spring Harbor Laboratory, 1988), which are hereby incorporated by reference in their entirety, or other methods known in the art.

Also suitable for use in the present invention are antibody fragments engineered to bind to intracellular proteins, i.e. intrabodies. Intrabodies directed to an immunogenic tau epitope comprising any one of SEQ ID NOs: 2-75 of SEQ ID NOs: 101-103 can prevent pathological tau aggregation and accumulation within neurons or glial cells and/or facilitate aggregate clearance. The application of intrabody technology for the treatment of neurological disorders, including tauopathies, is reviewed in Miller et al., "Intrabody Applications in Neurological Disorders: Progress and Future Prospects," *Mol Therapy* 12:394-401 (2005), which is hereby incorporated by reference in its entirety.

Intrabodies are generally obtained by selecting a single variable domain from variable regions of an antibody having two variable domains (i.e., a heterodimer of a heavy chain variable domain and a light chain variable domain). Single chain Fv fragments, Fab fragments, ScFv-Ck fusion proteins, single chain diabodies, $V_H$-$C_H$1 fragments, and even whole IgG molecules are suitable formats for intrabody development (Kontermann R. E., "Intrabodies as Therapeutic Agents," *Methods* 34:163-70 (2004), which is here by incorporated by reference in its entirety).

Intrabodies having antigen specificity for a pathological tau protein epitope can be obtained from phage display, yeast surface display, or ribosome surface display. Methods for producing libraries of intrabodies and isolating intrabodies of interest are further described in U.S. Published Patent Application No. 20030104402 to Zauderer and U.S. Published Patent Application No. 20050276800 to Rabbitts, which are hereby incorporated by reference in their entirety. Methods for improving the stability and affinity binding characteristics of intrabodies are described in WO2008070363 to Zhenping and Contreras-Martinez et al., "Intracellular Ribosome Display via SecM Translation Arrest as a Selection for Antibodies with Enhanced Cytosolic Stability," *J Mol Biol* 372(2):513-24 (2007), which are hereby incorporated by reference in their entirety.

It may further be desirable, especially in the case of antibody fragments, to modify the antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Antibody mimics are also suitable for use in accordance with the present invention. A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," *J Mol Biol* 284:1141-1151 (1998); Koide et al., "Probing Protein Conformational Changes in Living Cells by Using Designer Binding Proteins: Application to the Estrogen Receptor," *Proc Natl Acad Sci USA* 99:1253-1258 (2002), each of which is hereby incorporated by reference in its entirety), and those known as affibodies, which are derived from the stable alpha-helical bacterial receptor domain Z of staphylococcal protein A (Nord et al., "Binding Proteins Selected from Combinatorial Libraries of an alpha-helical Bacterial Receptor Domain," *Nature Biotechnol* 15(8):772-777 (1997), which is hereby incorporated by reference in its entirety).

The present invention is further directed to pharmaceutical compositions containing the one or more antibodies recognizing the immunogenic tau peptides of the present invention as described supra. This pharmaceutical composition may contain a mixture of the same antibodies recognizing the same tau epitope. Alternatively, the pharmaceutical composition may contain a mixture of one or more antibodies recognizing one or more different tau epitopes. The pharmaceutical composition of the present invention further contains a pharmaceutically acceptable carrier or other pharmaceutically acceptable components as described infra.

The pharmaceutical compositions of the present invention containing the immunogenic tau peptides or antibodies recognizing the immunogenic tau peptides, contain, in addition to the active therapeutic agent, a variety of other pharmaceutically acceptable components (see *Remington's Pharmaceutical Science* (15th ed., Mack Publishing Company, Easton, Pa., 1980), which is hereby incorporated by reference in its entirety). The preferred formulation of the pharmaceutical composition depends on the intended mode of administration and therapeutic application. The compositions can include pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, non-immunogenic stabilizers, and the like.

Pharmaceutical compositions can also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes). Additionally, these carriers can function as immunostimulating agents (i.e., adjuvants).

The pharmaceutical compositions of the present invention can further include a suitable delivery vehicle. Suitable delivery vehicles include, but are not limited to viruses, bacteria, biodegradable microspheres, microparticles, nanoparticles, liposomes, collagen minipellets, and cochleates.

In one embodiment of the present invention, the delivery vehicle is a virus or bacteria and the immunogenic tau peptide is presented by a virus or bacteria as part of an immunogenic composition. In accordance with this embodiment of the invention, a nucleic acid molecule encoding the immunogenic peptide is incorporated into a genome or episome of the virus or bacteria. Optionally, the nucleic acid molecule is incorporated in such a manner that the immunogenic peptide is expressed as a secreted protein or as a fusion protein with an outer surface protein of a virus or a transmembrane protein of bacteria so that the peptide is displayed. Viruses or bacteria used in such methods should be nonpathogenic or attenuated. Suitable viruses include adenovirus, HSV, Venezuelan equine encephalitis virus and other alpha viruses, vesicular stomatitis virus, and other rhabdo viruses, vaccinia and fowl pox. Suitable bacteria include *Salmonella* and *Shigella*. Fusion of an immunogenic peptide to HBsAg of HBV is particularly suitable.

In another embodiment of the present invention, the pharmaceutical composition contains a liposome delivery vehicle. Liposomes are vesicles comprised of one or more concentrically ordered lipid bilayers which encapsulate an aqueous phase. An immunogenic tau peptide or antibody raised against an immunogenic tau peptide of the present invention can be surface bound, encapsulated, or associated with the membrane of the liposome vehicle. Various types of liposomes suitable for vaccine delivery of the tau peptides are known in the art (see e.g., Hayashi et al., "A Novel Vaccine Delivery System Using Immunopotentiating Fusogenic Liposomes," *Biochem Biophys Res Commun* 261(3): 824-28 (1999) and U.S. Patent Publication No. 20070082043 to Michaeli et al., which are hereby incorporated by reference in their entirety). Other methods for preparing liposomes for use in the present invention include those disclosed in Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al., which are hereby incorporated by reference in their entirety.

In another embodiment of the present invention, a nucleic acid molecule encoding an immunogenic tau peptide or a tau antibody of the present invention is administered using a gene therapy delivery system. Suitable gene therapy vectors include, without limitation, adenoviral vectors, adeno-associated viral vectors, retroviral vectors, lentiviral vectors, and herpes viral vectors.

Adenoviral viral vector delivery vehicles can be readily prepared and utilized as described in Berkner, "Development of Adenovirus Vectors for the Expression of Heterologous Genes," *Biotechniques* 6:616-627 (1988) and Rosenfeld et al., "Adenovirus-Mediated Transfer of a Recombinant Alpha 1-Antitrypsin Gene to the Lung Epithelium In Vivo," *Science* 252:431-434 (1991), WO 93/07283 to Curiel et al., WO 93/06223 to Perricaudet et al., and WO 93/07282 to Curiel et al., which are hereby incorporated by reference in their entirety. Adeno-associated viral delivery vehicles can be constructed and used to deliver a nucleic acid encoding a tau antibody of the present invention to cells as described in Shi et al., "Therapeutic Expression of an Anti-Death Receptor-5 Single-Chain Fixed Variable Region Prevents Tumor Growth in Mice," *Cancer Res.* 66:11946-53 (2006); Fukuchi et al., "Anti-Aβ Single-Chain Antibody Delivery via Adeno-Associated Virus for Treatment of Alzheimer's Disease," *Neurobiol. Dis.* 23:502-511 (2006); Chatterjee et al., "Dual-Target Inhibition of HIV-1 In Vitro by Means of an Adeno-Associated Virus Antisense Vector," *Science* 258:1485-1488 (1992); Ponnazhagan et al., "Suppression of Human Alpha-Globin Gene Expression Mediated by the Recombinant Adeno-Associated Virus 2-Based Antisense Vectors," *J. Exp. Med.* 179:733-738 (1994); and Zhou et al., "Adeno-associated Virus 2-Mediated Transduction and Erythroid Cell-Specific Expression of a Human Beta-Globin Gene," *Gene Ther.* 3:223-229 (1996), which are hereby incorporated by reference in their entirety. In vivo use of these vehicles is described in Flotte et al., "Stable in Vivo Expression of the Cystic Fibrosis Transmembrane Conductance Regulator With an Adeno-Associated Virus Vector," *Proc. Nat'l. Acad. Sci.* 90:10613-10617 (1993) and Kaplitt et al., "Long-Term Gene Expression and Phenotypic Correction Using Adeno-Associated Virus Vectors in the Mammalian Brain," *Nature Genet.* 8:148-153 (1994), which are hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, which are hereby incorporated by reference in their entirety.

Retroviral vectors which have been modified to form infective transformation systems can also be used to deliver nucleic acid molecules encoding a desired peptide or antibody to a target cell. One such type of retroviral vector is disclosed in U.S. Pat. No. 5,849,586 to Kriegler et al., which is hereby incorporated by reference.

Gene therapy vectors carrying a nucleic acid molecule encoding the immunogenic tau peptide or tau antibody are administered to a subject by, for example, intravenous injection, local administration (U.S. Pat. No. 5,328,470 to Nabel et al., which is hereby incorporated by reference in its entirety) or by stereotactic injection (see e.g., Chen et al., "Gene Therapy for Brain Tumors: Regression of Experimental Gliomas by Adenovirus Mediated Gene Transfer In Vivo," *Proc. Nat'l. Acad. Sci. USA* 91:3054-3057 (1994), which is hereby incorporated by reference in its entirety). The pharmaceutical preparation of the gene therapy vector can include the gene therapy vector in an acceptable diluent, or can comprise a slow release matrix in which the gene delivery vehicle is imbedded.

In carrying out the methods of the present invention, it is preferable to select a subject having or at risk of having Alzheimer's disease or other tauopathy, a subject having tau aggregates in the brain, or a subject exhibiting a tangle related behavioral phenotype prior to administering the immunogenic peptides or antibodies of the present invention. Subjects amenable to treatment include individuals at risk of disease but not showing symptoms, as well as patients presently showing symptoms. In the case of Alzheimer's disease, virtually anyone is at risk of suffering from Alzheimer's disease. Therefore, the present methods can be administered prophylactically to the general population without the need for any assessment of the risk of the subject patient. The present methods are especially useful for individuals who do have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations, respectively. Other markers of risk include mutations in the presenilin genes, PS1 and PS2, and ApoE4 gene, a family history of AD, and hypercholesterolemia or atherosclerosis. Individuals presently suffering from Alzheimer's disease can be recognized from characteristic dementia by the presence of risk factors described above. In addition, a number of diagnostic tests are available for identifying individuals who have AD. These include measurement of CSF tau and Aβ42 levels. Elevated tau and decreased Aβ42 levels signify the presence of AD. Individuals suffering from Alzheimer's disease can also be diagnosed by Alzheimer's Disease and Related Disorders Association criteria.

In asymptomatic patients, treatment can begin at any age (e.g., 10, 20, 30 years of age). Usually, however, it is not necessary to begin treatment until a patient reaches 40, 50, 60, or 70 years of age. Treatment typically entails multiple dosages over a period of time. Treatment can be monitored by assaying antibody, or activated T-cell or B-cell responses to the therapeutic agent over time. If the response falls, a booster dosage is indicated. In the case of potential Down's syndrome patients, treatment can begin antenatally by administering therapeutic agent to the mother or shortly after birth.

In prophylactic applications, pharmaceutical compositions containing the immunogenic tau peptides are administered to a patient susceptible to, or otherwise at risk of, Alzheimer's disease or other tauopathy in an amount sufficient to eliminate or reduce the risk, lessen the severity, or delay the outset of the disease, including biochemical, histologic and/or behavioral symptoms of the disease, its complications and intermediate pathological phenotypes presented during development of the disease. In therapeutic applications, compositions containing a tau antibody are administered to a patient suspected of, or already suffering from, such a disease in an amount sufficient to cure, or at least partially arrest, the symptoms of the disease (biochemical, histologic and/or behavioral), including its complications and intermediate pathological phenotypes in development of the disease. In some methods, administration of agent reduces or eliminates mild cognitive impairment in patients that have not yet developed characteristic Alzheimer's pathology. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. Typically, the immune response is monitored and repeated dosages are given if the immune response starts to wane.

Effective doses of the compositions of the present invention, for the treatment of the above described conditions vary depending upon many different factors, including mode of administration, target site, physiological state of the patient, other medications administered, and whether treatment is prophylactic or therapeutic. Treatment dosages need to be titrated to optimize safety and efficacy. The amount of immunogen depends on whether adjuvant is also administered, with higher dosages being required in the absence of adjuvant. The amount of an immunogen for administration sometimes varies from 1-500 µg per patient and more usually from 5-500 µg per injection for human administration. Occasionally, a higher dose of 1-2 mg per injection is used. Typically about 10, 20, 50, or 100 µg is used for each human injection. The mass of immunogen also depends on the mass ratio of immunogenic epitope within the immunogen to the mass of immunogen as a whole. Typically, $10^{-3}$ to $10^{-5}$ micromoles of immunogenic epitope are used for each microgram of immunogen. The timing of injections can vary significantly from once a day, to once a year, to once a decade. On any given day that a dosage of immunogen is given, the dosage is greater than 1 µg/patient and usually greater than 10 µg/patient if adjuvant is also administered, and greater than 10 µg/patient and usually greater than 100 µg/patient in the absence of adjuvant. A typical regimen consists of an immunization followed by booster injections at time intervals, such as 6 week intervals. Another regimen consists of an immunization followed by booster injections 1, 2, and 12 months later. Another regimen entails an injection every two months for life. Alternatively, booster injections can be on an irregular basis as indicated by monitoring of immune response.

For passive immunization with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly, or yearly. In some methods, dosage is adjusted to achieve a plasma antibody concentration of 1-1000 µg/ml and in some methods 25-300 µg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogens range from about 10 ng to about 1 g, from about 100 ng to about 100 mg, from about 1 µg to about 10 mg, or from about 30 to about 300 µg DNA per patient. Doses for infectious viral vectors vary from 10-100, or more, virions per dose.

Agents for inducing an immune response can be administered by parenteral, topical, intravenous, oral, subcutaneous, intraarterial, intracranial, intraperitoneal, intranasal, or intramuscular means for prophylactic and/or therapeutic treatment. The most typical route of administration of an immunogenic agent is subcutaneous, although other routes can be equally effective. The next most common route is intramuscular injection. This type of injection is most typically performed in the arm or leg muscles. In some cases, it may be desirable to inject the therapeutic agent of the present invention directly into a particular tissue where deposits have accumulated, for example intracranial injection. Intramuscular injection or intravenous infusion is preferred for administration of antibody. In some methods, particular therapeutic antibodies are injected directly into the cranium. In some methods, antibodies are administered as a sustained release composition or device, such as a Medipad™ device (Elan Pharm. Technologies, Dublin, Ireland).

Another aspect of the present invention is directed to a combination therapy where an immunogenic tau peptide or antibody recognizing an immunogenic tau epitope of the present invention is administered in combination with agents that are effective for the prevention or treatment of other conditions or diseases associated with, or resulting from, the deposition of amyloidogenic proteins or peptides. Amyloidogenic proteins/peptides subject to deposition include, without limitation, beta protein precursor, prion and prion proteins, α-synuclein, tau, ABri precursor protein, ADan precursor protein, islet amyloid polypeptide, apolipoprotein AI, apolipoprotein AII, lyzozyme, cystatin C, gelsolin, atrial natriuretic factor, calcitonin, keratoepithelin, lactoferrin, immunoglobulin light chains, transthyretin, A amyloidosis, β2-microglobulin, immunoglobulin heavy chains, fibrinogen alpha chains, prolactin, keratin, and medin. Therefore, a combination therapeutic of the present invention would include an immunogenic tau peptide or antibody recognizing an immunogenic tau epitope and an agent or agents targeting one or more of the aforementioned amyloidogenic proteins or peptides.

In the case of amyloidogenic diseases such as, Alzheimer's disease and Down's syndrome, immune modulation to clear amyloid-beta (Aβ) deposits is an emerging therapy. Immunotherapies targeting Aβ have consistently resulted in cognitive improvements. It is likely that tau and Aβ pathologies are synergistic. Therefore, combination therapy targeting the clearance of both tau and Aβ and Aβ-related pathologies at the same time may be more effective than targeting each individually.

In the case of Parkinson's Disease and related neurodegenerative diseases, immune modulation to clear aggregated forms of the α-synuclein protein is also an emerging therapy. A combination therapy which targets the clearance of both tau and α-synuclein proteins simultaneously may be more effective than targeting either protein individually.

In the case of prion disease and related neurodegenerative diseases, immune modulation to clear the disease associated form of the prion protein, PrP$^{Sc}$, is an emerging therapy. Therefore, a combination therapy which targets the clearance of both tau and the pathological PrP$^{Sc}$ protein simultaneously may be more effective than targeting either protein individually.

Individuals with type-2 diabetes may be more prone to the development of Alzheimer's disease. Therefore, a combination therapy which includes an agent targeting the clearance of islet amyloid polypeptide and an agent preventing the development or progression of Alzheimer's diseases (i.e., preventing tau deposition) would have enhanced therapeutic benefit to the individual.

Another aspect of the present invention relates to a method of diagnosing an Alzheimer's disease or other tauopathy in a subject. This method involves detecting, in the subject, the presence of pathological tau conformer using a diagnostic reagent, where the diagnostic reagent is an antibody, or active binding fragment thereof, of the present invention. As described supra, the antibody has antigenic specificity for an isolated tau peptide having an amino acid sequence selected from SEQ ID NOs: 2-75 or SEQ ID NOs: 101-103. The diagnosis of the Alzheimer's disease or other tauopathy is based on the detection of a pathological tau conformer in the subject.

Detecting the presence of a pathological tau conformer in a subject using the diagnostic antibody reagent of the present invention can be achieved by obtaining a biological sample from the subject (e.g., blood, urine, cerebral spinal fluid), contacting the biological sample with the diagnostic antibody reagent, and detecting binding of the diagnostic antibody reagent to a pathological tau protein conformer in the sample from the subject. Assays for carrying out the detection of a pathological tau protein in a biological sample using the diagnostic antibody of the present invention are well known in the art and include, without limitation, ELISA, immunohistochemistry, western blot.

Alternatively, detecting the presence of a pathological tau protein conformer in a subject using the diagnostic antibody reagent of the present invention can be achieved using in vivo imaging techniques. In vivo imaging involves administering to the subject the diagnostic antibody having antigenic specificity for a pathological tau peptide or epitope (i.e., SEQ ID NOs: 2-75 and 101-103) and detecting binding of the diagnostic antibody reagent to the pathological tau protein conformer in vivo. As described supra, preferred antibodies bind to the pathological tau protein without binding to non-tau proteins and without binding to the non-pathological forms of tau.

Diagnostic antibodies or similar reagents can be administered by intravenous injection into the body of the patient, or directly into the brain by intracranial injection. The dosage of antibody should be within the same ranges as for treatment methods. Typically, the antibody is labeled, although in some methods, the primary antibody with affinity for the pathological tau protein is unlabelled and a secondary labeling agent is used to bind to the primary antibody. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled pathological tau conformers, tau aggregates, and/or neurofibrillary tangles in a sample from the subject or in the subject, to corresponding baseline values. The base line values can represent the mean levels in a population of undiseased individuals. Baseline values can also represent previous levels determined in the same subject.

The diagnostic methods described above can also be used to monitor a subject's response to therapy. In this embodiment, detecting the presence of pathological tau in a subject is determined prior to the commencement of treatment. The level of pathological tau in the subject at this timepoint is used as a baseline value. At various times during the course of treatment the detection of pathological tau protein conformers, tau aggregates, and/or neurofibrillary tangles is repeated, and the measured values thereafter compared with the baseline values. A decrease in values relative to baseline signals a positive response to treatment. Values can also increase temporarily in biological fluids as pathological tau is being cleared from the brain.

The present invention is further directed to a kit for performing the above described diagnostic and monitoring methods. Typically, such kits contain a diagnostic reagent, preferably the antibody of the present invention that has antigenic specificity for a pathological tau peptide (i.e., SEQ ID NOs: 2-75 and 101-103). The kit can also include a detectable label. The diagnostic antibody itself may contain the detectable label (e.g., fluorescent molecule, biotin, etc.) which is directly detectable or detectable via a secondary reaction (e.g., reaction with streptavidin). Alternatively, a second reagent containing the detectable label may be utilized, where the second reagent has binding specificity for the primary antibody. In a diagnostic kit suitable for measuring pathological tau protein in a biological sample, the antibodies of the kit may be supplied prebound to a solid phase, such as to the wells of a microtiter dish.

Diagnostic kits of the present invention also include kits that are useful for detecting antibody production in a subject following administration of an immunogenic tau peptide of the present invention. Typically, such kits include a reagent that contains the antigenic epitope of the antibodies generated by the subject. The kit also includes a detectable label. In a preferred embodiment, the label is typically in the form of labeled anti-idiotypic antibodies. The reagent of the kit can be supplied prebound to a solid phase, such as to the wells of a microtiter dish.

The following examples illustrate various methods for compositions in the treatment method of the invention. The examples are intended to illustrate, but in no way limit, the scope of the invention.

EXAMPLES

Example 1—Peptides

The peptide immunogens were synthesized at the Keck facility (Yale University), by the solid-phase technique on a p-methyl-benzhydrylamine resin, using a Biosearch SAM 2 synthesizer (Biosearch, Inc., San Rafael, Calif.). The peptides were cleaved from the resin with HF and then extracted with ether and acetic acid before lyophilization. Subsequently, the peptides were purified by HPLC with the use of a reverse-phase support medium (Delta-Bondapak) on a 0.78×30 cm column with a 0-66% linear gradient of acetonitrile in 0.1% TFA.

Example 2—Animals used in Studies

Studies were performed in the transgenic (Tg) JNPL3 P301L mouse model that develops neurofibrillary tangles in several brain regions and spinal cord (Taconic, Germantown, N.Y.) (Lewis et al., "Neurofibrillary Tangles, Amyotrophy and Progressive Motor Disturbance in Mice Expressing Mutant (P301L) Tau Protein," *Nat Genet* 25:402-405

(2000), which is hereby incorporated by reference in its entirety). While this model is not ideal for AD, it is an excellent model to study the consequences of tangle development and for screening therapy that may prevent the generation of these aggregates. Another advantage of these animals is the relatively early onset of pathology. In the homozygous line, behavioral abnormalities associated with tau pathology can be observed at least as early as 3 months, but the animals remain relatively healthy at least until 8 months of age. In other words, at 8 months, the animals ambulate, feed themselves, and can perform the behavioral tasks sufficiently well to allow the treatment effect to be monitored.

In addition to the JNPL3 P301L model, studies were also carried out using an htau/PS1 (M146L) mouse model (Boutajangout et al., "Presenilin 1 Mutation Promotes Tau Phosphorylation and Aggregation in a Novel Alzheimer's Disease Mouse Model," *Alzheimer's and Dementia* 4:T185 (2008), which is hereby incorporated by reference in its entirety). htau mice express unmutated human tau protein on a null mouse tau background and better resembles Alzheimer's tau pathology in the age of onset and brain distribution (Andorfer et al., "Hyperphosphorylation and Aggregation of Tau in Mice Expressing Normal Human Tau Isoforms," *J Neurochem* 86: 582-90 (2003), which is hereby incorporated by reference in its entirety). The PS1 model, carrying a mutation (M146L) in the Presenlin 1 protein, has shown to have increased Aβ levels and to promote Aβ deposition when crossed with Tg2576 mice (Duff et al., "Increased Amyloid-beta 42(43) in Brains of Mice Expressing Mutant Presenilin 1," *Nature* 383:710-713 (1996) and Holcomb et al., "Accelerated Alzheimer-Type Phenotype in Transgenic Mice Carrying Both Mutant Amyloid Precursor Protein and Presenilin 1 Transgenes," *Nature Med* 4:97-100 (1998), which are hereby incorporated by reference in their entirety).

htau mice, expressing all six human isoforms of tau, were crossed with PS1 (M146L) mice and maintained on a mouse tau knockout background (htau/PS1/mtau–/–). The PS1 mutation promotes hyperphosphorylation of tau in this model which leads to more aggressive tau pathology with earlier onset than in the htau model (Boutajangout et al., "Presenilin 1 Mutation Promotes Tau Phosphorylation and Aggregation in a Novel Alzheimer's Disease Mouse Model," *Alzheimer's and Dementia* 4:T185 (2008), which is hereby incorporated by reference in its entirety).

Example 3—Vaccine Administration

Phos-tau peptides were mixed with Adju-Phos adjuvant (Brenntag Biosector, Denmark) at a concentration of 1 mg/ml and the solution was rotated overnight at 4° C. prior to administration to allow the peptide to adsorb onto the aluminum phosphate particles.

JNPL3 P301L mice received a subcutaneous injection of 100 µl followed by a second injection 2 weeks later and then monthly thereafter (unless otherwise indicated). Vaccination started at 2-3 months of age and continued until the animals were 8-9 months of age at which time the animals were perfused and their organs collected for analysis. The mice went through a battery of sensorimotor tests at 5-6 months and again at 8-9 months of age prior to sacrifice. Control mice received the adjuvant alone.

htau/PS1/mtau–/– mice (n=12) were immunized with the phosphorylated tau immunogen Tau379-408[P-Ser396,404]. Three non-immunized control groups were included that received adjuvant alone. The main control group consisted of identical mice that were not immunized (htau/PS1 controls; n=16). Other control groups were htau/PS1 mice that expressed mouse tau (htau/PS1/mtau; n=8) as well as htau littermates on a mouse tau knockout background (htau controls; n=10).

htau/PS1/mtau–/– mice (3-4 months of age) received 100 µg of the phosphorylated tau derivative intraperitoneally (i.p.) in alum adjuvant with the first 3 injections every 2 weeks. Subsequent administration was at monthly intervals. The control groups received adjuvant alone. At 7-8 months the mice went through extensive behavioral testing to determine treatment efficacy, and were subsequently killed for analysis at 8-9 months of age. Locomotor activity, traverse beam, and rotarod tests were performed to determine if measured cognitive deficits in the learning and memory tasks could be attributed to sensorimotor abnormalities. Cognitive testing was performed using the radial arm maze, the closed field symmetrical maze, and the object recognition test (Sigurdsson et al., "An Attenuated Immune Response is Sufficient to Enhance Cognition in an Alzheimer's Disease Mouse Model Immunized with Amyloid-beta Derivatives," *J Neurosci* 24:6277-6282 (2004), Asuni et al., "Vaccination of Alzheimer's Model Mice with Abeta Derivative in Alum Adjuvant Reduces Abeta Burden Without Microhemorrhages." *Eur J Neurosci.* 24:2530-42 (2006), and Asuni et al., "Immunotherapy Targeting Pathological Tau Conformers in a Tangle Mouse Model Reduces Brain Pathology with Associated Functional Improvements," *J Neurosci* 27:9115-9129 (2007), which are hereby incorporated by reference in their entirety).

Example 4—Tau Immunotherapy Generates a Robust Antibody Response

The mice were bled prior to the commencement of the study (T0), a week following the third injection, periodically thereafter, and at sacrifice (Tf). The antibody response to the vaccine was determined by dilution of plasma (1:200 unless otherwise indicated) using an ELISA assay as described previously (Sigurdsson et al., "Immunization with a Non-Toxic/Non-Fibrillar Amyloid-β Homologous Peptide Reduces Alzheimer's Disease Associated Pathology in Transgenic Mice," *Am J Pathol.* 159:439-447 (2001) and Sigurdsson et al., "An Attenuated Immune Response is Sufficient to Enhance Cognition in an Alzheimer's Disease Mouse Model Immunized with Amyloid-beta Derivatives," *J Neurosci.* 24:6277-6282 (2004), which are hereby incorporated by reference in their entirety), where the immunogen was coated onto Immulon™ microtiter wells (Thermo Fischer Scientific, Waltham, Mass.). For detection, goat anti-mouse IgG (Pierce, Rockford, Ill.) or anti-mouse IgM (Sigma, St. Louis, Mo.) linked to a horseradish peroxidase were used at 1:3000 dilution. Tetramethyl benzidine (Pierce) was the substrate.

Figure 1B:
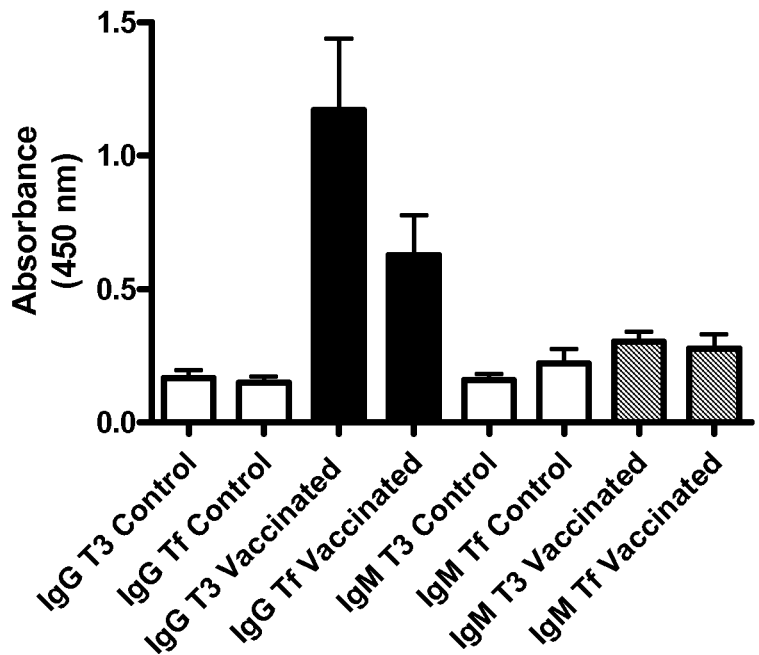

FIG. 1A shows the robust IgG and IgM immune response in JNPL3 P301L tangle mice immunized with Tau210-216 [P-Thr$_{212}$-Ser$_{214}$] (SEQ ID NO: 2) linked to tetanus toxin helper T-cell epitope (TT947-967) via GPSL linker. Mice of 2-3 months of age received the first two immunizations two weeks apart and then monthly thereafter. To assess antibody response, the mice were bled prior to the first immunization, periodically thereafter one week after vaccine administration, and when the mice were killed for tissue harvesting at 8-9 months of age. FIG. 1A shows IgG and IgM antibody response measured one week after the 6$^{th}$ immunization (T3) and again at 8-9 months of age, which was at the time of sacrifice (Tf=Tfinal). FIG. 1B shows that a strong antibody response was generated against the tetanus toxin epitope itself as assessed by IgG and IgM binding to an unrelated tau epitope Tau260-264[P-Ser$_{262}$] linked via GPSL to TT947-967.

Figure 2A:
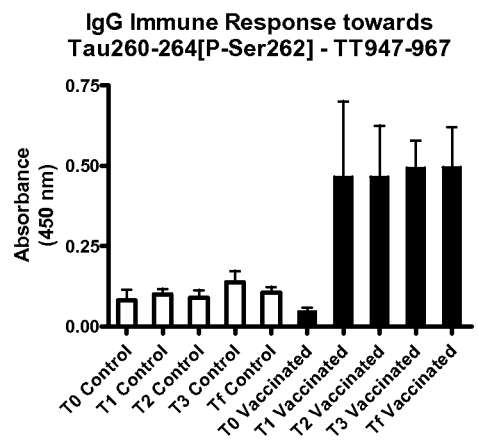
FIGS. 2A-2C show that JNPL3 P301L tangle mice immunized with Tau260-264[P-$Ser_{262}$] (SEQ ID NO: 3) (also referred to the T299 peptide) linked to tetanus toxin helper T-cell epitope (TT947-967) via a GPSL linker generate a robust IgG response against the immunogen.
Figure 2B:
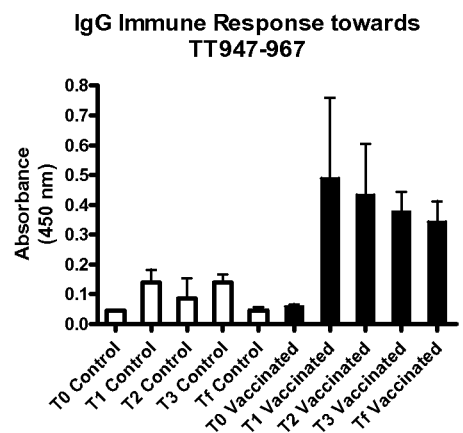
Figure 2C:
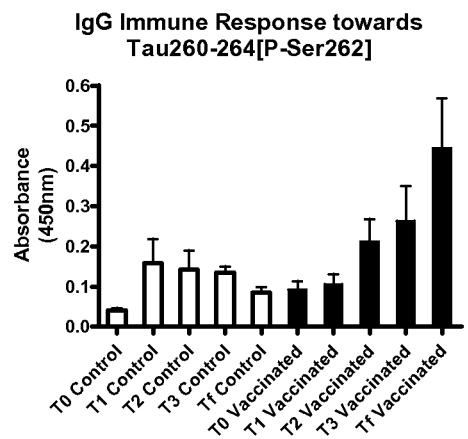

JNPL3 P301L tangle mice immunized with Tau260-264 [P-Ser$_{262}$] (SEQ ID NO:3) linked to tetanus toxin helper T-cell epitope (TT947-967) via GPSL linker generated a robust IgG response against the immunogen at shown in FIG. 2A. As above, the mice received the first two immunizations two weeks apart and then monthly thereafter from 2-3 months of age until 8-9 months of age. A good portion of that antibody response is generated against the tetanus toxin epitope as assessed by IgG binding to an unrelated tau epitope Tau210-216[P-Thr$_{212}$-Ser$_{214}$] linked via GPSL to TT947-967 (FIG. 2B). However, as shown in FIG. 2C, a good portion of the antibody response is also generated against the tau epitope as assessed by IgG binding to a larger tau epitope Tau240-270[P-Ser$_{262}$] that contains the Tau260-264[P-Ser$_{262}$] region. T0—Tfinal: Bleed prior to vaccination (T0), one week after third —(T1), sixth —(T2), seventh (T3) immunization, and at tissue harvesting (Tf).

Figure 3:
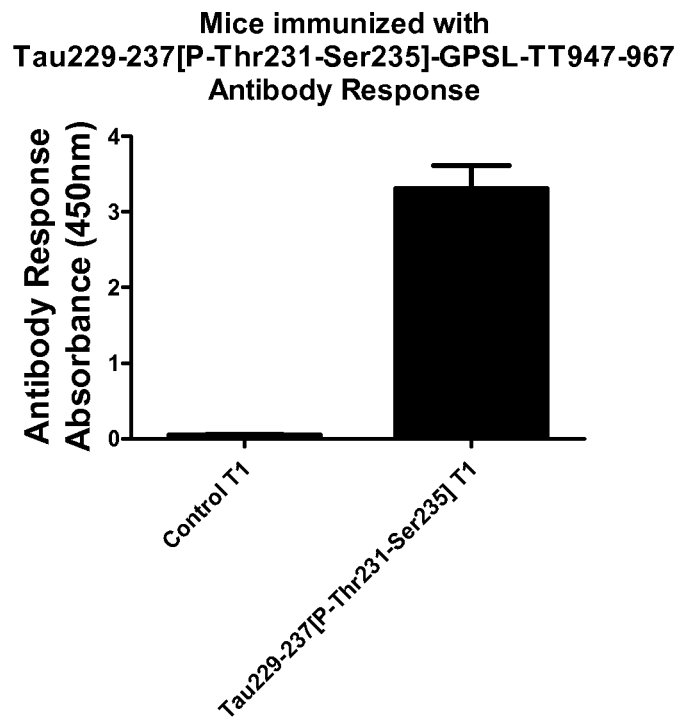
FIG. 3 shows the robust antibody (IgG) response generated in JNPL3 P301L tangle model mice immunized in with Tau229-237[P-Thr231-$Ser_{235}$] (SEQ ID NO: 4) linked to tetanus toxin helper T-cell epitope (TT947-967]. The mice were immunized from 2-3 months of age, two weeks apart, then a month later, and bled (T1) one week after the third immunization. ELISA plates were coated with 0.5 µg peptide per well and plasma was diluted 1:200.
Figure 4:
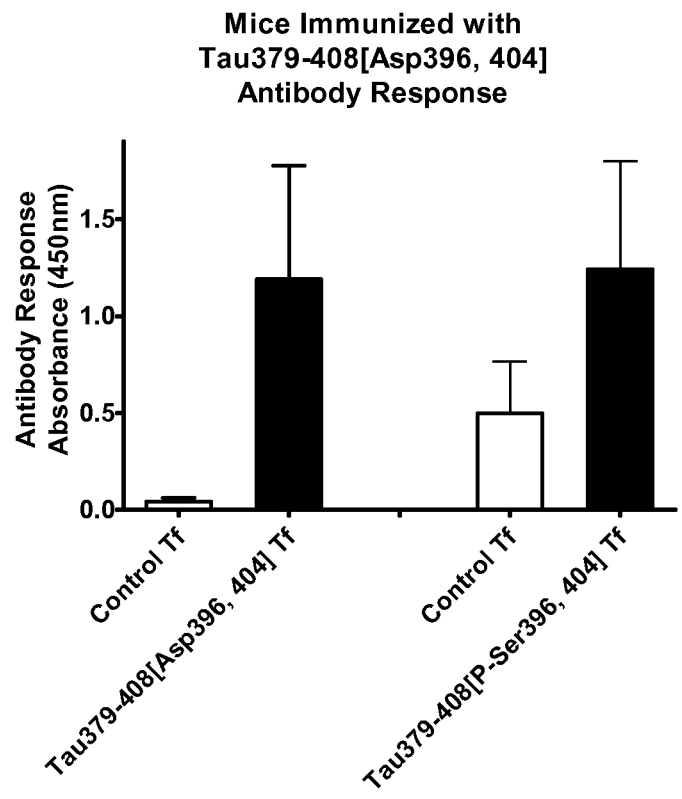
FIG. 4 shows the robust antibody (IgG) response generated in JNPL3 P301L tangle model mice immunized with the pseudophosphorylated immunogen, Tau379-408 [$Asp_{396,\ 404}$] (SEQ ID NO: 57) in alum adjuvant. Importantly, these antibodies recognize the phospho-epitope, Tau379-408[P-$Ser_{396,\ 404}$], to a similar degree. The mice were immunized from 2-3 months of age, two weeks apart for the first two immunizations, and monthly thereafter. The mice were bled (Tf=Tfinal) at the time of tissue harvesting at 8-9 months of age. ELISA plates were coated with 0.5 µg peptide per well and plasma was diluted 1:200.

A robust antibody (IgG) response was generated in JNPL3 P301L tangle model mice immunized in with Tau229-237 [P-Thr$_{231}$-Ser$_{235}$] (SEQ ID NO: 4) linked to tetanus toxin helper T-cell epitope (TT947-967) (FIG. 3). The mice were immunized from 2-3 months of age, two weeks apart and a month later, and bled (T1) one week after the third immunization.

A robust antibody (IgG) response was also generated in JNPL3 P301L tangle model mice immunized with the pseudophosphorylated immunogen, Tau379-408[Asp$_{396, 404}$] (SEQ ID NO: 57) in alum adjuvant. Importantly, these antibodies recognize the phospho-epitope, Tau379-408[P-Ser$_{396, 404}$], to a similar degree. The mice were immunized from 2-3 months of age, every two weeks for the first two immunizations, and monthly thereafter. The mice were bled (Tf=Tfinal) at the time of tissue harvesting at 7-8 months of age.

Example 5—Tau Immunotherapy Reduces Tau Aggregation in the Brain

For histological analysis of tau pathology, mice were anesthetized with sodium pentobarbital (120 mg/kg, i.p.), perfused transaortically with PBS and the brains processed as previously described (Sigurdsson et al., "Immunization with a Non-Toxic/Non-Fibrillar Amyloid-β Homologous Peptide Reduces Alzheimer's Disease Associated Pathology in Transgenic Mice," Am J Pathol 159:439-447 (2001); Sigurdsson et al., "An Attenuated Immune Response is Sufficient to Enhance Cognition in an Alzheimer's Disease Mouse Model Immunized with Amyloid-beta Derivatives," J Neurosci 24:6277-6282 (2004); and Sigurdsson E., "Histological Staining of Amyloid-beta in Mouse Brains," Methods Mol Biol 299:299-308 (2005), which are hereby incorporated by reference in their entirety). Briefly, the right hemisphere was immersion fixed overnight in periodate-lysine-paraformaldehyde (PLP), whereas the left hemisphere was snap-frozen for tau protein analysis. Following fixation, the brain was moved to a phosphate buffer solution containing 20% glycerol and 2% dimethylsulfoxide (DMSO) and stored at 4° C. until sectioned. Serial coronal brain sections (40 µm) were cut and every tenth section was stained with the PHF1 monoclonal antibody that recognizes phosphorylated serines 396 and 404 located within the microtubule-binding repeat on the C-terminal of PHF tau protein (Otvos et al., "Monoclonal Antibody PHF-1 Recognizes Tau Protein Phosphorylated at Serine Residues 396 and 404," J Neurosci Res 39:669-673 (1994), which is hereby incorporated by reference in its entirety)

Tau antibody staining was performed as described in Sigurdsson et al., "Immunization with a Non-Toxic/Non-Fibrillar Amyloid-β Homologous Peptide Reduces Alzheimer's Disease Associated Pathology in Transgenic Mice," Am J Pathol 159:439-447 (2001) and Sigurdsson et al., "An Attenuated Immune Response is Sufficient to Enhance Cognition in an Alzheimer's Disease Mouse Model Immunized with Amyloid-beta Derivatives," J Neurosci 24:6277-6282 (2004), which are hereby incorporated by reference in their entirety. Briefly, sections were incubated in the primary PHF1 antibody at a 1:100 to 1:1000 dilution. A mouse on mouse immunodetection kit (Vector Laboratories, Burlingame, Calif.) was used, in which the anti-mouse IgG secondary antibody was used at a 1:2000 dilution.

Analysis of tissue sections was quantified with a Bioquant image analysis system. The software uses hue, saturation, and intensity to segment objects in the image field. Thresholds were established with accurately identified objects on a standard set of slides and these segmentation thresholds remained constant throughout the analysis session. After establishing the threshold parameter, the image field was digitized with a frame grabber. The Bioquant software corrects for heterogeneity in background illumination (blank field correction) and calculates the measurement parameter for the entire field. For quantitative image analysis of immunohistochemistry, the granular layer of the dentate gyrus was initially selected which consistently contained intraneuronal tau aggregates (pretangles and tangles). This observation concurs with the original characterization of this model (Lewis et al., "Neurofibrillary Tangles, Amyotrophy and Progressive Motor Disturbance in Mice Expressing Mutant (P301L) Tau Protein," Nat Genet 25:402-405 (2000), which is hereby incorporated by reference in its entirety). All procedures were performed by an individual blind to the experimental conditions of the study. Sample numbers were randomized before the start of the tissue processing, and the code was broken only after the analysis was complete. Every tenth section from the mouse brain was sampled and the measurement was the percent of area in the measurement field at ×200 magnification occupied by reaction product with the tip of the dentate gyrus at the left edge of the field. Four to five sections were analyzed per animal.

Figures 5A, 5B:
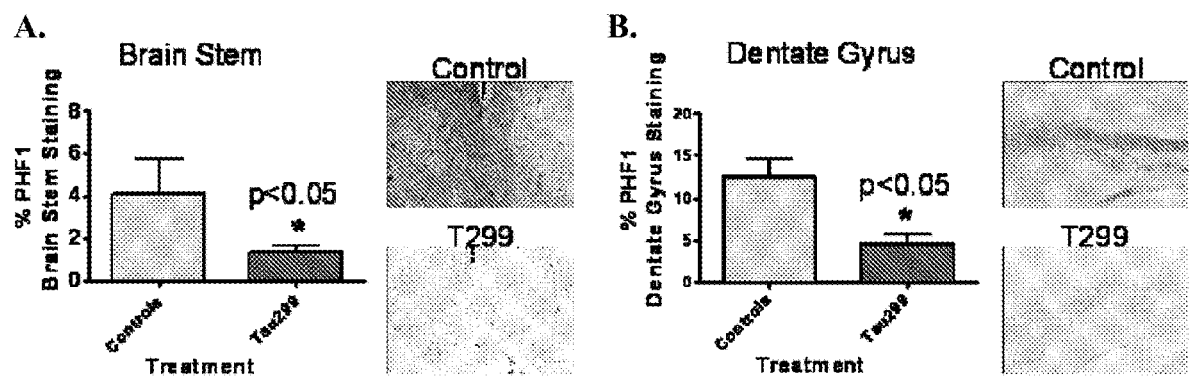
FIG. 5A-5B show the reduction of pathological tau observed in the brain stem (FIG. 5A) and dentate gyrus (FIG. 5B) of the tangle mouse model following tau immunotherapy. Homozygous JNPL3 tau P301L mice were immunized with T299 (Tau260-264[P-Ser$_{262}$] (SEQ ID NO: 3)) linked to a tetanus toxin helper T-cell epitope (TT947-967) via a GPSL linker sequence. Pathological tau in both the brain stem and dentate gyrus were assessed by PHF1 antibody immunostaining. PHF1 is a monoclonal antibody recognizing tau that is phosphorylated on serine amino acids 404 and 396 on the C-terminal (Greenberg et al., "Hydrofluoric Acid-Treated Tau PHF Proteins Display the Same Biochemical Properties as Normal Tau," *J Biol Chem* 267: 564-569 (1992), which is hereby incorporated by reference in its entirety). A significant reduction of pathological tau staining was observed in both the brain stem and dentate gyrus of animals actively immunized with the T299 peptide compared to control animals receiving adjuvant only.
Figure 6:
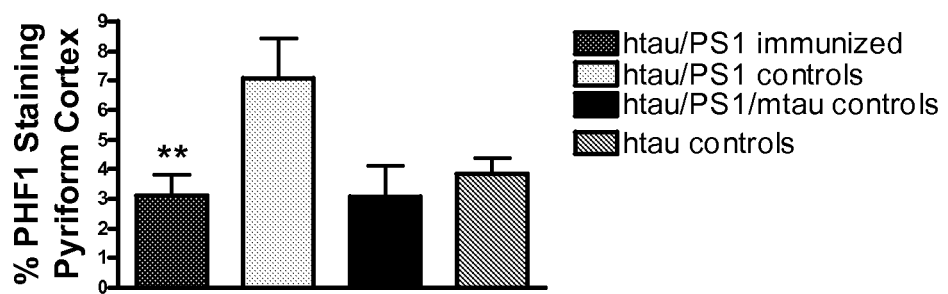
FIG. 6 shows that immunization of htau/PS1 mice with the phosphorylated Tau379-408[P-Ser$_{396,404}$] (SEQ ID NO: 82) reduces the amount of tau aggregates by 56% in the pyriform cortex. Significant difference was observed between the immunized and control groups (one-way ANOVA, $p<0.01$). Post hoc analysis also showed that immunized htau/PS1 mice differed from their htau/PS1 controls ($p<0.01$). **$p<0.01$.

Immunization of homozygous JNPL3 tau P301L mice with Tau260-264[P-Ser$_{262}$] (SEQ ID NO: 3) linked to TT947-967 (T299) reduced the levels of pathological tau in both the brain stem (FIG. 5A) and the dentate gyrus (FIG. 5B) compared to control mice receiving adjuvant only. Similarly, immunization of htau/PS1 mice with the phosphorylated Tau379-408[P-Ser$_{396,404}$] immunogenic peptide reduced the amount of tau aggregates by 56% in the pyriform cortex (FIG. 6, compare htau/PS1 immunized vs. htau/PS1 controls). Significant difference was observed between the immunized and control groups (one-way ANOVA, p<0.01). Post hoc analysis also showed that immunized htau/PS1 mice differed from their htau/PS1 controls (p<0.01). **p<0.01.

Example 6—Tau Immunotherapy Prevents Cognitive Decline

To determine if the tau immunotherapy prevented or reversed the age-related sensorimotor abnormalities observed in the P301L or if it caused any motor impairments in the htau/PS1 mice, animals administered the immunogenic Tau 260-264[P-Ser$_{262}$] (SEQ ID NO: 3) or Tau 379-

408[P-Ser$_{396, 404}$] (SEQ ID NO: 82) were assessed using a variety of sensorimotor and cognitive tests described below.

Rotarod Test: Animals were placed onto the rod (diameter 3.6 cm) apparatus to assess differences in motor coordination and balance by measuring fore- and hindlimb motor coordination and balance (Rotarod 7650 accelerating model; Ugo Basile, Biological Research Apparatus, Varese, Italy). This procedure was designed to assess motor behavior without a practice confound. The animals were habituated to the apparatus by receiving training sessions of two trials, sufficient to reach a baseline level of performance. Then, the mice were tested three additional times, with increasing speed. During habituation, the rotarod was set at 1.0 rpm, which was gradually raised every 30 sec, and was also wiped clean with 30% ethanol solution after each session. A soft foam cushion was placed beneath the apparatus to prevent potential injury from falling. Each animal was tested for three sessions (data combined for subsequent analysis), with each session separated by 15 min, and measures were taken for latency to fall or invert (by clinging) from the top of the rotating barrel.

Traverse Beam: This task tests balance and general motor coordination and function integration. Mice were assessed by measuring their ability to traverse a graded narrow wooden beam to reach a goal box (Torres et al., "Behavioural, Histochemical and Biochemical Consequences of Selective Immunolesions in Discrete Regions of the Basal Forebrain Cholinergic System," *Neuroscience* 63:95-122 (1994), which is hereby incorporated by reference in its entirety). The mice were placed on a 1.1 cm wide beam that is 50.8 cm long and suspended 30 cm above a padded surface by two identical columns. Attached at each end of the beam is a shaded goal box. Mice were placed on the beam in a perpendicular orientation to habituate and were then monitored for a maximum of 60 sec. The number of foot slips each mouse had before falling or reaching the goal box were recorded for each of four successive trials. Errors are defined as footslips and were recorded numerically.

Radial Arm Maze: The maze apparatus is an 8-arm elevated radial maze constructed from Plexiglas. Each arm is 35 cm long and 7 cm wide with a water cup 1 cm in diameter positioned at the end of each arm. Sidewalls 15 cm high extend 12 cm into each arm to prevent animals from crossing between arms. The central area is an octagonal shaped hub 14 cm in diameter. Clear Plexiglas guillotine doors, operated remotely by a pulley system control access to the arms. The maze is elevated 75 cm above floor level and situated in a room in which several distinctive objects of a constant location serve as extra maze cues. Prior to testing, mice were adapted for 5 days. During this period, the mice received 0.1% saccharine in water for 1 hour per day and were then adapted 16 hours later to access the sugar solution from a cup placed at the end of each arm. The first two days of adaptation were performed in a Y-maze which the mice were allowed to explore freely. The subsequent three days of adaptation were performed in the radial arm maze, in which the doors were raised and lowered periodically to accustom the animals to the sound associated with their operation. The same water deprivation schedule was maintained during the 9 day testing period. The mice maintain good health on this schedule. Each testing trial was begun by placing the mouse in the central area and raising all doors. When an arm was entered all doors were lowered. After the mouse consumed the saccharine water, the door to that arm was raised allowing the mouse to return to the central arena. After a 5 sec interval, the next trial was initiated by again raising all of the doors simultaneously. This procedure was continued until the animal had entered all 8 arms or until 10 min has elapsed. Daily acquisition sessions were continued for 9 days. The number of errors (entries to previously visited arms) and time to complete each session were recorded.

Object Recognition: The spontaneous object recognition test that was utilized measures deficits in short term memory, and was conducted in a square-shaped open-field box (48 cm square, with 18 cm high walls constructed from black Plexiglas), raised 50 cm from the floor. The light intensity was set to 30 lx. On the day before the tests, mice were individually habituated in a session in which they were allowed to explore the empty box for 15 min. During training sessions, two novel objects were placed at diagonal corners in the open field and the animal was allowed to explore for 15 min. For any given trial, the objects in a pair were 10 cm high, and composed of the same material so that they could not readily be distinguished by olfactory cues. The time spent exploring each object was recorded by a tracking system (San Diego Instruments, San Diego, Calif.), and at the end of the training phase, the mouse was removed from the box for the duration of the retention delay (RD=3 h). Normal mice remember a specific object after a delay of up to 1 h and spend the majority of their time investigating the novel object during the retention trial. During retention tests, the animals were placed back into the same box, in which one of the previous familiar objects used during training was replaced by a second novel object, and allowed to explore freely for 6 min. A different object pair was used for each trial for a given animal, and the order of exposure to object pairs as well as the designated sample and novel objects for each pair were counterbalanced within and across groups. The time spent exploring the novel and familiar objects was recorded for the 6 min.

Closed Field Symmetrical Maze: This apparatus is a rectangular field 30 cm square with 9 cm high walls divided into 36, 9.5 cm squares and covered by a clear Plexiglas top. Endboxes, each 11×16×9 cm, are situated at diagonal corners of the field. The symmetrical maze is a modification of the Hebb-Williams and Rabinovitch-Rosvold type of tests, as discussed previously (Asuni et al., "Vaccination of Alzheimer's Model Mice with Abeta Derivative in Alum Adjuvant Reduces Abeta Burden without Microhemorrhages," *Eur J Neurosci* 24:2530-2542 (2006), which is hereby incorporated by reference in its entirety). Briefly, the main difference is that each end-compartment functions as both a startbox and a goalbox, and the mice run in opposite direction on alternate trials, thereby eliminating intertrial handling. The barriers are placed in the field in symmetrical patterns, so that mice face the same turns going in either direction within a given problem. Prior to testing, the mice were adapted to a water restriction schedule (2 h daily access to water). The mice were given two adaptation sessions prior to the beginning of testing. In the first session, all animals were given saccharine flavored water in the goal box for 10 min. In session 2, they were placed in the start chamber and permitted to explore the field and enter the goal box where water reward (0.05 mL) was available. When the mice were running reliably from the start chamber to the goal box, they were given three practice sessions on simple problems where one or two barriers were placed in different positions in the field so as to obstruct direct access to the goal box. Formal testing consisted of the presentation of three problems graded in difficulty based on previous data (Asuni et al., "Vaccination of Alzheimer's Model Mice with Abeta Derivative in Alum Adjuvant Reduces Abeta Burden without Microhemorrhages," *Eur J Neurosci* 24:2530-2542 (2006), which is hereby incorporated by reference in its entirety) and published norms for mice. One problem was presented per day and the mice were given five trials on each problem with an intertrial interval of 2 min. Performance was scored manually by the same observer in terms of errors (i.e., entries and reentries into designated error zones) and time to complete each trial.

The objective of these experiments was to evaluate the effects of the vaccination on selected sensorimotor (i.e., traverse beam and rotarod) and cognitive behaviors (i.e., radial arm maze, object recognition test, and closed field symmetrical maze test). The homozygous P301L mice have tangle pathology as early as 3 months of age and those animals were tested at 5 and 8 months of age. The htau/PS1 animals were tested at 7-8 months of age.

Figure 7A:
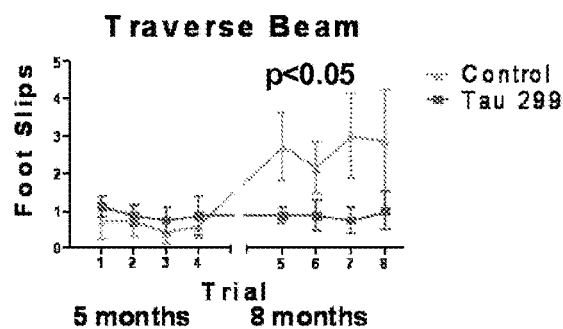
FIGS. 7A-7B show that tau immunotherapy prevents functional impairment in a tangle mouse model. Homozygous JNPL3 P301L mice were immunized with the phosphorylated immunogenic Tau 299 peptide (Tau260-264[P-Ser$_{262}$] (SEQ ID NO:3)) linked to a tetanus toxin helper T-cell epitope (TT947-967) via a GPSL linker sequence. Control animals received adjuvant alone. Administration of the Tau260-264[P-Ser$_{262}$] peptide vaccine prevented functional impairments assessed using the traverse beam at 8 months of age as indicated by the fewer number of footslips recorded for the immunized animals compared to the control animals (FIG. 7A). Likewise, administration of the Tau260-264[P-Ser$_{262}$] peptide vaccine prevented functional impairments assessed by the rotarod test, both at 5-6 months of age and at 8-9 months of age (FIG. 7B).
Figure 7B:
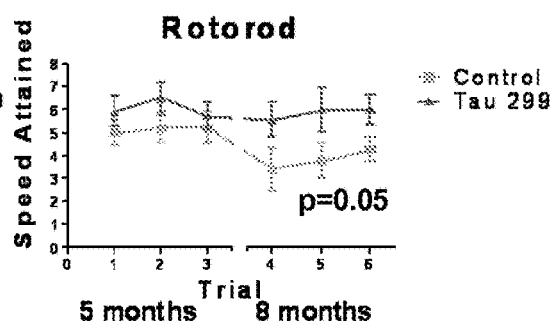

Immunization of homozygous JNPL3 tau P301L mice with the phosphorylated immunogenic tau peptide Tau260-264[P-Ser$_{262}$] linked to the tetanus toxin helper T-cell epitope (TT947-967) prevented functional impairment associated with the development of neurofibrillary tangles as assessed using the traverse beam test at 8 months of age (FIG. 7A) and the rotarod test at 5-6 months of age and at 8-9 months of age (FIG. 7B). Control JNPL3 tau P301L mice received adjuvant alone.

Figure 8A:
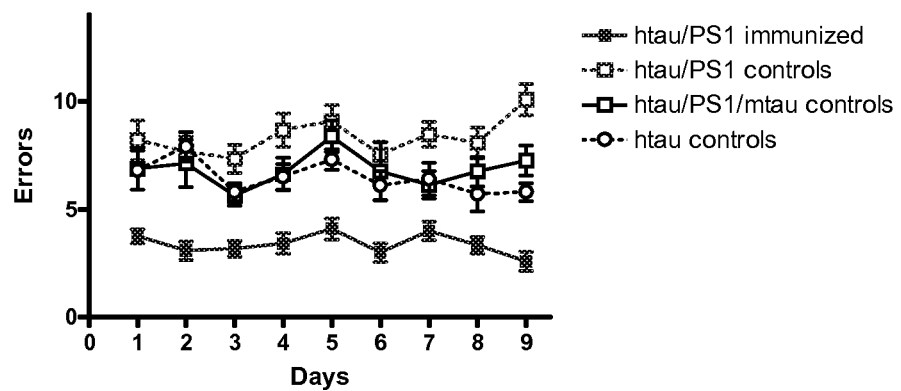
FIGS. 8A-8B show that immunization of htau/PS1 mice with the phosphorylated Tau379-408[P-Ser$_{396,404}$] (SEQ ID NO:82) improves performance in the radial arm maze (FIG. 8A) and the object recognition test (FIG. 8B). A significant difference was observed between the immunized and control groups in the radial arm maze (two-way ANOVA repeated measures, $p<0.0001$) as shown in FIG. 8A. Neuman-Keuls post-hoc test revealed that the immunized htau/PS1 mice performed better (i.e., committed less errors) than the control htau/PS1 mice on all the days ($p<0.01$-$0.001$). A significant difference was also observed between the groups in the object recognition test (one-way ANOVA, $p=0.005$) (FIG. 8B). Neuman-Keuls post-hoc test revealed that the immunized htau/PS1 mice had better short-term memory than identical control mice ($p<0.01$). It has been well established that cognitively normal mice spend about 70% of their time with the new object compared to the old object. **$p<0.01$.
Figure 8B:
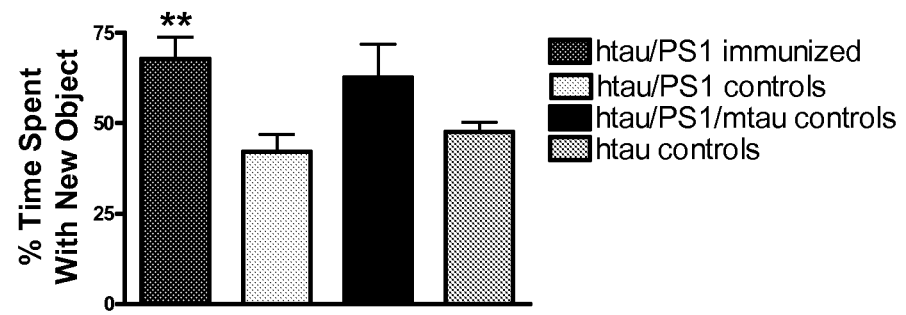
Figures 9A, 9B, 9C:
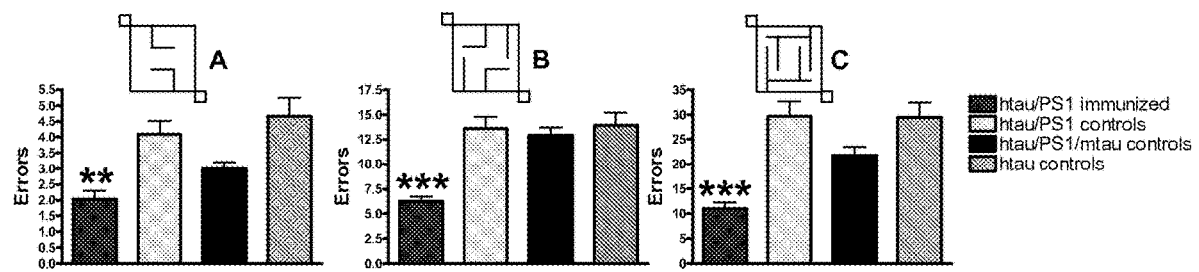
FIGS. 9A-9C show that immunization of htau/PS1 mice with the phosphorylated Tau379-408[P-Ser$_{396,404}$] (SEQ ID NO:82) improves performance in the closed field symmetrical maze. Significant differences were observed between the immunized and control groups with respect to the number of errors committed in each of mazes 9A-9C (one-way ANOVA, Maze A: $p<0.001$, Maze B: $p<0.0001$, Maze C: $p<0.01$). Post-hoc analysis revealed that the treated htau/PS1 group performed better than their identical control mice (htau/PS1 controls) (Maze A: $p<0.01$, Mazes B, C: $p<0.001$). Post-hoc analysis also revealed significant differences between some of the other groups depending on the maze but those differences are less relevant and are therefore not detailed here. The three mazes were of increasing complexity as indicated by the number of errors (note that the Y axis scale differs). $p<0.01$, *$p<0.001$.

Immunization of htau/PS1 mice with the phosphorylated Tau379-408[P-Ser396,404] prevented cognitive decline in all three tests that were employed: 1) the radial arm maze (RAM; two-way ANOVA repeated measures, p<0.0001, FIG. 8A), 2) the object recognition test (ORT; one-way ANOVA, p=0.005, FIG. 8B), and 3) the closed field symmetrical maze (CFSM; one-way ANOVA, Maze A: p<0.001, Maze B: p<0.0001, Maze C: p<0.01, FIGS. 9A-9C). In the RAM and the CFSM, the immunized htau/PS1 mice performed better than the control htau/PS1 mice on all the days (RAM; p<0.01-0.001) and in all the mazes that were of increasing complexity, as indicated by the number of errors (note that the Y axis scale differs; CFSM Maze A: p<0.01, Mazes B, C: p<0.001). In the ORT, post hoc analysis revealed that the immunized htau/PS1 mice had better short-term memory than identical control mice (p<0.01). It is well established that cognitively normal mice spend about 70% of their time with the new object compared to the old object (Asuni et al., "Immunotherapy Targeting Pathological Tau Conformers in a Tangle Mouse Model Reduces Brain Pathology with Associated Functional Improvements," *J Neurosci* 27:9115-9129 (2007), which is hereby incorporated by reference in its entirety). The immunized htau/PS1 mice did not differ significantly from their non-immunized identical control mice in any of the sensorimotor tasks (rotarod, traverse beam, locomotor activity). These findings indicate that the cognitive improvements observed following the immunization cannot be explained by sensorimotor effects, which further strengthens the results.

Example 7—Tau Immunotherapy Reduces Levels of Pathological Tau

Brain tissue was homogenized in a buffer containing 0.1 mM 2-(N-morpholino) ethanosulfonic acid, 0.5 mM MgSO$_4$, 1 mM EGTA, 2 mM dithiothreitol, pH 6.8, 0.75 mM NaCl, 2 mM phenylmethyl sulfonyl fluoride, Complete mini protease inhibitor mixture (1 tablet in 10 ml of water; Roche) and phosphatase inhibitors (20 mM NaF and 0.5 mM sodium orthovanadate). The homogenate was then centrifuged (20,000×g) for 30 min at 4° C. to separate a soluble cytosolic fraction (supernatant 1) and insoluble fraction (pellet 1). The pellet was resuspended in the same volume of buffer without protease and phosphatase inhibitors, but that contained 1% (v/v) Triton X-100 and 0.25% (w/v) desoxycholate sodium and ultracentrifuged at 50,000 for 30 min to obtain a detergent-extracted supernatant 2 that was analyzed as insoluble fraction. Supernatant 1 and 2 were heated at 100° C. for 5 min and the same amount of protein was electrophoresed on 12% (w/v) polyacrylamide gel. The blots were blocked in 5% non-fat milk with 0.1% Tween-20 in TBS, and incubated with different antibodies overnight, and then washed and incubated at room temperature for 1 h with peroxidase-conjugated, anti-mouse or anti-rabbit IgG. Subsequently, the bound antibodies were detected by ECL (Pierce). Densitometric analysis of immunoblots were performed by NIH Image J program and the levels of pathological tau was normalized relative to the amounts of total tau protein instead of actin levels, as some studies have reported that changes in pathophysiological conditions and interactions with extracellular matrix components can alter actin protein synthesis, rendering actin unsuitable as an internal standard.

Figures 10A, 10B, 10C, 10D, 10E, 10F:
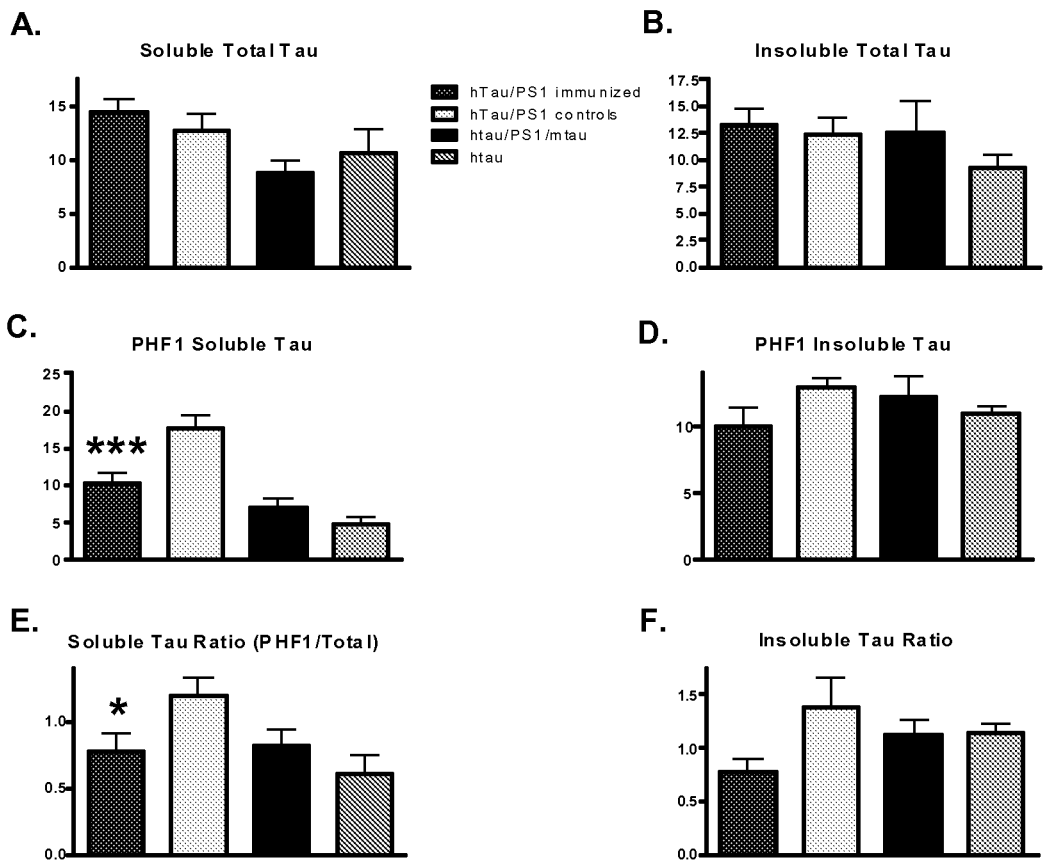
FIGS. 10A-10F are graphs depicting the levels of soluble and insoluble tau (total tau and pathological tau) detected by western blot analysis in htau/PS1 mice immunized with phosphorylated Tau379-408[P-Ser$_{396,404}$] (SEQ ID NO:82) and corresponding controls. Tau immunotherapy reduces pathological tau compared to total tau by 35-43% (FIGS. 10C and 10D). The immunotherapy did not affect total tau levels as assessed with B19 antibody (FIGS. 10A and 10B) which is important for the safety of this approach. Compared to htau/PS1 controls, PHF1 soluble tau was significantly reduced ($p<0.001$) and the soluble tau ratio (PHF1/total tau) was reduced by 35% ($p<0.05$) (FIG. 10E). A strong trend for reduction in PHF1 insoluble tau was observed as well ($p=0.06$), and the insoluble tau ratio (PHF1/total tau) was reduced by 43% ($p=0.08$) (FIG. 10F). *$p<0.05$, ***$p<0.001$ FIGS. 11A-11C demonstrate that passive immunotherapy targeting the phosphorylated tau 396 and 404 epitopes prevents functional decline and reduces tau pathology in P301L tangle mice.

For Western blot analysis, total tau was measured with polyclonal B19 antibody whereas pathological tau was detected with monoclonal PHF1 antibody (FIGS. 10A-10F). Levels of total soluble and insoluble tau did not differ significantly between the groups (FIG. 10A-10B), whereas levels of soluble PHF1 stained tau were significantly decreased (41%, p<0.001) in the immunized mice compared to their identical controls (FIG. 10C). A trend was observed for a decrease (22%) in insoluble PHF1 reactive tau (FIG. 10D). Further analysis indicated a very strong trend for the immunotherapy to reduce the ratio of PHF1/B19 by 35% and 43% in the soluble and insoluble fractions, respectively (FIGS. 10E and 10F). These findings indicate that pathological tau was preferentially being cleared.

Importantly, cognitive improvements observed in the htau/PS1 mice receiving immunotherapy correlated well with reduction in PHF1 stained tau aggregates assessed by immunohistochemistry. Significant correlation was observed in all three memory tests (RAM (last day of testing analyzed): r=0.36, p=0.01; CFSM: Maze A, r=0.33, p=0.02; Maze C, r=0.40, p=0.01; ORT: r=−0.31, p=0.03). With regard to the western blot fractions, significant correlation was observed in both soluble and insoluble fractions and their ratios relative to total tau in the radial arm maze (soluble PHF1: r=0.41, p<0.01; soluble PHF1/total soluble tau: r=0.34, p<0.05; insoluble PHF1: r=0.52, p<0.001; insoluble PHF1/total insoluble tau: r=0.33, p<0.05) but not in the two other cognitive tests.

Example 8—Passive Immunotherapy Targeting the P-396, 404 Epitope Prevents Functional Decline and Reduces Tau Aggregates in the Brain To determine the feasibility of passive immunotherapy, homozygous P30I L mice were injected intraperitoneally (i.p.) with PHF1, a monoclonal tau antibody (provided by Dr. Peter Davies) that recognizes NFT and pretangles in the P301L (JNPL3) mouse model and in AD (Lewis et al, "Neurofibrillary Tangles, Amyotrophy and Progressive Motor Disturbance in Mice Expressing Mutant (P301L) Tau Protein," *Nat Genet* 25:402-40522 (2000), which is hereby incorporated by reference in its entirety). This monoclonal antibody recognizes tau that is phosphorylated on serine amino acids 404 and 396 on the C-terminal of tau (Greenberg et al., "Hydrofluoric Acid-Treated Tau PHF Proteins Display the Same Biochemical Properties as Normal Tau," *J Biol Chem* 267:564-569 (1992) which is hereby incorporated by reference in its entirety). Therefore, it is a monoclonal analog of the prototype of one active immunization approach (Asuni et al., "Immunotherapy Targeting Pathological Tau Conformers in a Tangle Mouse Model Reduces Brain Pathology with Associated Functional Improvements," *J Neurosci* 27:9115-9129 (2007), which is hereby incorporated by reference in its entirety), Tau379-408[P-Ser396,404] that contains the PHF1 antibody epitope.

The dose of PHF1 was 250 µg/125 µL dissolved in PBS. Controls were injected i.p. with same dose of mouse IgG in PBS. The first injection was administered between 9-12 weeks of age. Animals subsequently received weekly administrations for a total of 13 injections, followed by behavioral testing at 5-6 months and subsequent tissue analysis at 6-7 months.

Figure 11A:
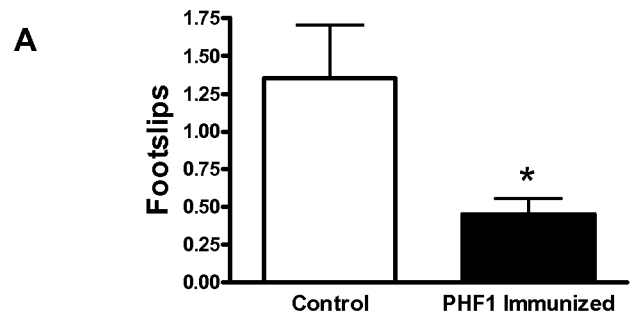
FIG. 11A is a graph showing a significant difference in the number of footslips taken on the traverse beam by IgG injected control and PHF1 immunized P301L mice, with control animals having more footslips when crossing the beam (trials combined, $p=0.03$).
Figure 11B:
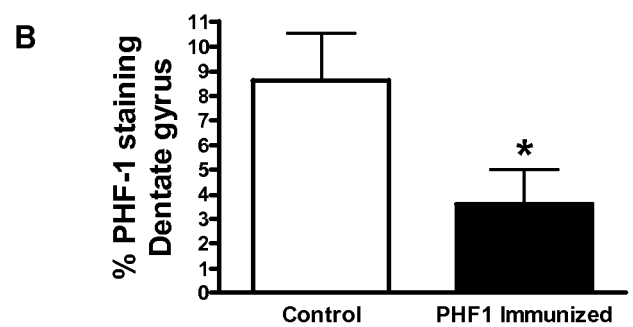
FIG. 11B is a graph showing the percentage of tau immunostaining in the dentate gyrus of immunized and control P301L mice. PHF1 immunized P301L mice had 58% less PHF1 stained tau pathology in the dentate gyrus than controls ($p=0.02$).
Figures 12A, 12B:
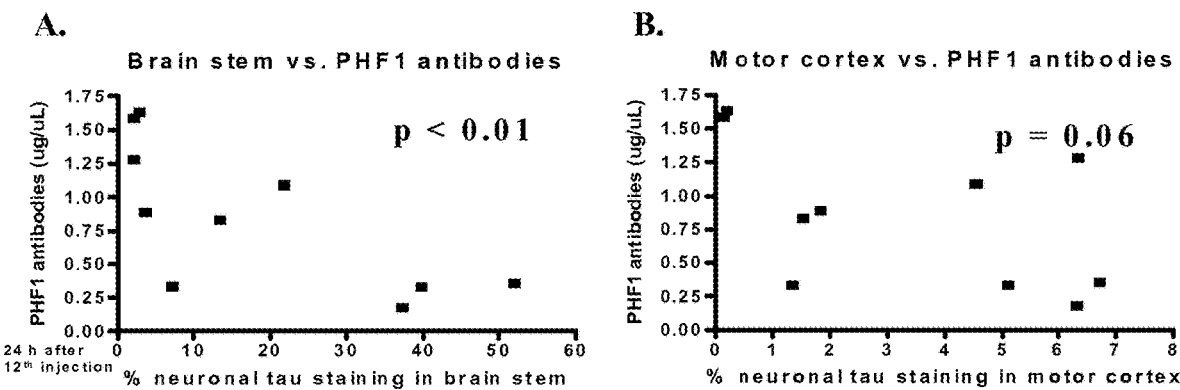
FIGS. 12A-12B are graphs showing the inverse correlation between plasma levels of PHF1 antibodies and tau pathology. Significant correlation was observed in the brain stem (FIG. 12A; $p<0.01$), and a strong trend for correlation in the motor cortex (FIG. 12B; $p=0.06$).

Passive immunization with the PHF1 antibody prevented tau pathology associated motor decline in the P301L mouse model. As shown in FIG. 11A, there was a significant difference between IgG injected controls and PHF1 immunized animals on the traverse beam, with control animals having more footslips when crossing the beam than immunized animals (trials combined, p=0.03). Likewise, PHF1 immunized P301L mice had 58% less PHF1 stained tau pathology in the dentate gyrus than controls (p=0.02) (FIG. 11B). An inverse correlation between plasma levels of PHF1 antibodies and tau pathology was observed in the brain stem (FIG. 12A; p<0.01), and a strong trend for correlation in the motor cortex (FIG. 12B; p=0.06).

Figure 11C:
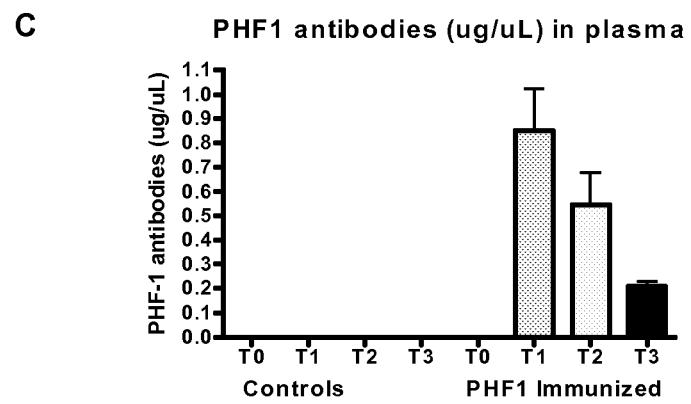
As shown in FIG. 11C, the amount of PHF-1 antibodies (µg/µL) in plasma decreased four-fold in two weeks. No detectable antibodies were observed in controls, whereas the levels in immunized animals decreased over time. These are the average values for the immunized mice. T0: prior to first immunization, T1: 24 h after the 12th injection, T2: 7 days after the 13th and last injection, T3: 14 days after last injection. The ELISA plates were coated with Tau379-408 [P-Ser$_{396,404}$]

The amount of PHF-1 antibodies (µg/µL) in plasma of immunized animals decreased four-fold in two weeks (FIG. 11C). No detectable antibodies were observed in controls. These are the average values for the immunized mice.

Example 9—Generation of Monoclonal Tau Antibodies

Figure 13A:
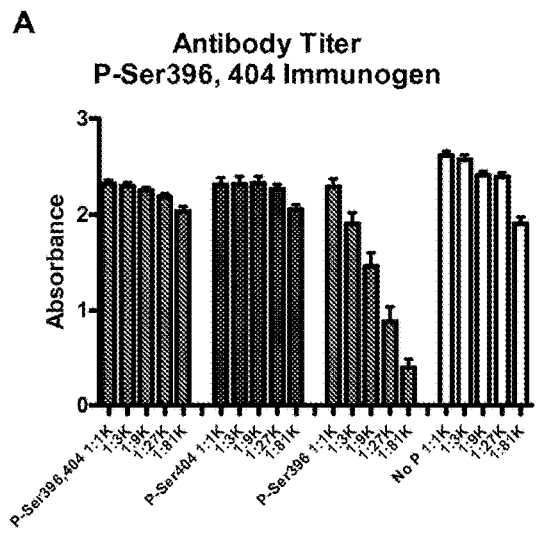
FIGS. 13A-13B are graphs depicting the generation of monoclonal antibodies against the immunogenic tau peptide comprising amino acids 386-408 (SEQ ID NO:13) containing phosphorylated serine epitopes at amino acid positions 396 and 404.
Figure 13B:
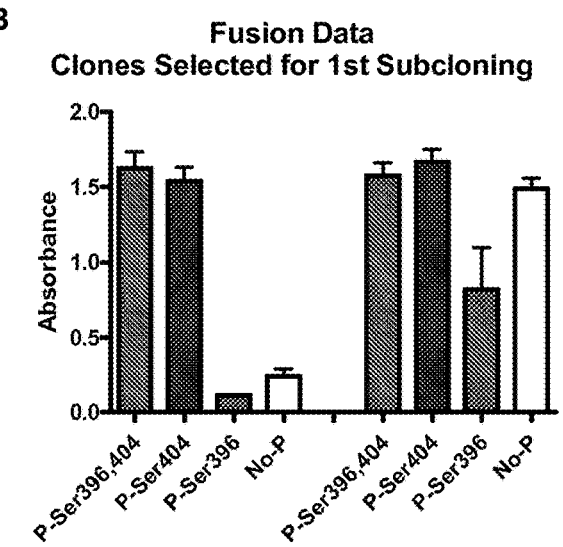

Ten balb/c mice were immunized with Tau386-408[P-Ser$_{396,404}$] (SEQ ID NO:13) linked to KLH via a cysteine residue added to the N-terminus. Strong antibody titer was generated against the tau portion of the immunogen as detected by serial dilutions of plasma (FIG. 13A). Two mice were selected for cell fusion and initial screening was performed with the immunogen peptide without KLH. Second screening was performed with the same peptide as well as Tau386-408[P-Ser$_{396}$], Tau386-408[P-Ser$_{404}$] and the non-phospho peptide Tau386-408 (FIG. 13B). Based on that screening, clones were selected for the first and second subcloning. Importantly, numerous strongly positive clones were identified (>50) and stable clones have been identified that specifically recognize a phospho-epitope within this region or that bind to a non-phosphorylated site within this region, thereby allowing a comparison of the efficacy and safety profile of antibodies binding to a phospho- or non-phospho tau epitopes within the same region of the molecule.

Figures 14A, 14B:
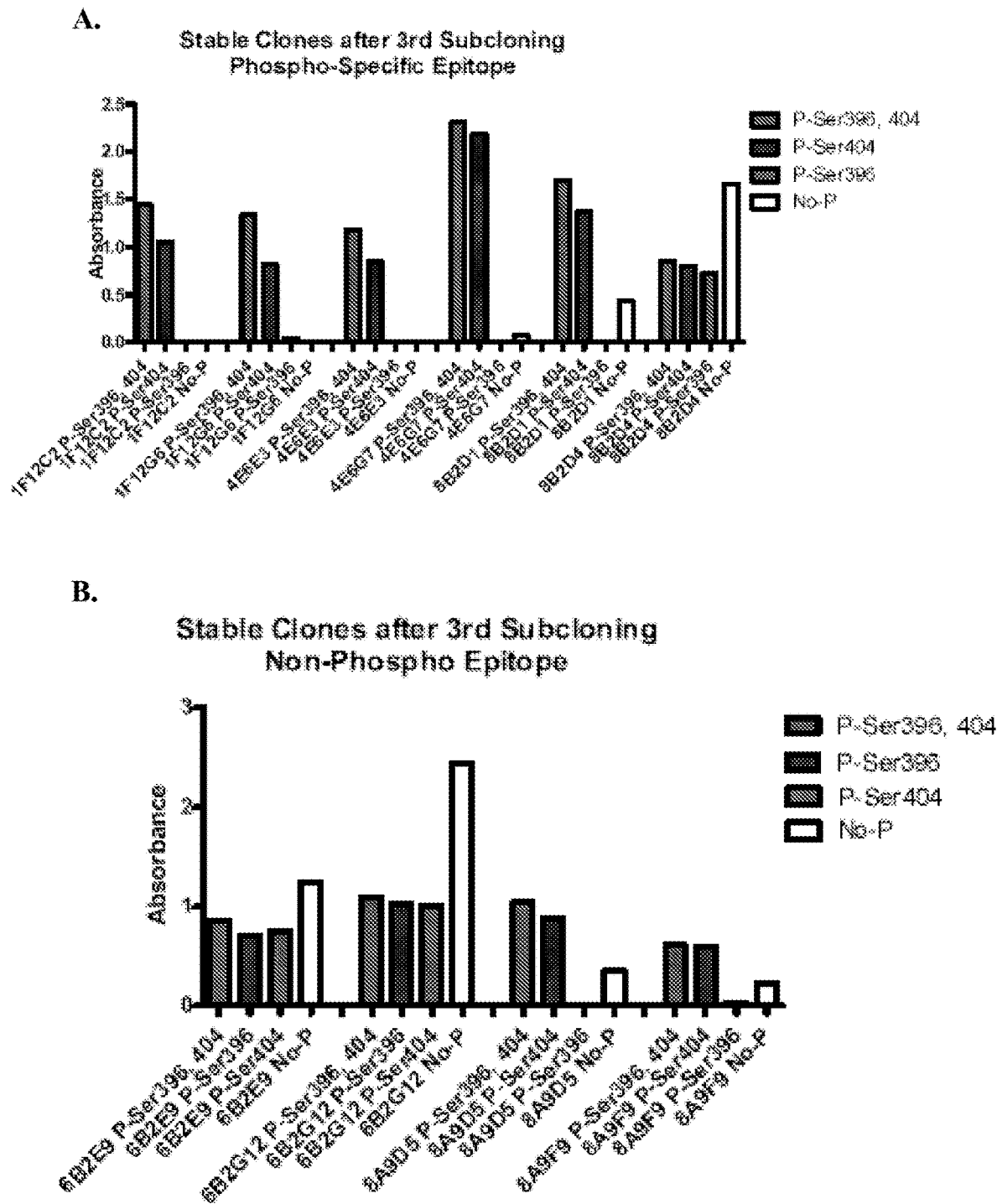
FIGS. 14A-14B are graphs showing epitope binding of stable phospho-specific (FIG. 14A) and non-phospho-specific (FIG. 14B) Tau-386-408[P-Ser$_{396,404}$] antibody clones after third subcloning by ELISA. Of the phospho-specific monoclonal antibodies selected for further subcloning, four out of six retained their specificity for the phospho-Ser$_{404}$ epitope (see clones 1F12C2, 1F12G6, 4E6E3, and 4E6G7 in FIG. 14A). Two clones are less phospho-specific (8B2D1) or non-specific (8B2D4) (FIG. 14A). Of the non-phospho-specific monoclonal antibodies, 6B2E9 and 6B2G12, in particular, retained their non-specificity after further subcloning (FIG. 14B). Data presented was obtained at 1:810 dilution of culture supernatant.

Of the phospho-specific monoclonal antibodies selected for further subcloning, four out of six retained their specificity for the phospho-Ser$_{404}$ epitope (see clones 1F12C2, 1F12G6, 4E6E3, and 4E6G7 in FIG. 14A). Two clones are less phospho-specific (8B2D1) or non-specific (8B2D4) (FIG. 14A). Of the non-phospho-specific monoclonal antibodies, 6B2E9 and 6B2G12, in particular, retained their non-specificity after further subcloning (FIG. 14B).

Figures 15A, 15B:
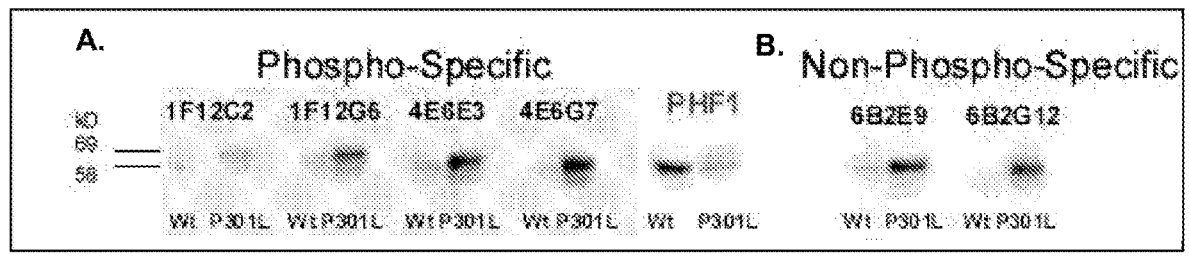
FIGS. 15A-15B are western blots showing reactivity of the four Tau-386-408[P-Ser$_{396, 404}$] phospho-specific (FIG. 15A) and non-phospho-specific (FIG. 15B) monoclonal antibody clones with brain homogenates from the JNPL3 P301L mouse and wildtype (Wt) mouse. Of the four phospho-specific clones, 4E6G7 shows the strongest reactivity, which is consistent with the ELISA results of FIG. 14A. In contrast with the PHF-1 antibody that also recognizes the tau P-Ser$_{396, 404}$ epitope, all clones react better with the JNPL3 P301L brain homogenate than the Wt homogenate. The non-phospho-specific clones reacted faster, as expected, as most of tau is non-phosphorylated.

The reactivity of the four P-Ser$_{396, 404}$ tau phospho-specific (FIG. 15A) and non-phospho-specific (FIG. 15B) monoclonal antibody clones was tested against brain homogenates from the JNPL3 P301L mouse and wildtype (Wt) mouse. Of the four phospho-specific clones, 4E6G7 shows the strongest reactivity (FIG. 15A), which is consistent with the ELISA results of FIG. 14A. In contrast with the PHF-1 antibody that also recognizes the tau P-Ser$_{396, 404}$ epitope, all clones react better with the JNPL3 P301L brain homogenate than the Wt homogenate. The non-phospho-specific clones reacted faster, as expected, as most of tau is non-phosphorylated.

Figures 16A, 16B:
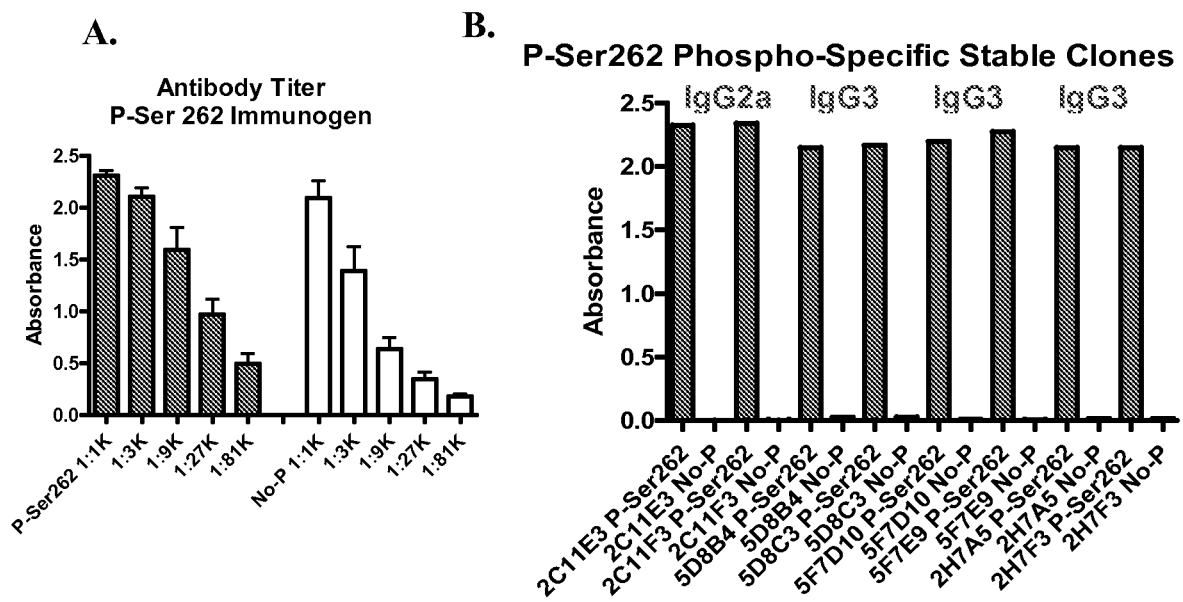
FIGS. 16A-16B illustrate the generation of monoclonal antibodies against the immunogenic tau peptide comprising amino acids 260-271 (SEQ ID NO:12) and containing phosphorylated serine 262 epitope.

Another set of ten balb/c mice was immunized with Tau260-271[P-Ser$_{262}$] (SEQ ID NO:12) linked to KLH via a cysteine residue on the C-terminus. Although strong titer was generated against the Tau260-271[P-Ser$_{262}$] immunogen, plasma antibodies recognized the non-phospho peptide Tau260-271 as well (FIG. 16A). Eight stable phospho-specific clones were selected from the second subcloning for further analysis (FIG. 16B) and the 2C11 clone has been selected for antibody production as it is of the IgG2a isotype. IgG3 has shorter half-life and is therefore not considered ideal for passive immunization studies.

Figure 17:
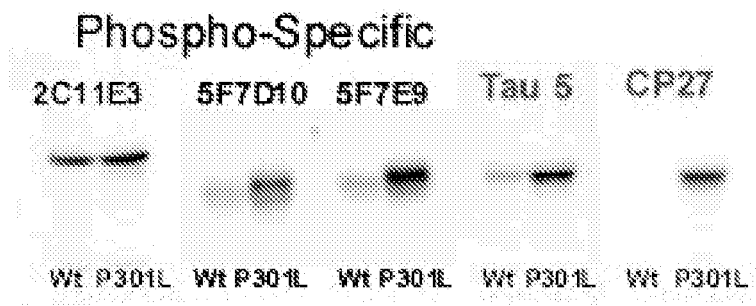
FIG. 17 is a western blot showing the reactivity of the three phospho-specific Tau260-271[P-Ser$_{262}$] monoclonal antibody clones. The 2C11 antibody clone recognizes a higher molecular weight band than the other phospho-specific clones and it does not distinguish between wildtype and P301L tissue. 5F7D10 and 5F7E9 are representatives of the other clones. Tau-5 recognizes total tau and binds to an epitope around amino acids 216-227 of tau. CP27 recognizes human but not mouse tau.

The reactivity of the three phospho-specific P-Ser$_{262}$ tau monoclonal antibody clones against brain homogenates from JNPL3 P301L and wildtype (Wt) mice was assessed (FIG. 17). The 2C11 antibody clone recognizes a higher molecular weight band than the other phospho-specific clones and it does not distinguish between wildtype and P301L tissue. 5F7D10 and 5F7E9 are representatives of the other clones. Tau-5 recognizes total tau and binds to an epitope around amino acids 216-227 of tau. CP27 recognizes human but not mouse tau.

Figures 18A, 18B, 18C, 18D, 18E:
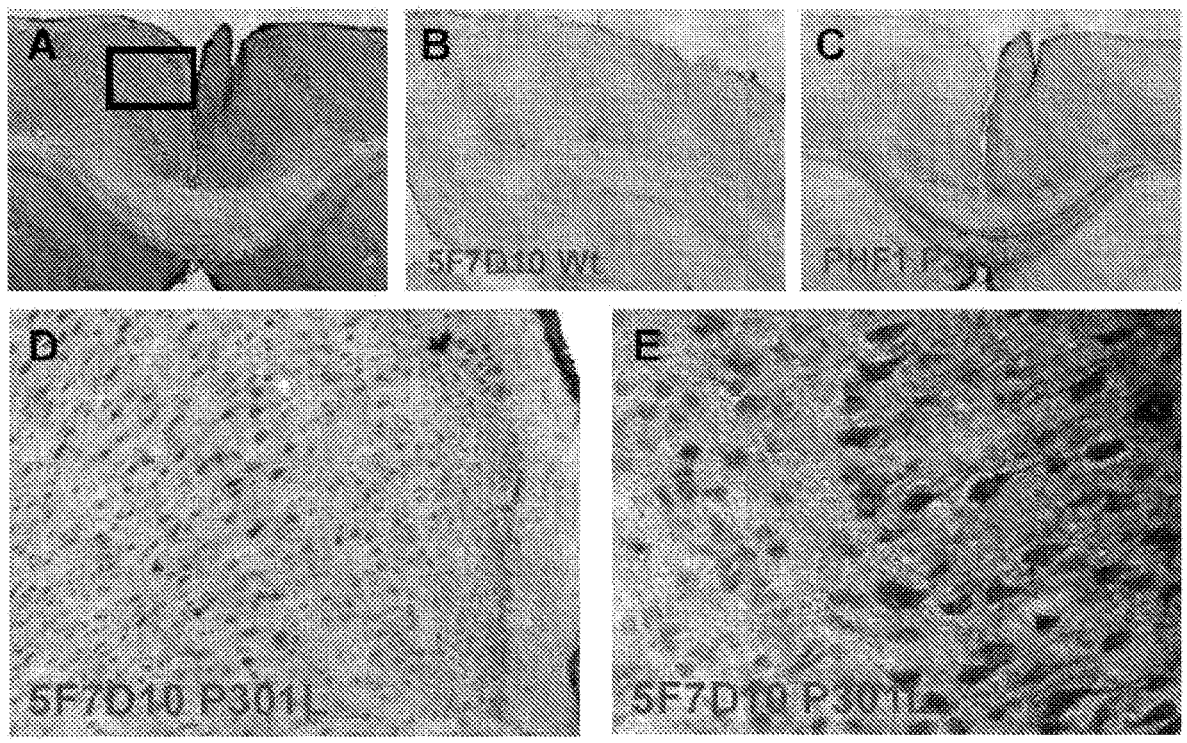
FIGS. 18A-18E are immunohistochemical photomicrographs showing the detection of tau pathology using the 5F7D10 antibody clone in P301L tangle mouse brain sections. The 5F7D10 monoclonal antibody shows strong histological staining in the P301L brain section (FIG. 18A) compared to the wildtype (FIG. 18B). The PHF1 antibody picked up tau pathology in the same tangle mouse (FIG. 18C) although the pattern was different than with the 5F7D 10 antibody, which is not surprising as they recognize different tau epitopes.

The 5F7D10 antibody clone readily detected tau pathology in P301L tangle mouse brain sections as shown in FIGS. 18A-18E. The 5F7D10 monoclonal antibody shows strong histological staining in the P301L brain section (FIG. 18A) compared to the wildtype (FIG. 18B). The PHF1 antibody picked up tau pathology in the same tangle mouse (FIG. 18C) although the pattern was different than with the 5F7D10 antibody, which is not surprising as they recognize different tau epitopes. FIG. 18D is a magnified image of the boxed region in FIG. 18A depicting neurons with aggregated tau. FIG. 18E is a higher magnified image of tangle-like pathology detected with 5F7D10 in a different JNPL3 P301L mouse.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of treating Alzheimer's disease or other tauopathy in a subject, or of reducing the severity of Alzheimer's disease or said other tauopathy in said subject, said method comprising:
    administering to said subject an immunogen consisting essentially of an immunogenic tau peptide (I), optionally linked to an immunogenic carrier protein directly, or via a linker peptide, wherein:
    the amino acid sequence of said immunogenic tau peptide (I) consists of the amino acid sequence of:

(a)
                                            SEQ ID NO: 3
    IGS*TE (Tau260-264 P-Ser262);

(b)
                                            SEQ ID NO: 32
    IGXTE (Tau260-264 Pseudo P-Ser262);

(c)
                                            SEQ ID NO: 12
    IGS*TENLKHQPG (Tau260-271 P-Ser262);

(d)
                                            SEQ ID NO: 41
    IGXTENLKHQPG (Tau260-271 Pseudo P-Ser262);

(e)
                                            SEQ ID NO: 20
    VKS*KIGS*TE (Tau256-264 P-Ser262);
    or (f)
                                            SEQ ID NO: 49
    VKXKIGXTE (Tau256-264 Pseudo P-Ser262);

wherein:
    S* and P-Ser denote a phospho-serine residue, and X and Pseudo P-Ser denote a glutamic acid or aspartic acid residue;
    (II) said optionally linked immunogenic carrier protein is a tetanus toxoid, a Hepatitis B surface antigen, a cholera toxin B, a diphtheria toxoid, a measles virus F protein, a *Chlamydia trachomatis* major outer membrane protein, a Plasmodium falciparum circumsporozite protein, a Plasmodium falciparum CS antigen, a Schistosoma mansoni triose phosphate isomerase, an *Escherichia coli* TraT protein, an Influenza virus hemagglutinin, or a keyhole limpet hemocyanine; and
    (III) said linker peptide is GPSL (SEQ ID NO: 78), GSG, GSGS (SEQ ID NO: 79), GSGSG (SEQ ID NO: 80), or $GS_NG$);
    wherein:
    said immunogenic tau peptide (I) peptide is administered in an amount sufficient to elicit an active immune response in said subject to said immunogenic tau peptide; and
    said elicited active immune response provides said subject with treatment of Alzheimer's disease or said other tauopathy or reduces the severity of Alzheimer's disease or said other tauopathy in said subject.

2. The method according to claim 1, wherein said immunogenic tau peptide (I) is linked to said immunogenic carrier.

3. The method according to claim 2, wherein said immunogenic tau peptide (I) is said peptide whose amino acid sequence consists of the amino acid sequence of SEQ ID NO:3 or SEQ ID NO:32.

4. The method according to claim 2, wherein said immunogenic tau peptide (I) is said peptide whose amino acid sequence consists of the amino acid sequence of SEQ ID NO:12 or SEQ ID NO:41.

5. The method according to claim 2, wherein said immunogenic tau peptide (I) is said peptide whose amino acid sequence consists of the amino acid sequence of SEQ ID NO:20 or SEQ ID NO:49.

6. The method according to claim 2, wherein an adjuvant is administered before, after, or concurrent with said administration of said immunogenic tau peptide (I).

7. The method according to claim 2, wherein said method comprises the administration of said immunogenic tau peptide (I), and one or more additional immunogenic tau peptides before, after, or concurrent with said administration of said immunogenic tau peptide (I); wherein each of said additional administered tau peptides has an amino acid sequence selected from the group consisting of SEQ ID NOs:81-100.

8. The method according to claim 2, wherein said immunogenic carrier is keyhole limpet hemocyanin (KLH) or a tetanus toxin that comprises the amino acid sequence: FNNFTVSFWLRVPKVSASHLE (SEQ ID NO: 76) or the amino acid sequence: QYIKANSKFIGIT (SEQ ID NO: 77).

9. The method according to claim 1, wherein said other tauopathy is selected from the group consisting of frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, non-guanamian motor neuron disease with neurofibrillary tangles, chronic traumatic encephalopathy, and postencephalitic parkinsonism.

10. The method according to claim 1, wherein said method promotes reduction or clearance of tau aggregates from the brain of said subject, or reduces the severity of the formation of tau aggregates in said subject.

11. The method according to claim 10, wherein said aggregates are neurofibrillary tangles or their pathological tau precursors.

12. The method according to claim 1, wherein said method slows progression of a tau-pathology related cognitive impairment in said subject, or reduces the severity or duration of said progression in said subject.

13. The method according to claim 1, wherein said elicited active immune response provides said subject with treatment of Alzheimer's disease or reduces the severity of Alzheimer's disease in said subject.

* * * * *

UNITED STATES PATENT AND TRADEMARK OFFICE
CERTIFICATE OF CORRECTION

| | |
|---|---|
| PATENT NO. | : 11,787,854 B2 |
| APPLICATION NO. | : 17/090359 |
| DATED | : October 17, 2023 |
| INVENTOR(S) | : Einar M. Sigurdsson |

It is certified that error appears in the above-identified patent and that said Letters Patent is hereby corrected as shown below:

In the Claims

In Claim 1, Column 109, at Line 10, insert --(I)-- before "the".

Signed and Sealed this
Ninth Day of January, 2024

Katherine Kelly Vidal
*Director of the United States Patent and Trademark Office*

SEQUENCE LISTING

<160> NUMBER OF SEQ ID NOS: 103

<210> SEQ ID NO 1
<211> LENGTH: 441
<212> TYPE: PRT

<213> ORGANISM: Homo Sapiens

<400> SEQUENCE: 1

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
            165                 170                 175

Pro Ala Pro Lys Thr Pro Pro Ser Ser Gly Glu Pro Pro Lys Ser Gly
        180                 185                 190

Asp Arg Ser Gly Tyr Ser Ser Pro Gly Ser Pro Gly Thr Pro Gly Ser
    195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
        260                 265                 270

Gly Lys Val Gln Ile Ile Asn Lys Lys Leu Asp Leu Ser Asn Val Gln
    275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
        340                 345                 350

Lys Ile Gly Ser Leu Asp Asn Ile Thr His Val Pro Gly Gly Gly Asn
    355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
385                 390                 395                 400
```

```
Gly Asp Thr Ser Pro Arg His Leu Ser Asn Val Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 2
<211> LENGTH: 7
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: PHOSPHORYLATION

<400> SEQUENCE: 2

Ser Arg Thr Pro Ser Leu Pro
1               5

<210> SEQ ID NO 3
<211> LENGTH: 5
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION

<400> SEQUENCE: 3

Ile Gly Ser Thr Glu
1               5

<210> SEQ ID NO 4
<211> LENGTH: 9
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 4

Val Arg Thr Pro Pro Lys Ser Pro Ser
1               5

<210> SEQ ID NO 5
<211> LENGTH: 13
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION
```

```
<220> FEATURE:
<221> NAME/KEY: MOD_RES
<222> LOCATION: (11)..(11)
<223> OTHER INFORMATION: PHOSPHORYLATION

<400> SEQUENCE: 5

Tyr Lys Ser Pro Val Val Ser Gly Asp Thr Ser Pro Arg
1               5                   10

<210> SEQ ID NO 6
<211> LENGTH: 30
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (21)..(21)
<223> OTHER INFORMATION: PHOSPHORYLATION
<220> FEATURE:
<221> NAME/KEY: MOD_RES
<222> LOCATION: (23)..(23)
<223> OTHER INFORMATION: PHOSPHORYLATION

<400> SEQUENCE: 6

Gly Asp Arg Ser Gly Tyr Ser Ser Pro Gly Ser Pro Gly Thr Pro Gly
1               5                   10                  15

Ser Arg Ser Arg Thr Pro Ser Leu Pro Thr Pro Pro Thr Arg
            20                  25                  30

<210> SEQ ID NO 7
<211> LENGTH: 30
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (21)..(21)
<223> OTHER INFORMATION: PHOSPHORYLATION
<220> FEATURE:
<221> NAME/KEY: MOD_RES
<222> LOCATION: (23)..(23)
<223> OTHER INFORMATION: PHOSPHORYLATION

<400> SEQUENCE: 7

Gly Asp Arg Ser Gly Tyr Ser Ser Pro Gly Ser Pro Gly Thr Pro Gly
1               5                   10                  15

Ser Arg Ser Arg Thr Pro Ser Leu Pro Thr Pro Pro Thr Arg
            20                  25                  30

<210> SEQ ID NO 8
<211> LENGTH: 30
<212> TYPE: PRT
<213> ORGANISM: Artificial
<220> FEATURE:
<223> OTHER INFORMATION: tau peptide
<220> FEATURE:
<221> NAME/KEY: MOD_RES
```

```
<222> LOCATION: (8)..(8)
<223> OTHER INFORMATION: PHOSPHORYLATION
<220> FEATURE:
<221> NAME/KEY: MOD_RES
<222> LOCATION: (21)..(21)
<223> OTHER INFORMATION: PHOSPHORYLATION
<220> FEATURE:
<221> NAME/KEY: MOD_RES
<222> LOCATION: (23)..(23)
<223> OTHER INFORMATION: PHOSPHORYLATION
<220> FEATURE:
<221> NAME/KEY: MOD_RES
<222> LOCATION: (26)..(26)
<223> OTHER INFORMATION: PHOSPHORYLATION

<400> SEQUENCE: 8

Gly Asp Arg Ser Gly Tyr Ser Ser Pro Gly Ser Pro Gly Thr Pro Gly
1               5                   10                  15

Ser Arg Ser Arg Thr Pro Ser Leu Pro Thr Pro Pro Thr Arg
            20                  25                  30

<210> SEQ ID NO 9
<211> LENGTH: 30
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 9

Gly Asp Arg Ser Gly Tyr Ser Ser Pro Gly Ser Pro Gly Thr Pro Gly
1               5                   10                  15

Ser Arg Ser Arg Thr Pro Ser Leu Pro Thr Pro Pro Thr Arg
            20                  25                  30

<210> SEQ ID NO 10
<211> LENGTH: 30
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (13)..(13)
<223> OTHER INFORMATION: PHOSPHORYLATION
<220> FEATURE:
<221> NAME/KEY: MOD_RES
<222> LOCATION: (15)..(15)
<223> OTHER INFORMATION: PHOSPHORYLATION

<400> SEQUENCE: 10

Pro Gly Ser Pro Gly Thr Pro Gly Ser Arg Ser Arg Thr Pro Ser Leu
1               5                   10                  15

Pro Thr Pro Pro Thr Arg Glu Pro Lys Lys Val Ala Val Val
            20                  25                  30

<210> SEQ ID NO 11
<211> LENGTH: 37
<212> TYPE: PRT
<213> ORGANISM: Artificial
<220> FEATURE:
<223> OTHER INFORMATION: tau peptide
<220> FEATURE:
```

```
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (35)..(35)
<223> OTHER INFORMATION: PHOSPHORYLATION

<400> SEQUENCE: 11

Cys Gly Ser Leu Gly Asn Ile His His Lys Pro Gly Gly Gly Gln Val
1               5                   10                  15

Glu Val Lys Ser Glu Lys Leu Asp Phe Lys Asp Arg Val Gln Ser Lys
            20                  25                  30

Ile Gly Ser Leu Asp
        35

<210> SEQ ID NO 12
<211> LENGTH: 12
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION

<400> SEQUENCE: 12

Ile Gly Ser Thr Glu Asn Leu Lys His Gln Pro Gly
1               5                   10

<210> SEQ ID NO 13
<211> LENGTH: 23
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 13

Thr Asp His Gly Ala Glu Ile Val Tyr Lys Ser Pro Val Val Ser Gly
1               5                   10                  15

Asp Thr Ser Pro Arg His Leu
            20

<210> SEQ ID NO 14
<211> LENGTH: 24
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (22)..(22)
<223> OTHER INFORMATION: PHOSPHORYLATION
```

```
<400> SEQUENCE: 14

Leu Gln Thr Pro Thr Glu Asp Gly Ser Glu Glu Pro Gly Ser Glu Thr
1               5                   10                  15

Ser Asp Ala Lys Ser Thr Pro Thr
                20

<210> SEQ ID NO 15
<211> LENGTH: 5
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION

<400> SEQUENCE: 15

Thr Pro Ser Leu Glu
1               5

<210> SEQ ID NO 16
<211> LENGTH: 5
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION

<400> SEQUENCE: 16

Ile Ala Thr Pro Arg
1               5

<210> SEQ ID NO 17
<211> LENGTH: 5
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION

<400> SEQUENCE: 17

Ala Lys Thr Pro Pro
1               5

<210> SEQ ID NO 18
<211> LENGTH: 17
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
```

-continued

```
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (15)..(15)
<223> OTHER INFORMATION: PHOSPHORYLATION

<400> SEQUENCE: 18

Pro Gly Thr Pro Gly Ser Arg Ser Arg Thr Pro Ser Leu Pro Thr Pro
1               5                   10                  15

Pro

<210> SEQ ID NO 19
<211> LENGTH: 5
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION

<400> SEQUENCE: 19

Pro Lys Ser Pro Ser
1               5

<210> SEQ ID NO 20
<211> LENGTH: 9
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 20

Val Lys Ser Lys Ile Gly Ser Thr Glu
1               5

<210> SEQ ID NO 21
<211> LENGTH: 5
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION

<400> SEQUENCE: 21

Val Gln Ser Lys Cys
1               5

<210> SEQ ID NO 22
<211> LENGTH: 5
<212> TYPE: PRT
```

```
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION

<400> SEQUENCE: 22

Ile Gly Ser Leu Asp
1               5

<210> SEQ ID NO 23
<211> LENGTH: 19
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (15)..(17)
<223> OTHER INFORMATION: PHOSPHORYLATION

<400> SEQUENCE: 23

Val Val Ser Gly Asp Thr Ser Pro Arg His Leu Ser Asn Val Ser Ser
1               5                   10                  15

Thr Gly Ser

<210> SEQ ID NO 24
<211> LENGTH: 18
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (16)..(16)
<223> OTHER INFORMATION: PHOSPHORYLATION

<400> SEQUENCE: 24

Val Asp Ser Pro Gln Leu Ala Thr Leu Ala Asp Glu Val Ser Ala Ser
1               5                   10                  15

Leu Ala

<210> SEQ ID NO 25
<211> LENGTH: 4
<212> TYPE: PRT
```

```
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION

<400> SEQUENCE: 25

Pro Gly Ser Pro
1

<210> SEQ ID NO 26
<211> LENGTH: 5
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION

<400> SEQUENCE: 26

Pro Gly Thr Pro Gly
1               5

<210> SEQ ID NO 27
<211> LENGTH: 11
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 27

Tyr Ser Ser Pro Gly Ser Pro Gly Thr Pro Gly
1               5                   10

<210> SEQ ID NO 28
<211> LENGTH: 11
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 28

Pro Gly Ser Arg Ser Arg Thr Pro Ser Leu Pro
1               5                   10

<210> SEQ ID NO 29
<211> LENGTH: 11
```

```
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 29

Val Arg Thr Pro Pro Lys Ser Pro Ser Ser Ala
1               5                   10

<210> SEQ ID NO 30
<211> LENGTH: 10
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION

<400> SEQUENCE: 30

Pro Lys Thr Pro Pro Ser Ser Gly Glu Pro
1               5                   10

<210> SEQ ID NO 31
<211> LENGTH: 7
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue
<220> FEATURE:
<221> NAME/KEY: MISC_FEATURE
<222> LOCATION: (5)..(5)
<223> OTHER INFORMATION: Xaa is glutamic acid or aspartic acid residue

<400> SEQUENCE: 31

Ser Arg Xaa Pro Xaa Leu Pro
1               5

<210> SEQ ID NO 32
<211> LENGTH: 5
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue
```

```
<400> SEQUENCE: 32

Ile Gly Xaa Thr Glu
1               5

<210> SEQ ID NO 33
<211> LENGTH: 9
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue
<220> FEATURE:
<221> NAME/KEY: MISC_FEATURE
<222> LOCATION: (7)..(7)
<223> OTHER INFORMATION: Xaa is glutamic acid or aspartic acid residue

<400> SEQUENCE: 33

Val Arg Xaa Pro Pro Lys Xaa Pro Ser
1               5

<210> SEQ ID NO 34
<211> LENGTH: 13
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue
<220> FEATURE:
<221> NAME/KEY: MISC_FEATURE
<222> LOCATION: (11)..(11)
<223> OTHER INFORMATION: Xaa is glutamic acid or aspartic acid residue

<400> SEQUENCE: 34

Tyr Lys Xaa Pro Val Val Ser Gly Asp Thr Xaa Pro Arg
1               5                   10

<210> SEQ ID NO 35
<211> LENGTH: 30
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (21)..(21)
<223> OTHER INFORMATION: Xaa is glutamic acid or aspartic acid residue
<220> FEATURE:
<221> NAME/KEY: MISC_FEATURE
<222> LOCATION: (23)..(23)
<223> OTHER INFORMATION: Xaa is glutamic acid or aspartic acid residue

<400> SEQUENCE: 35

Gly Asp Arg Ser Gly Tyr Ser Ser Pro Gly Ser Pro Gly Thr Pro Gly
1               5                   10                  15

Ser Arg Ser Arg Xaa Pro Xaa Leu Pro Thr Pro Pro Thr Arg
            20                  25                  30

<210> SEQ ID NO 36
<211> LENGTH: 30
<212> TYPE: PRT
<213> ORGANISM: Artificial
<220> FEATURE:
<223> OTHER INFORMATION: pseudophosphorylated tau peptide
```

```
<220> FEATURE:
<221> NAME/KEY: MISC_FEATURE
<222> LOCATION: (8)..(8)
<223> OTHER INFORMATION: Xaa is glutamic acid or aspartic acid residue
<220> FEATURE:
<221> NAME/KEY: MISC_FEATURE
<222> LOCATION: (11)..(11)
<223> OTHER INFORMATION: Xaa is glutamic acid or aspartic acid residue
<220> FEATURE:
<221> NAME/KEY: MISC_FEATURE
<222> LOCATION: (14)..(14)
<223> OTHER INFORMATION: Xaa is glutamic acid or aspartic acid residue
<220> FEATURE:
<221> NAME/KEY: MISC_FEATURE
<222> LOCATION: (21)..(21)
<223> OTHER INFORMATION: Xaa is glutamic acid or aspartic acid residue
<220> FEATURE:
<221> NAME/KEY: MISC_FEATURE
<222> LOCATION: (23)..(23)
<223> OTHER INFORMATION: Xaa is glutamic acid or aspartic acid residue

<400> SEQUENCE: 36

Gly Asp Arg Ser Gly Tyr Ser Xaa Pro Gly Xaa Pro Gly Xaa Pro Gly
1               5                   10                  15

Ser Arg Ser Arg Xaa Pro Xaa Leu Pro Thr Pro Pro Thr Arg
            20                  25                  30

<210> SEQ ID NO 37
<211> LENGTH: 30
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (8)..(8)
<223> OTHER INFORMATION: Xaa is glutamic acid or aspartic acid residue
<220> FEATURE:
<221> NAME/KEY: MISC_FEATURE
<222> LOCATION: (21)..(21)
<223> OTHER INFORMATION: Xaa is glutamic acid or aspartic acid residue
<220> FEATURE:
<221> NAME/KEY: MISC_FEATURE
<222> LOCATION: (23)..(23)
<223> OTHER INFORMATION: Xaa is glutamic acid or aspartic acid residue
<220> FEATURE:
<221> NAME/KEY: MISC_FEATURE
<222> LOCATION: (26)..(26)
<223> OTHER INFORMATION: Xaa is glutamic acid or aspartic acid residue

<400> SEQUENCE: 37

Gly Asp Arg Ser Gly Tyr Ser Xaa Pro Gly Ser Pro Gly Thr Pro Gly
1               5                   10                  15

Ser Arg Ser Arg Xaa Pro Xaa Leu Pro Xaa Pro Pro Thr Arg
            20                  25                  30

<210> SEQ ID NO 38
<211> LENGTH: 30
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (11)..(11)
<223> OTHER INFORMATION: Xaa is glutamic acid or aspartic acid residue
<220> FEATURE:
<221> NAME/KEY: MISC_FEATURE
<222> LOCATION: (14)..(14)
<223> OTHER INFORMATION: Xaa is glutamic acid or aspartic acid residue
```

-continued

<400> SEQUENCE: 38

Gly Asp Arg Ser Gly Tyr Ser Ser Pro Gly Xaa Pro Gly Xaa Pro Gly
1               5                   10                  15

Ser Arg Ser Arg Thr Pro Ser Leu Pro Thr Pro Pro Thr Arg
            20                  25                  30

<210> SEQ ID NO 39
<211> LENGTH: 30
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (13)..(13)
<223> OTHER INFORMATION: Xaa is glutamic acid or aspartic acid residue
<220> FEATURE:
<221> NAME/KEY: MISC_FEATURE
<222> LOCATION: (15)..(15)
<223> OTHER INFORMATION: Xaa is glutamic acid or aspartic acid residue

<400> SEQUENCE: 39

Pro Gly Ser Pro Gly Thr Pro Gly Ser Arg Ser Arg Xaa Pro Xaa Leu
1               5                   10                  15

Pro Thr Pro Pro Thr Arg Glu Pro Lys Lys Val Ala Val Val
            20                  25                  30

<210> SEQ ID NO 40
<211> LENGTH: 37
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue
<220> FEATURE:
<221> NAME/KEY: MISC_FEATURE
<222> LOCATION: (35)..(35)
<223> OTHER INFORMATION: Xaa is glutamic acid or aspartic acid residue

<400> SEQUENCE: 40

Cys Gly Xaa Leu Gly Asn Ile His His Lys Pro Gly Gly Gly Gln Val
1               5                   10                  15

Glu Val Lys Ser Glu Lys Leu Asp Phe Lys Asp Arg Val Gln Ser Lys
            20                  25                  30

Ile Gly Xaa Leu Asp
        35

<210> SEQ ID NO 41
<211> LENGTH: 12
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue

<400> SEQUENCE: 41

Ile Gly Xaa Thr Glu Asn Leu Lys His Gln Pro Gly
1               5                   10

<210> SEQ ID NO 42

```
<211> LENGTH: 23
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (11)..(11)
<223> OTHER INFORMATION: Xaa is glutamic acid or aspartic acid residue
<220> FEATURE:
<221> NAME/KEY: MISC_FEATURE
<222> LOCATION: (19)..(19)
<223> OTHER INFORMATION: Xaa is glutamic acid or aspartic acid residue

<400> SEQUENCE: 42

Thr Asp His Gly Ala Glu Ile Val Tyr Lys Xaa Pro Val Val Ser Gly
1               5                   10                  15

Asp Thr Xaa Pro Arg His Leu
            20

<210> SEQ ID NO 43
<211> LENGTH: 24
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue
<220> FEATURE:
<221> NAME/KEY: MISC_FEATURE
<222> LOCATION: (22)..(22)
<223> OTHER INFORMATION: Xaa is glutamic acid or aspartic acid residue

<400> SEQUENCE: 43

Leu Gln Xaa Pro Thr Glu Asp Gly Ser Glu Glu Pro Gly Ser Glu Thr
1               5                   10                  15

Ser Asp Ala Lys Ser Xaa Pro Thr
            20

<210> SEQ ID NO 44
<211> LENGTH: 5
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue

<400> SEQUENCE: 44

Thr Pro Xaa Leu Glu
1               5

<210> SEQ ID NO 45
<211> LENGTH: 5
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue

<400> SEQUENCE: 45

Ile Ala Xaa Pro Arg
1               5
```

```
<210> SEQ ID NO 46
<211> LENGTH: 5
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue

<400> SEQUENCE: 46

Ala Lys Xaa Pro Pro
1               5

<210> SEQ ID NO 47
<211> LENGTH: 17
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue
<220> FEATURE:
<221> NAME/KEY: MISC_FEATURE
<222> LOCATION: (6)..(6)
<223> OTHER INFORMATION: Xaa is glutamic acid or aspartic acid residue
<220> FEATURE:
<221> NAME/KEY: MISC_FEATURE
<222> LOCATION: (8)..(8)
<223> OTHER INFORMATION: Xaa is glutamic acid or aspartic acid residue
<220> FEATURE:
<221> NAME/KEY: MISC_FEATURE
<222> LOCATION: (10)..(10)
<223> OTHER INFORMATION: Xaa is glutamic acid or aspartic acid residue
<220> FEATURE:
<221> NAME/KEY: MISC_FEATURE
<222> LOCATION: (12)..(12)
<223> OTHER INFORMATION: Xaa is glutamic acid or aspartic acid residue
<220> FEATURE:
<221> NAME/KEY: MISC_FEATURE
<222> LOCATION: (15)..(15)
<223> OTHER INFORMATION: Xaa is glutamic acid or aspartic acid residue

<400> SEQUENCE: 47

Pro Gly Xaa Pro Gly Xaa Arg Xaa Arg Xaa Pro Xaa Leu Pro Xaa Pro
1               5                   10                  15

Pro

<210> SEQ ID NO 48
<211> LENGTH: 5
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue

<400> SEQUENCE: 48

Pro Lys Xaa Pro Ser
1               5

<210> SEQ ID NO 49
<211> LENGTH: 9
<212> TYPE: PRT
<213> ORGANISM: Artificial
```

```
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue
<220> FEATURE:
<221> NAME/KEY: MISC_FEATURE
<222> LOCATION: (7)..(7)
<223> OTHER INFORMATION: Xaa is glutamic acid or aspartic acid residue

<400> SEQUENCE: 49

Val Lys Xaa Lys Ile Gly Xaa Thr Glu
1               5

<210> SEQ ID NO 50
<211> LENGTH: 5
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue

<400> SEQUENCE: 50

Val Gln Xaa Lys Cys
1               5

<210> SEQ ID NO 51
<211> LENGTH: 5
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue

<400> SEQUENCE: 51

Ile Gly Xaa Leu Asp
1               5

<210> SEQ ID NO 52
<211> LENGTH: 19
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue
<220> FEATURE:
<221> NAME/KEY: MISC_FEATURE
<222> LOCATION: (6)..(6)
<223> OTHER INFORMATION: Xaa is glutamic acid or aspartic acid residue
<220> FEATURE:
<221> NAME/KEY: MISC_FEATURE
<222> LOCATION: (12)..(12)
<223> OTHER INFORMATION: Xaa is glutamic acid or aspartic acid residue
<220> FEATURE:
<221> NAME/KEY: MISC_FEATURE
<222> LOCATION: (15)..(17)
<223> OTHER INFORMATION: Xaa is glutamic acid or aspartic acid residue
```

<400> SEQUENCE: 52

Val Val Xaa Gly Asp Xaa Ser Pro Arg His Leu Xaa Asn Val Xaa Xaa
1               5                   10                  15

Xaa Gly Ser

<210> SEQ ID NO 53
<211> LENGTH: 18
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue
<220> FEATURE:
<221> NAME/KEY: MISC_FEATURE
<222> LOCATION: (8)..(8)
<223> OTHER INFORMATION: Xaa is glutamic acid or aspartic acid residue
<220> FEATURE:
<221> NAME/KEY: MISC_FEATURE
<222> LOCATION: (14)..(14)
<223> OTHER INFORMATION: Xaa is glutamic acid or aspartic acid residue
<220> FEATURE:
<221> NAME/KEY: MISC_FEATURE
<222> LOCATION: (16)..(16)
<223> OTHER INFORMATION: Xaa is glutamic acid or aspartic acid residue

<400> SEQUENCE: 53

Val Asp Xaa Pro Gln Leu Ala Xaa Leu Ala Asp Glu Val Xaa Ala Xaa
1               5                   10                  15

Leu Ala

<210> SEQ ID NO 54
<211> LENGTH: 4
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue

<400> SEQUENCE: 54

Pro Gly Xaa Pro
1

<210> SEQ ID NO 55
<211> LENGTH: 5
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue

<400> SEQUENCE: 55

Pro Gly Xaa Pro Gly
1               5

<210> SEQ ID NO 56
<211> LENGTH: 31
<212> TYPE: PRT
<213> ORGANISM: Artificial
<220> FEATURE:

<223> OTHER INFORMATION: pseudophosphorylated tau peptide
<220> FEATURE:
<221> NAME/KEY: MISC_FEATURE
<222> LOCATION: (17)..(17)
<223> OTHER INFORMATION: Xaa is glutamic acid or aspartic acid residue
<220> FEATURE:
<221> NAME/KEY: MISC_FEATURE
<222> LOCATION: (21)..(21)
<223> OTHER INFORMATION: Xaa is glutamic acid or aspartic acid residue

<400> SEQUENCE: 56

Asp Gly Thr Gly Ser Asp Asp Lys Lys Ala Lys Gly Ala Asp Gly Lys
1               5                   10                  15

Xaa Lys Ile Ala Xaa Thr Pro Arg Gly Ala Ala Pro Pro Gly Gln
            20                  25                  30

<210> SEQ ID NO 57
<211> LENGTH: 30
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (18)..(18)
<223> OTHER INFORMATION: Xaa is glutamic acid or aspartic acid residue
<220> FEATURE:
<221> NAME/KEY: MISC_FEATURE
<222> LOCATION: (26)..(26)
<223> OTHER INFORMATION: Xaa is glutamic acid or aspartic acid residue

<400> SEQUENCE: 57

Arg Glu Asn Ala Lys Ala Lys Thr Asp His Gly Ala Glu Ile Val Tyr
1               5                   10                  15

Lys Xaa Pro Val Val Ser Gly Asp Thr Xaa Pro Arg His Leu
            20                  25                  30

<210> SEQ ID NO 58
<211> LENGTH: 30
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (8)..(8)
<223> OTHER INFORMATION: Xaa is glutamic acid or aspartic acid residue
<220> FEATURE:
<221> NAME/KEY: MISC_FEATURE
<222> LOCATION: (11)..(11)
<223> OTHER INFORMATION: Xaa is glutamic acid or aspartic acid residue
<220> FEATURE:
<221> NAME/KEY: MISC_FEATURE
<222> LOCATION: (14)..(14)
<223> OTHER INFORMATION: Xaa is glutamic acid or aspartic acid residue
<220> FEATURE:
<221> NAME/KEY: MISC_FEATURE
<222> LOCATION: (21)..(21)
<223> OTHER INFORMATION: Xaa is glutamic acid or aspartic acid residue
<220> FEATURE:
<221> NAME/KEY: MISC_FEATURE
<222> LOCATION: (23)..(23)
<223> OTHER INFORMATION: Xaa is glutamic acid or aspartic acid residue

<400> SEQUENCE: 58

Gly Asp Arg Ser Gly Tyr Ser Xaa Pro Gly Xaa Pro Gly Xaa Pro Gly
1               5                   10                  15

Ser Arg Ser Arg Xaa Pro Xaa Leu Pro Thr Pro Pro Thr Arg
            20                  25                  30

```
<210> SEQ ID NO 59
<211> LENGTH: 30
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (11)..(11)
<223> OTHER INFORMATION: Xaa is glutamic acid or aspartic acid residue
<220> FEATURE:
<221> NAME/KEY: MISC_FEATURE
<222> LOCATION: (15)..(15)
<223> OTHER INFORMATION: Xaa is glutamic acid or aspartic acid residue

<400> SEQUENCE: 59

Arg Glu Pro Lys Lys Val Ala Val Val Arg Xaa Pro Pro Lys Xaa Pro
1               5                   10                  15

Ser Ser Ala Lys Ser Arg Leu Gln Thr Ala Pro Val Pro Met
            20                  25                  30

<210> SEQ ID NO 60
<211> LENGTH: 29
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (1)..(1)
<223> OTHER INFORMATION: Xaa is glutamic acid or aspartic acid residue
<220> FEATURE:
<221> NAME/KEY: MISC_FEATURE
<222> LOCATION: (8)..(8)
<223> OTHER INFORMATION: Xaa is glutamic acid or aspartic acid residue
<220> FEATURE:
<221> NAME/KEY: MISC_FEATURE
<222> LOCATION: (14)..(16)
<223> OTHER INFORMATION: Xaa is glutamic acid or aspartic acid residue
<220> FEATURE:
<221> NAME/KEY: MISC_FEATURE
<222> LOCATION: (19)..(19)
<223> OTHER INFORMATION: Xaa is glutamic acid or aspartic acid residue
<220> FEATURE:
<221> NAME/KEY: MISC_FEATURE
<222> LOCATION: (22)..(22)
<223> OTHER INFORMATION: Xaa is glutamic acid or aspartic acid residue
<220> FEATURE:
<221> NAME/KEY: MISC_FEATURE
<222> LOCATION: (25)..(25)
<223> OTHER INFORMATION: Xaa is glutamic acid or aspartic acid residue
<220> FEATURE:
<221> NAME/KEY: MISC_FEATURE
<222> LOCATION: (27)..(27)
<223> OTHER INFORMATION: Xaa is glutamic acid or aspartic acid residue
<220> FEATURE:
<221> NAME/KEY: MISC_FEATURE
<222> LOCATION: (29)..(29)
<223> OTHER INFORMATION: Xaa is glutamic acid or aspartic acid residue

<400> SEQUENCE: 60

Xaa Ser Gly Glu Pro Pro Lys Xaa Gly Asp Arg Ser Gln Xaa Xaa Xaa
1               5                   10                  15

Pro Gly Xaa Pro Gly Xaa Pro Gly Xaa Arg Xaa Arg Xaa
            20                  25

<210> SEQ ID NO 61
<211> LENGTH: 30
<212> TYPE: PRT
<213> ORGANISM: Artificial
<220> FEATURE:
<223> OTHER INFORMATION: pseudophosphorylated tau peptide
<220> FEATURE:
```

<221> NAME/KEY: MISC_FEATURE
<222> LOCATION: (18)..(18)
<223> OTHER INFORMATION: Xaa is glutamic acid or aspartic acid residue
<220> FEATURE:
<221> NAME/KEY: MISC_FEATURE
<222> LOCATION: (29)..(29)
<223> OTHER INFORMATION: Xaa is glutamic acid or aspartic acid residue

<400> SEQUENCE: 61

Met Ala Glu Pro Arg Gln Glu Phe Glu Val Met Glu Asp His Ala Gly
1               5                   10                  15

Thr Xaa Gly Leu Gly Asp Arg Lys Asp Gln Gly Gly Xaa Thr
            20                  25                  30

<210> SEQ ID NO 62
<211> LENGTH: 31
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (10)..(10)
<223> OTHER INFORMATION: Xaa is glutamic acid or aspartic acid residue
<220> FEATURE:
<221> NAME/KEY: MISC_FEATURE
<222> LOCATION: (17)..(17)
<223> OTHER INFORMATION: Xaa is glutamic acid or aspartic acid residue
<220> FEATURE:
<221> NAME/KEY: MISC_FEATURE
<222> LOCATION: (21)..(21)
<223> OTHER INFORMATION: Xaa is glutamic acid or aspartic acid residue
<220> FEATURE:
<221> NAME/KEY: MISC_FEATURE
<222> LOCATION: (23)..(23)
<223> OTHER INFORMATION: Xaa is glutamic acid or aspartic acid residue
<220> FEATURE:
<221> NAME/KEY: MISC_FEATURE
<222> LOCATION: (27)..(27)
<223> OTHER INFORMATION: Xaa is glutamic acid or aspartic acid residue

<400> SEQUENCE: 62

Thr Met His Gln Asp Gln Glu Gly Asp Xaa Asp Ala Gly Leu Lys Glu
1               5                   10                  15

Xaa Pro Leu Gln Xaa Pro Xaa Glu Asp Gly Xaa Glu Glu Pro Gly
            20                  25                  30

<210> SEQ ID NO 63
<211> LENGTH: 31
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (9)..(10)
<223> OTHER INFORMATION: Xaa is glutamic acid or aspartic acid residue
<220> FEATURE:
<221> NAME/KEY: MISC_FEATURE
<222> LOCATION: (12)..(12)
<223> OTHER INFORMATION: Xaa is glutamic acid or aspartic acid residue

<400> SEQUENCE: 63

Gly Ser Glu Thr Ser Asp Ala Lys Xaa Xaa Pro Xaa Ala Glu Asp Val
1               5                   10                  15

Thr Ala Pro Leu Val Asp Glu Gly Ala Pro Gly Lys Gln Ala Ala
            20                  25                  30

<210> SEQ ID NO 64
<211> LENGTH: 31

```
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (6)..(6)
<223> OTHER INFORMATION: Xaa is glutamic acid or aspartic acid residue
<220> FEATURE:
<221> NAME/KEY: MISC_FEATURE
<222> LOCATION: (12)..(13)
<223> OTHER INFORMATION: Xaa is glutamic acid or aspartic acid residue
<220> FEATURE:
<221> NAME/KEY: MISC_FEATURE
<222> LOCATION: (24)..(24)
<223> OTHER INFORMATION: Xaa is glutamic acid or aspartic acid residue

<400> SEQUENCE: 64

Ala Ala Gln Pro His Xaa Glu Ile Pro Glu Gly Xaa Xaa Ala Glu Glu
 1               5                  10                  15

Ala Gly Ile Gly Asp Thr Pro Xaa Leu Glu Asp Glu Ala Ala Gly
            20                  25                  30

<210> SEQ ID NO 65
<211> LENGTH: 31
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (4)..(4)
<223> OTHER INFORMATION: Xaa is glutamic acid or aspartic acid residue
<220> FEATURE:
<221> NAME/KEY: MISC_FEATURE
<222> LOCATION: (12)..(12)
<223> OTHER INFORMATION: Xaa is glutamic acid or aspartic acid residue
<220> FEATURE:
<221> NAME/KEY: MISC_FEATURE
<222> LOCATION: (30)..(30)
<223> OTHER INFORMATION: Xaa is glutamic acid or aspartic acid residue

<400> SEQUENCE: 65

Gly His Val Xaa Gln Ala Arg Met Val Ser Lys Xaa Lys Asp Gly Thr
 1               5                  10                  15

Gly Ser Asp Asp Lys Lys Ala Lys Gly Ala Asp Gly Lys Xaa Lys
            20                  25                  30

<210> SEQ ID NO 66
<211> LENGTH: 31
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (26)..(26)
<223> OTHER INFORMATION: Xaa is glutamic acid or aspartic acid residue

<400> SEQUENCE: 66

Lys Ile Ala Thr Pro Arg Gly Ala Ala Pro Pro Gly Gln Lys Gly Gln
 1               5                  10                  15

Ala Asn Ala Thr Arg Ile Pro Ala Lys Xaa Pro Pro Ala Pro Lys
            20                  25                  30

<210> SEQ ID NO 67
<211> LENGTH: 31
<212> TYPE: PRT
<213> ORGANISM: Artificial
<220> FEATURE:
```

<223> OTHER INFORMATION: pseudophosphorylated tau peptide
<220> FEATURE:
<221> NAME/KEY: MISC_FEATURE
<222> LOCATION: (2)..(2)
<223> OTHER INFORMATION: Xaa is glutamic acid or aspartic acid residue
<220> FEATURE:
<221> NAME/KEY: MISC_FEATURE
<222> LOCATION: (5)..(6)
<223> OTHER INFORMATION: Xaa is glutamic acid or aspartic acid residue
<220> FEATURE:
<221> NAME/KEY: MISC_FEATURE
<222> LOCATION: (18)..(20)
<223> OTHER INFORMATION: Xaa is glutamic acid or aspartic acid residue
<220> FEATURE:
<221> NAME/KEY: MISC_FEATURE
<222> LOCATION: (23)..(23)
<223> OTHER INFORMATION: Xaa is glutamic acid or aspartic acid residue
<220> FEATURE:
<221> NAME/KEY: MISC_FEATURE
<222> LOCATION: (26)..(26)
<223> OTHER INFORMATION: Xaa is glutamic acid or aspartic acid residue
<220> FEATURE:
<221> NAME/KEY: MISC_FEATURE
<222> LOCATION: (29)..(29)
<223> OTHER INFORMATION: Xaa is glutamic acid or aspartic acid residue

<400> SEQUENCE: 67

Lys Xaa Pro Pro Xaa Xaa Gly Glu Pro Pro Lys Ser Gly Asp Arg Ser
1               5                   10                  15
Gly Xaa Xaa Xaa Pro Gly Xaa Pro Gly Xaa Pro Gly Xaa Arg Ser
            20                  25                  30

<210> SEQ ID NO 68
<211> LENGTH: 31
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (3)..(3)
<223> OTHER INFORMATION: Xaa is glutamic acid or aspartic acid residue
<220> FEATURE:
<221> NAME/KEY: MISC_FEATURE
<222> LOCATION: (5)..(5)
<223> OTHER INFORMATION: Xaa is glutamic acid or aspartic acid residue
<220> FEATURE:
<221> NAME/KEY: MISC_FEATURE
<222> LOCATION: (8)..(8)
<223> OTHER INFORMATION: Xaa is glutamic acid or aspartic acid residue
<220> FEATURE:
<221> NAME/KEY: MISC_FEATURE
<222> LOCATION: (22)..(22)
<223> OTHER INFORMATION: Xaa is glutamic acid or aspartic acid residue
<220> FEATURE:
<221> NAME/KEY: MISC_FEATURE
<222> LOCATION: (26)..(26)
<223> OTHER INFORMATION: Xaa is glutamic acid or aspartic acid residue
<220> FEATURE:
<221> NAME/KEY: MISC_FEATURE
<222> LOCATION: (28)..(29)
<223> OTHER INFORMATION: Xaa is glutamic acid or aspartic acid residue

<400> SEQUENCE: 68

Ser Arg Xaa Pro Xaa Leu Pro Xaa Pro Pro Thr Arg Glu Pro Lys Lys
1               5                   10                  15
Val Ala Val Val Arg Xaa Pro Pro Lys Xaa Pro Xaa Xaa Ala Lys
            20                  25                  30

<210> SEQ ID NO 69
<211> LENGTH: 31
<212> TYPE: PRT
<213> ORGANISM: Artificial

```
<220> FEATURE:
<223> OTHER INFORMATION: pseudophosphorylated tau peptide
<220> FEATURE:
<221> NAME/KEY: MISC_FEATURE
<222> LOCATION: (23)..(23)
<223> OTHER INFORMATION: Xaa is glutamic acid or aspartic acid residue

<400> SEQUENCE: 69

Lys Ser Arg Leu Gln Thr Ala Pro Val Pro Met Pro Asp Leu Lys Asn
1               5                   10                  15

Val Lys Ser Lys Ile Gly Xaa Thr Glu Asn Leu Lys His Gln Pro
            20                  25                  30

<210> SEQ ID NO 70
<211> LENGTH: 31
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (24)..(24)
<223> OTHER INFORMATION: Xaa is glutamic acid or aspartic acid residue

<400> SEQUENCE: 70

Pro Gly Gly Gly Lys Val Gln Ile Ile Asn Lys Lys Leu Asp Leu Ser
1               5                   10                  15

Asn Val Gln Ser Lys Cys Gly Xaa Lys Asp Asn Ile Lys His Val
            20                  25                  30

<210> SEQ ID NO 71
<211> LENGTH: 31
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (11)..(11)
<223> OTHER INFORMATION: Xaa is glutamic acid or aspartic acid residue
<220> FEATURE:
<221> NAME/KEY: MISC_FEATURE
<222> LOCATION: (25)..(25)
<223> OTHER INFORMATION: Xaa is glutamic acid or aspartic acid residue

<400> SEQUENCE: 71

Val Pro Gly Gly Gly Ser Val Gln Ile Val Xaa Lys Pro Val Asp Leu
1               5                   10                  15

Ser Lys Val Thr Ser Lys Cys Gly Xaa Leu Gly Asn Ile His His
            20                  25                  30

<210> SEQ ID NO 72
<211> LENGTH: 31
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (27)..(27)
<223> OTHER INFORMATION: Xaa is glutamic acid or aspartic acid residue

<400> SEQUENCE: 72

His Lys Pro Gly Gly Gly Gln Val Glu Val Lys Ser Glu Lys Leu Asp
1               5                   10                  15

Phe Lys Asp Arg Val Gln Ser Lys Ile Gly Xaa Leu Asp Asn Ile
            20                  25                  30
```

```
<210> SEQ ID NO 73
<211> LENGTH: 31
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (2)..(2)
<223> OTHER INFORMATION: Xaa is glutamic acid or aspartic acid residue
<220> FEATURE:
<221> NAME/KEY: MISC_FEATURE
<222> LOCATION: (14)..(14)
<223> OTHER INFORMATION: Xaa is glutamic acid or aspartic acid residue
<220> FEATURE:
<221> NAME/KEY: MISC_FEATURE
<222> LOCATION: (27)..(27)
<223> OTHER INFORMATION: Xaa is glutamic acid or aspartic acid residue

<400> SEQUENCE: 73

Ile Xaa His Val Pro Gly Gly Gly Asn Lys Lys Ile Glu Xaa His Lys
1               5                   10                  15

Leu Thr Phe Arg Glu Asn Ala Lys Ala Lys Xaa Asp His Gly Ala
            20                  25                  30

<210> SEQ ID NO 74
<211> LENGTH: 31
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (5)..(5)
<223> OTHER INFORMATION: Xaa is glutamic acid or aspartic acid residue
<220> FEATURE:
<221> NAME/KEY: MISC_FEATURE
<222> LOCATION: (7)..(7)
<223> OTHER INFORMATION: Xaa is glutamic acid or aspartic acid residue
<220> FEATURE:
<221> NAME/KEY: MISC_FEATURE
<222> LOCATION: (11)..(11)
<223> OTHER INFORMATION: Xaa is glutamic acid or aspartic acid residue
<220> FEATURE:
<221> NAME/KEY: MISC_FEATURE
<222> LOCATION: (14)..(15)
<223> OTHER INFORMATION: Xaa is glutamic acid or aspartic acid residue
<220> FEATURE:
<221> NAME/KEY: MISC_FEATURE
<222> LOCATION: (20)..(20)
<223> OTHER INFORMATION: Xaa is glutamic acid or aspartic acid residue
<220> FEATURE:
<221> NAME/KEY: MISC_FEATURE
<222> LOCATION: (23)..(24)
<223> OTHER INFORMATION: Xaa is glutamic acid or aspartic acid residue

<400> SEQUENCE: 74

Ala Glu Ile Val Xaa Lys Xaa Pro Val Val Xaa Gly Asp Xaa Xaa Pro
1               5                   10                  15

Arg His Leu Xaa Asn Val Xaa Xaa Thr Gly Ser Ile Asp Met Val
            20                  25                  30

<210> SEQ ID NO 75
<211> LENGTH: 31
<212> TYPE: PRT
<213> ORGANISM: Artificial
<220> FEATURE:
<223> OTHER INFORMATION: pseudophosphorylated tau peptide
<220> FEATURE:
<221> NAME/KEY: MISC_FEATURE
<222> LOCATION: (2)..(3)
<223> OTHER INFORMATION: Xaa is glutamic acid or aspartic acid residue
```

```
<220> FEATURE:
<221> NAME/KEY: MISC_FEATURE
<222> LOCATION: (12)..(12)
<223> OTHER INFORMATION: Xaa is glutamic acid or aspartic acid residue

<400> SEQUENCE: 75

Val Xaa Xaa Thr Gly Ser Ile Asp Met Val Asp Xaa Pro Gln Leu Ala
1               5                   10                  15

Thr Leu Ala Asp Glu Val Ser Ala Ser Leu Ala Lys Gln Gly Leu
            20                  25                  30

<210> SEQ ID NO 76
<211> LENGTH: 21
<212> TYPE: PRT
<213> ORGANISM: Artificial
<220> FEATURE:
<223> OTHER INFORMATION: T-helper cell epitope

<400> SEQUENCE: 76

Phe Asn Asn Phe Thr Val Ser Phe Trp Leu Arg Val Pro Lys Val Ser
1               5                   10                  15

Ala Ser His Leu Glu
            20

<210> SEQ ID NO 77
<211> LENGTH: 13
<212> TYPE: PRT
<213> ORGANISM: Artificial
<220> FEATURE:
<223> OTHER INFORMATION: T-helper cell epitope

<400> SEQUENCE: 77

Gln Tyr Ile Lys Ala Asn Ser Lys Phe Ile Gly Ile Thr
1               5                   10

<210> SEQ ID NO 78
<211> LENGTH: 4
<212> TYPE: PRT
<213> ORGANISM: Artificial
<220> FEATURE:
<223> OTHER INFORMATION: linker

<400> SEQUENCE: 78

Gly Pro Ser Leu
1

<210> SEQ ID NO 79
<211> LENGTH: 4
<212> TYPE: PRT
<213> ORGANISM: Artificial
<220> FEATURE:
<223> OTHER INFORMATION: linker

<400> SEQUENCE: 79

Gly Ser Gly Ser
1

<210> SEQ ID NO 80
<211> LENGTH: 5
<212> TYPE: PRT
<213> ORGANISM: Artificial
<220> FEATURE:
<223> OTHER INFORMATION: linker
```

```
<400> SEQUENCE: 80

Gly Ser Gly Ser Gly
1               5

<210> SEQ ID NO 81
<211> LENGTH: 30
<212> TYPE: PRT
<213> ORGANISM: Artificial
<220> FEATURE:
<223> OTHER INFORMATION: tau peptide

<400> SEQUENCE: 81

Asp Gly Thr Gly Ser Asp Asp Lys Lys Ala Lys Gly Ala Asp Gly Lys
1               5                   10                  15

Thr Lys Ile Ala Thr Pro Arg Gly Ala Ala Pro Pro Gly Gln
            20                  25                  30

<210> SEQ ID NO 82
<211> LENGTH: 30
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (26)..(26)
<223> OTHER INFORMATION: PHOSPHORYLATION

<400> SEQUENCE: 82

Arg Glu Asn Ala Lys Ala Lys Thr Asp His Gly Ala Glu Ile Val Tyr
1               5                   10                  15

Lys Ser Pro Val Val Ser Gly Asp Thr Ser Pro Arg His Leu
            20                  25                  30

<210> SEQ ID NO 83
<211> LENGTH: 30
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (21)..(21)
<223> OTHER INFORMATION: PHOSPHORYLATION
<220> FEATURE:
<221> NAME/KEY: MOD_RES
<222> LOCATION: (23)..(23)
<223> OTHER INFORMATION: PHOSPHORYLATION

<400> SEQUENCE: 83

Gly Asp Arg Ser Gly Tyr Ser Ser Pro Gly Ser Pro Gly Thr Pro Gly
1               5                   10                  15
```

Ser Arg Ser Arg Thr Pro Ser Leu Pro Thr Pro Pro Thr Arg
            20                  25                  30

<210> SEQ ID NO 84
<211> LENGTH: 30
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (15)..(15)
<223> OTHER INFORMATION: PHOSPHORYLATION

<400> SEQUENCE: 84

Arg Glu Pro Lys Lys Val Ala Val Val Arg Thr Pro Pro Lys Ser Pro
1               5                   10                  15

Ser Ser Ala Lys Ser Arg Leu Gln Thr Ala Pro Val Pro Met
            20                  25                  30

<210> SEQ ID NO 85
<211> LENGTH: 29
<212> TYPE: PRT
<213> ORGANISM: Artificial
<220> FEATURE:
<223> OTHER INFORMATION: tau peptide

<400> SEQUENCE: 85

Ser Ser Gly Glu Pro Pro Lys Ser Gly Asp Arg Ser Gln Tyr Ser Ser
1               5                   10                  15

Pro Gly Ser Pro Gly Thr Pro Gly Ser Arg Ser Arg Thr
            20                  25

<210> SEQ ID NO 86
<211> LENGTH: 30
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (29)..(29)
<223> OTHER INFORMATION: PHOSPHORYLATION

<400> SEQUENCE: 86

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr
            20                  25                  30

<210> SEQ ID NO 87
<211> LENGTH: 31
<212> TYPE: PRT
<213> ORGANISM: Artificial
<220> FEATURE:
<223> OTHER INFORMATION: tau peptide

<400> SEQUENCE: 87

Thr Met His Gln Asp Gln Glu Gly Asp Thr Asp Ala Gly Leu Lys Glu
1               5                   10                  15

Ser Pro Leu Gln Thr Pro Thr Glu Asp Gly Ser Glu Glu Pro Gly
            20                  25                  30

<210> SEQ ID NO 88
<211> LENGTH: 31
<212> TYPE: PRT
<213> ORGANISM: Artificial
<220> FEATURE:
<223> OTHER INFORMATION: tau peptide

<400> SEQUENCE: 88

Gly Ser Glu Thr Ser Asp Ala Lys Ser Thr Pro Thr Ala Glu Asp Val
1               5                   10                  15

Thr Ala Pro Leu Val Asp Glu Gly Ala Pro Gly Lys Gln Ala Ala
            20                  25                  30

<210> SEQ ID NO 89
<211> LENGTH: 31
<212> TYPE: PRT
<213> ORGANISM: Artificial
<220> FEATURE:
<223> OTHER INFORMATION: tau peptide

<400> SEQUENCE: 89

Ala Ala Gln Pro His Thr Glu Ile Pro Glu Gly Thr Thr Ala Glu Glu
1               5                   10                  15

Ala Gly Ile Gly Asp Thr Pro Ser Leu Glu Asp Glu Ala Ala Gly
            20                  25                  30

<210> SEQ ID NO 90
<211> LENGTH: 31
<212> TYPE: PRT
<213> ORGANISM: Artificial
<220> FEATURE:
<223> OTHER INFORMATION: tau peptide

<400> SEQUENCE: 90

Gly His Val Thr Gln Ala Arg Met Val Ser Lys Ser Lys Asp Gly Thr
1               5                   10                  15

Gly Ser Asp Asp Lys Lys Ala Lys Gly Ala Asp Gly Lys Thr Lys
            20                  25                  30

<210> SEQ ID NO 91
<211> LENGTH: 31
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (26)..(26)
<223> OTHER INFORMATION: PHOSPHORYLATION

<400> SEQUENCE: 91

Lys Ile Ala Thr Pro Arg Gly Ala Ala Pro Pro Gly Gln Lys Gly Gln
1               5                   10                  15

Ala Asn Ala Thr Arg Ile Pro Ala Lys Thr Pro Pro Ala Pro Lys
            20                  25                  30

<210> SEQ ID NO 92
<211> LENGTH: 31
<212> TYPE: PRT
<213> ORGANISM: Artificial
<220> FEATURE:
<223> OTHER INFORMATION: tau peptide

```
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (5)..(6)
<223> OTHER INFORMATION: PHOSPHORYLATION
<220> FEATURE:
<221> NAME/KEY: MOD_RES
<222> LOCATION: (18)..(20)
<223> OTHER INFORMATION: PHOSPHORYLATION
<220> FEATURE:
<221> NAME/KEY: MOD_RES
<222> LOCATION: (23)..(23)
<223> OTHER INFORMATION: PHOSPHORYLATION
<220> FEATURE:
<221> NAME/KEY: MOD_RES
<222> LOCATION: (26)..(26)
<223> OTHER INFORMATION: PHOSPHORYLATION
<220> FEATURE:
<221> NAME/KEY: MOD_RES
<222> LOCATION: (29)..(29)
<223> OTHER INFORMATION: PHOSPHORYLATION

<400> SEQUENCE: 92

Lys Thr Pro Pro Ser Ser Gly Glu Pro Pro Lys Ser Gly Asp Arg Ser
1               5                   10                  15

Gly Tyr Ser Ser Pro Gly Ser Pro Gly Thr Pro Gly Ser Arg Ser
            20                  25                  30

<210> SEQ ID NO 93
<211> LENGTH: 31
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (22)..(22)
<223> OTHER INFORMATION: PHOSPHORYLATION
<220> FEATURE:
<221> NAME/KEY: MOD_RES
<222> LOCATION: (26)..(26)
<223> OTHER INFORMATION: PHOSPHORYLATION
<220> FEATURE:
<221> NAME/KEY: MOD_RES
<222> LOCATION: (28)..(29)
<223> OTHER INFORMATION: PHOSPHORYLATION

<400> SEQUENCE: 93

Ser Arg Thr Pro Ser Leu Pro Thr Pro Pro Thr Arg Glu Pro Lys Lys
1               5                   10                  15

Val Ala Val Val Arg Thr Pro Pro Lys Ser Pro Ser Ser Ala Lys
            20                  25                  30

<210> SEQ ID NO 94
<211> LENGTH: 31
<212> TYPE: PRT
<213> ORGANISM: Artificial
<220> FEATURE:
```

```
<223> OTHER INFORMATION: tau peptide
<220> FEATURE:
<221> NAME/KEY: MOD_RES
<222> LOCATION: (23)..(23)
<223> OTHER INFORMATION: PHOSPHORYLATION

<400> SEQUENCE: 94

Lys Ser Arg Leu Gln Thr Ala Pro Val Pro Met Pro Asp Leu Lys Asn
1               5                   10                  15

Val Lys Ser Lys Ile Gly Ser Thr Glu Asn Leu Lys His Gln Pro
            20                  25                  30

<210> SEQ ID NO 95
<211> LENGTH: 31
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (24)..(24)
<223> OTHER INFORMATION: PHOSPHORYLATION

<400> SEQUENCE: 95

Pro Gly Gly Gly Lys Val Gln Ile Ile Asn Lys Lys Leu Asp Leu Ser
1               5                   10                  15

Asn Val Gln Ser Lys Cys Gly Ser Lys Asp Asn Ile Lys His Val
            20                  25                  30

<210> SEQ ID NO 96
<211> LENGTH: 31
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (25)..(25)
<223> OTHER INFORMATION: PHOSPHORYLATION

<400> SEQUENCE: 96

Val Pro Gly Gly Gly Ser Val Gln Ile Val Tyr Lys Pro Val Asp Leu
1               5                   10                  15

Ser Lys Val Thr Ser Lys Cys Gly Ser Leu Gly Asn Ile His His
            20                  25                  30

<210> SEQ ID NO 97
<211> LENGTH: 31
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (27)..(27)
<223> OTHER INFORMATION: PHOSPHORYLATION

<400> SEQUENCE: 97

His Lys Pro Gly Gly Gly Gln Val Glu Val Lys Ser Glu Lys Leu Asp
1               5                   10                  15

Phe Lys Asp Arg Val Gln Ser Lys Ile Gly Ser Leu Asp Asn Ile
            20                  25                  30
```

```
<210> SEQ ID NO 98
<211> LENGTH: 31
<212> TYPE: PRT
<213> ORGANISM: Artificial
<220> FEATURE:
<223> OTHER INFORMATION: tau peptide

<400> SEQUENCE: 98

Ile Thr His Val Pro Gly Gly Gly Asn Lys Lys Ile Glu Thr His Lys
1               5                   10                  15

Leu Thr Phe Arg Glu Asn Ala Lys Ala Lys Thr Asp His Gly Ala
            20                  25                  30

<210> SEQ ID NO 99
<211> LENGTH: 31
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (14)..(15)
<223> OTHER INFORMATION: PHOSPHORYLATION
<220> FEATURE:
<221> NAME/KEY: MOD_RES
<222> LOCATION: (20)..(20)
<223> OTHER INFORMATION: PHOSPHORYLATION
<220> FEATURE:
<221> NAME/KEY: MOD_RES
<222> LOCATION: (23)..(24)
<223> OTHER INFORMATION: PHOSPHORYLATION

<400> SEQUENCE: 99

Ala Glu Ile Val Tyr Lys Ser Pro Val Val Ser Gly Asp Thr Ser Pro
1               5                   10                  15

Arg His Leu Ser Asn Val Ser Ser Thr Gly Ser Ile Asp Met Val
            20                  25                  30

<210> SEQ ID NO 100
<211> LENGTH: 31
<212> TYPE: PRT
<213> ORGANISM: Artificial
<220> FEATURE:
<223> OTHER INFORMATION: tau peptide
<220> FEATURE:
<221> NAME/KEY: MOD_RES
<222> LOCATION: (2)..(3)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 100

Val Ser Ser Thr Gly Ser Ile Asp Met Val Asp Ser Pro Gln Leu Ala
1               5                   10                  15

Thr Leu Ala Asp Glu Val Ser Ala Ser Leu Ala Lys Gln Gly Leu
            20                  25                  30
```

<210> SEQ ID NO 101
<211> LENGTH: 15
<212> TYPE: PRT
<213> ORGANISM: Artificial
<220> FEATURE:
<223> OTHER INFORMATION: tau peptide

<400> SEQUENCE: 101

His Leu Ser Asn Val Ser Ser Thr Gly Ser Ile Asp Met Val Asp
1               5                   10                  15

<210> SEQ ID NO 102
<211> LENGTH: 13
<212> TYPE: PRT
<213> ORGANISM: Artificial
<220> FEATURE:
<223> OTHER INFORMATION: tau peptide

<400> SEQUENCE: 102

Arg Glu Asn Ala Lys Ala Lys Thr Asp His Gly Ala Glu
1               5                   10

<210> SEQ ID NO 103
<211> LENGTH: 186
<212> TYPE: PRT
<213> ORGANISM: Artificial
<220> FEATURE:
<223> OTHER INFORMATION: tau peptide

<400> SEQUENCE: 103

Glu Ser Pro Leu Gln Thr Pro Thr Glu Asp Gly Ser Glu Glu Pro Gly
1               5                   10                  15

Ser Glu Thr Ser Asp Ala Lys Ser Thr Pro Thr Ala Glu Asp Val Thr
                20                  25                  30

Ala Pro Leu Val Asp Glu Gly Ala Pro Gly Lys Gln Ala Ala Ala Gln
            35                  40                  45

Pro His Thr Glu Ile Pro Glu Gly Thr Thr Ala Glu Glu Ala Gly Ile
        50                  55                  60

Gly Asp Thr Pro Ser Leu Glu Asp Glu Ala Ala Gly His Val Thr Gln
65                  70                  75                  80

Ala Arg Met Val Ser Lys Ser Lys Asp Gly Thr Gly Ser Asp Asp Lys
                85                  90                  95

Lys Ala Lys Gly Ala Asp Gly Lys Thr Lys Ile Ala Thr Pro Arg Gly
            100                 105                 110

Ala Ala Pro Pro Gly Gln Lys Gly Gln Ala Asn Ala Thr Arg Ile Pro
        115                 120                 125

Ala Lys Thr Pro Pro Ala Pro Lys Thr Pro Pro Ser Ser Gly Glu Pro
    130                 135                 140

Pro Lys Ser Gly Asp Arg Ser Gly Tyr Ser Ser Pro Gly Ser Pro Gly
145                 150                 155                 160

Thr Pro Gly Ser Arg Ser Arg Thr Pro Ser Leu Pro Thr Pro Pro Thr
                165                 170                 175

Arg Glu Pro Lys Lys Val Ala Val Val Arg
            180                 185